US009656953B2

(12) United States Patent
Sebti et al.

(10) Patent No.: US 9,656,953 B2
(45) Date of Patent: *May 23, 2017

(54) INHIBITION OF CELL PROLIFERATION

(71) Applicant: University of South Florida, Tampa, FL (US)

(72) Inventors: Said M. Sebti, Tampa, FL (US); Srikumar Chellappan, Tampa, FL (US); Nicholas James Lawrence, Tampa, FL (US)

(73) Assignee: University of South Florida, Tampa, FL (US)

( * ) Notice: Subject to any disclaimer, the term of this patent is extended or adjusted under 35 U.S.C. 154(b) by 42 days.

This patent is subject to a terminal disclaimer.

(21) Appl. No.: 14/171,273

(22) Filed: Feb. 3, 2014

(65) Prior Publication Data
US 2014/0221658 A1 Aug. 7, 2014

Related U.S. Application Data

(62) Division of application No. 11/562,903, filed on Nov. 22, 2006, now Pat. No. 8,642,278.

(60) Provisional application No. 60/738,776, filed on Nov. 22, 2005.

(51) Int. Cl.
| | |
|---|---|
| *C07C 279/06* | (2006.01) |
| *C07C 335/32* | (2006.01) |
| *C07C 323/45* | (2006.01) |
| *C07D 233/30* | (2006.01) |
| *C07D 233/84* | (2006.01) |
| *C07D 235/08* | (2006.01) |
| *C07D 249/14* | (2006.01) |
| *C07D 249/12* | (2006.01) |
| *C07D 277/42* | (2006.01) |
| *C07D 277/40* | (2006.01) |
| *C07D 317/56* | (2006.01) |
| *C07D 215/12* | (2006.01) |
| *C07D 213/53* | (2006.01) |
| *C07D 235/28* | (2006.01) |
| *C07D 317/58* | (2006.01) |

(52) U.S. Cl.
CPC .......... *C07C 323/45* (2013.01); *C07C 279/06* (2013.01); *C07C 335/32* (2013.01); *C07D 213/53* (2013.01); *C07D 215/12* (2013.01); *C07D 233/30* (2013.01); *C07D 233/84* (2013.01); *C07D 235/28* (2013.01); *C07D 249/12* (2013.01); *C07D 249/14* (2013.01); *C07D 277/40* (2013.01); *C07D 277/42* (2013.01); *C07D 317/56* (2013.01); *C07D 317/58* (2013.01)

(58) Field of Classification Search
CPC ... C07C 279/06; C07C 335/32; C07C 323/45; C07D 233/30; C07D 233/84; C07D 235/08; C07D 249/14; C07D 249/12; C07D 277/42; C07D 277/40; C07D 317/56; C07D 317/58; C07D 215/12; C07D 213/53

See application file for complete search history.

(56) References Cited

U.S. PATENT DOCUMENTS

| | | | |
|---|---|---|---|
| 3,258,325 A | 6/1966 | Lawlor et al. | |
| 3,269,901 A | 8/1966 | Schnell et al. | |
| 3,313,813 A | 4/1967 | Cragoe | |
| 3,513,197 A * | 5/1970 | Daum | C07C 335/32 504/155 |
| 6,093,728 A | 7/2000 | McMahon et al. | |
| 6,114,335 A | 9/2000 | Buerger et al. | |
| 6,521,407 B1 | 2/2003 | Warenius et al. | |
| 6,841,553 B2 * | 1/2005 | Gerritsma et al. | 514/260.1 |
| 7,855,228 B2 * | 12/2010 | Gitai | A61K 31/17 514/508 |
| 8,642,278 B2 * | 2/2014 | Sebti | C07C 279/06 435/375 |
| 2006/0241185 A1 | 10/2006 | Gitai et al. | |

FOREIGN PATENT DOCUMENTS

| | | |
|---|---|---|
| DE | 1122053 | 1/1962 |
| DE | 19641692 | 4/1998 |
| FR | 1563612 | 4/1969 |

(Continued)

OTHER PUBLICATIONS

Southan et al., British Journal of Pharmacology 1995, 114, 510-516.*
Patani et al., Chem. Rev. 1996, 96, 3147-3176.*
Levy et al., caplus an 1940:4626 (1940).*
Bacon et al., caplus an 1963:53289.*
Nishimura et al., caplus an 1965:15248, 1965.*
U.S. Appl. No. 11/350,966, filed Feb. 8, 2006, Gitai, et al.
U.S. Appl. No. 60/652,084, filed Feb. 10, 2005, Gitai, et al.

(Continued)

*Primary Examiner* — Sun Jae Yoo
(74) *Attorney, Agent, or Firm* — Fish & Richardson P.C.

(57) ABSTRACT

The disclosed modulators of Rb:Raf-1 interactions are potent, selective disruptors of Rb:Raf-1 binding, with $IC_{50}$ values ranging from 80 nM to 500 nM. Further, these compounds are surprisingly effective in inhibiting a wide variety of cancer cells, including osteosarcoma, epithelial lung carcinoma, non-small cell lung carcinoma, three different pancreatic cancer cell lines, two different glioblastoma cell lines, metastatic breast cancer, melanoma, and prostate cancer. Moreover, the disclosed compounds effectively disrupt angiogenesis and significantly inhibited tumors in nude mice derived from human epithelial lung carcinoma tumors. Accordingly, the disclosed compounds, pharmaceutical compositions comprising the compounds, methods of inhibiting cell proliferation, methods of treating subjects with cancer, and methods of preparing the disclosed compounds are provided.

23 Claims, 19 Drawing Sheets

(56) References Cited

FOREIGN PATENT DOCUMENTS

| | | |
|---|---|---|
| GB | 936766 | 9/1963 |
| GB | 960084 | 6/1964 |
| GB | 973882 | 10/1964 |
| GB | 1015011 | 12/1965 |
| GB | 1551224 * | 8/1979 |
| JP | 44002804 | 2/1969 |
| WO | 2006/122546 | 11/2006 |
| WO | 2007/062222 | 5/2007 |
| WO | 2008/026757 | 3/2008 |

OTHER PUBLICATIONS

Alavi A, et al. (2003) Role of Raf in vascular protection from distinct apoptotic stimuli. *Science* 301(5629), 94-96.
Anonymous, SciFinder Search Results, 58 hits, Aug. 27, 2009, 12 pages.
Anonymous, STN Search Results, 99 compound hits; 45 reference hits; Aug. 27, 2009, 75 pages.
Arkin MR, Wells JA. (2004) Small-molecule inhibitors of protein-protein interactions: progressing towards the dream. *Nature Reviews Drug Discovery* 3(4), 301-317.
Bagchi S, Weinmann R, Raychaudhuri P. (1991) The retinoblastoma protein copurifies with E2F-I, an E1A-regulated inhibitor of the transcription factor E2F. *Cell* 65(6):1073-82.
Beijersbergen RL, Bernards R. (1996) Cell cycle regulation by the retinoblastoma family of growth inhibitory proteins. [Review]. *Biochim Biophys Acta* 1287(2-3):103-20.
Bhargava et al., "N-Benzothiazol-2-yl-N'- Benzyl Guanidine Analogues," The Indian Journal of Pharmacy, 33(2):36-37, 1971.
Chau BN, Wang JY. (2003) Coordinated regulation of life and death by RB. *Nat Rev Cancer* 3(2):130-8.
Chawla et al., CRIPS, 5(1):9-12 (2004).
Chellappan S, Kraus VB, Kroger B, et al. (1992) Adenovirus E1A, simian virus 40 tumor antigen, and human papillomavirus E7 protein share the capacity to disrupt the interaction between transcription factor E2F and the retinoblastoma gene product. *Proc Natl Acad Sci USA* 89:4549-53.
Chellappan SP, Hiebert S, Mudryj M, Horowitz JM, Nevins JR. (1991) The E2F transcription factor is a cellular target for the RB protein. Cell 65(6):1053-61.
Chittenden T, M. Ld, JR Kwg. (1991) RB associates with an E2F-like, sequence-specific DNA-binding protein. *Cold Spring Harb Symp Quant Biol* 56:187-95.
Classon M, Dyson N. (2001) p107 and p130: versatile proteins with interesting pockets. *Exp Cell Res* 264(1):135-47.
Classon M, et al. (2000) Combinatorial roles for pRB, p107, and p130 in E2F-mediated cell cycle control. *Proc Natl Acad Sci U S A* 97(20):10820-5.
Cobrinik D. (2005) Pocket proteins and cell cycle control. *Oncogene* 24(17), 2796-2809.
Communication from the International Seaching Authority relating to the results of the Partial International Search for App. Ser. No. PCT/US2009/055509 mailed Mar. 9, 2010, 5 pages.
Costa et al., "Structural Requirements for Bretylium and Guanethidine-like Activity in a Series of Guanidine Derivatives," Life Sciences, 1(3):75-80, 1962.
Dasgupta P, Chellappan S. (2006) Nicotine-mediated cell proliferation and angiogenesis: New twists to an old story. *Cell Cycle* in press.
Dasgupta P, et al. (2004) Disruption of the Rb-Raf-1 interaction inhibits tumor growth and angiogenesis. *Mol Cell Biol* 24(21):9527-41.
Dasgupta P, et al. (2004) Direct binding of apoptosis signal-regulating kinase 1 to retinoblastoma protein: novel links between apoptotic signaling and cell cycle machinery. *J Biol Chem* 279(37):38762-9.
Dasgupta, P, et al. (2006) Nicotine induces cell proliferation by beta-arrestin-mediated activation of Src and Rb:Raf-1 pathways. *Journal of Clinical Investigation* 116, 2208-2217.

De Bruin A, et al. (2003) Identification and characterization of E2F7, a novel mammalian E2F family member capable of blocking cellular proliferation. *J Biol Chem* 278(43):42041-9.
Degregori J, et al. (1995) R. E2F-1 accumulation bypasses a G1 arrest resulting from the inhibition of G1 cyclin-dependent kinase activity. *Genes Dev* 9(23):2873-87.
Degregori J, et al. (1997) Distinct roles for E2F proteins in cell growth control and apoptosis. *Proc Natl Acad Sci U S A* 94(14):7245-50.
Derossi D, et al. (1994) The third helix of the Antennapedia homeodomain translocates through biological membranes. *J Biol Chem* 269(14):10444-50.
Derossi D, et al. (1998) Trojan peptides: the penetratin system for intracellular delivery. Trends Cell Biol 8(2):84-7.
Di Stefano L, Jensen MR, Helin K. (2003) E2F7, a novel E2F featuring DP-independent repression of a subset of E2F-regulated genes. *Embo J* 22(23):6289-98.
Dynamit Nobel A.-G., (1979) *Chemiker-Zeitung* 103 (1), 9-17.
Dyson N, Guida P, McCall C, E. H. (1992) Adenovirus E1A makes two distinct contacts with the retinoblastoma protein. *J Virol* 66(7):4606-11.
Dyson N, Howley PM, Munger K, Harlow E. (1989) The human papilloma virus-16 E7 oncoprotein is able to bind to the retinoblastoma gene product. *Science* 243(4893):934-7.
El-Hewehi, Z (1962) Reaction products of chlorinated benzyl chloride and their applicability as pest-controlling agents. *Journal fuer Praktische Chemie* (Leipzig) 16, 201-6 CODEN: JPCEAO; ISSN: 0021-8383.
El-Hewehi, Z (1962) Reaction products of chlorinated benzyl chloride and their applicability as pest-controlling agents. *Journal fuer Praktische Chemie* (Leipzig) 16, 201-6 CODEN: JPCEAO; ISSN: 0021-8383 (English language translation, and translator's certificate).
Englaender, VF, et al. (1979). "Chlorierung von Xylolen and Folgeprodukte, II. Umsetzungen der Chlorierunsprodukte" Chemiker-Zeitung, 103(1):9-17. (English language abstract included).
Gitai et al., caplus 2006;1124446, 'Antibiotics targeting MreB,' 1 page.
Gitai et al., U.S. Appl. No. 60/625,084; "Antibiotics Targeting MREB," filed Nov. 30, 2009, 74 pages.
Guisado, O, et al. (2002) A novel, facile methodology for the synthesis of N,N'-bis(tert-butoxycarbonyl)-protected guanidines using polymer-supported carbodiimide. *Tetrahedron Letters* 43, 7105-7109.
Hakem R, Mak TW. (2001) Animal models of tumor-suppressor genes. *Annu Rev Genet* 35:209-41.
Harbour JW, Dean DC. (2000) (Rb function in cell-cycle regulation and apoptosis. *Nat Cell Biol* 2(4):E65-7.
Harbour JW, et al. (1999) Cdk phosphorylation triggers sequential intramolecular interactions that progressiively block Rb functions as cells move through G1. *Cell* 98(6):859-69.
Harbour, JW, Dean, DC. (2000) The Rb/E2F pathway: expanding roles and emerging paradigms. *Genes & Development* 14, 2393-2409.
Hood JD, Cheresh DA. (2002) Targeted delivery of mutant Raf kinase to neovessels causes tumor regression. *Cold Spring Harbor Symposium on Quantitative Biology* 67, 285-291.
International Search Report and Written Opinion of the International Searching Authority for App. Ser. No. PCT/US2009/055509, mailed May 21, 2010, 21 pages.
Ishida S, et al. (2001) Role for E2F in control of both DNA replication and mitotic functions as revealed from DNA microarray analysis. *Mol Cell Biol* 21(14):4684-99.
Johnson DG, et al. (1993) Expression of transcription factor E2F1 induces quiescent cells to enter S phase. *Nature* 365:349-52.
Johnson DG, Schneider-Broussard R. (1998) Role of E2F in cell cycle control and cancer. *Front Biosci* 3:d447-8.
Kametani et al., Bulletin of Chemical Society of Japan, 33:1678-1680 (1960).
Kasid, U. (2001) Raf-1 protein kinase, signal transduction, and targeted intervention of radiation response. *Experimental Biology and Medicine* 226, 624-625.

(56) References Cited

OTHER PUBLICATIONS

Kato J, et al. (1993) Direct binding of cyclin D to the retinoblastoma gene product (pRb) and pRb phosphorylation by the cyclin D-dependent kinase CDK4. *Genes Dev* 7:331-42.

Knudsen ES, Wang JY. (1997) Dual mechanisms for the inhibition of E2F binding to RB by cyclin-dependent kinase-mediated RB phosphorylation. *Molecular and Cellular Biology* 17(10), 5771-5783.

Knudsen ES, Wang JY. (1996) Differential regulation of retinoblastoma protein function by specific Cdk phosphorylation sites. *Journal of Biological Chemistry* 271(14), 8313-8320.

Lam EW, La TN. (1994) DP and E2F proteins: coordinating transcription with cell cycle progression. [Review]. *Curr Opin Cell Biol* 6(6):859-66.

Lee JO, Russo AA, Pavletich NP. (1998) Structure of the retinoblastoma tumour-suppressor pocket domain bound to a peptide from HPV E7. *Nature* 391(6670):859-65.

Maccioni E, al. et al (2003) An investigation of the biological effect of structural modifications of isothiosemicarbazones and their cyclic analogues. *Farmaco* 58: 591-959.

Macleod K. (2000) Tumor suppressor genes. *Curr Opin Genet Dev* 10(1):81-93.

Miel, H, Rault, S. (1997) Total deprotection of N,N'-bis (tert-butoxycarbonyl) guanidines using SnCl4. *Tetrahedron Letters* 38, 7865-7866.

Molecular cancer, http://www.molecular-cancer.com/content/2/1/27 (2003).

Morris EJ, Dyson NJ. (2001) Retinoblastoma protein partners. *Adv Cancer Res* ;82:1-54.

Muller H, Bracken AP, Vernell R, et al. (2001) E2Fs regulate the expression of genes involved in differentiation, development, proliferation, and apoptosis. *Genes Dev* 15(3):267-85.

Muller H, Helin K. (2000) The E2F transcription factors: key regulators of cell proliferation. *Biochim Biophys Acta* 1470(1):M1-M12.

Musgrave, AJ, et al. (1954). Screening new compounds as insecticides. A progress report. *85th Annual Report of the Entomological Society of Ontario 1954*, pp. 16-24.

Musgrave, AJ, Kukovica, I. (1955) Screening new compounds as insecticides; a progress report *85th Ann. Rept. Entomol. Soc. Ontario* Volume Date 1954 15-24.

Nevins JR. (1993) Disruption of cell-cycle control by viral oncoproteins. [Review]. *Biochemical Society Transactions* 21(4):935-8.

Nevins JR. (1994) Cell cycle targets of the Dna tumor viruses. *Current Opinion in Genetics & Development* 4(1):130-4.

Nevins Jr. (1992) E2F: a link between the Rb tumor suppressor protein and viral oncoproteins. *Science* 258(5081), 424-429.

Nevins, JR. (2001). The Rb/E2F pathway and cancer. *Human Molecular Genetics*, 10(7):699-703.

Newman et al., DDT, 8:898-905 (2003).

Newman MS, et al. (1947) New Compounds as Plant Growth Regulators. *JACS* 69: 718-723.

Norbury, C., et al. (1992). Animal cell cycles and their control. *Ann. Rev. Biochem.*, 61:441- 470.

Paggi, MG, et al. (1996). Retinoblastoma protein family in cell cycle and cancer: a review. *Journal of Cellular Biochemistry*, 62:418-430.

Park et al., "Synthesis and Antibacterial Activity of 7.beta.-[2-(Substituted Benzylthio) Alkanamido] Cephalosporins," J. Pharmaceutical Society of Korea—Yakhak Hoeji, 32(4):222-229, 1988 (with English abstract).

Prives, C., et al. (1999). The p53 pathway. *Journal of Pathology*, 187:112-126.

Radioprotectant, http://ttc.nci.nih.gov/opportunities/opportunity.php?opp_id=1984 (2012).

Reddy, GPV (1994). Cell cycle: regulatory events in $G_1 \rightarrow S$ transition of mammalian cells. *Journal of Cellular Biochemistry*, 54:379-386.

Reed, SI (1997). Control of the $G_1$/S transition. *Cancer Surveys*, 29:7-23.

Ren, B, et al. (2002).E2F integrates cell cycle progression with DNA repair, replication, and $G_2$/M checkpoints. *Genes & Development*, 16:245-256.

Rini, BI (2006). Expert opinion Sorafenib. *Expert Opin. Pharmacother.*, 7(4)::453-461.

Rudin, CM, et al. (2001). Phase I trial of ISIS 5132, an antisense oligonucleotide inhibitor of c-raf-1, administered by 24-hour weekly infusion to patients with advanced cancer. *Clinical Cancer Research*, 7:1214-1220.

Sager R. (1992)Tumor suppressor genes in the cell cycle. *Curr Opin Cell Biol* 4155-160.

Sager R. (1989) Tumor suppressor genes: The puzzle and the promise. *Science* 246:1406-12.

Sherr CJ, McCormick F. (2002) The RB and p53 pathways in cancer. *Cancer Cell* (2):103-12.

Sherr CJ, Roberts JM. (1995) Inhibitors of mammalian G1 cyclin-dependent kinases. [Review]. *Genes & Development* 9(10):1149-63.

Sherr CJ. (1995) Mammalian G1 cyclins and cell cycle progression. *Proc Assoc Am Physicians* 107(2):181-6.

Sherr CJ. (1994) the ins and outs of RB: Coupling gene expression to the cell cycle clock. *Trends Cell Biol* 4:15-8.

Sherr CJ. (2000) Cell cycle control and cancer. *Harvey Lect* 96:73-92.

Sherr, CJ, et al. (1995). Inhibitors of mammalian $G_1$ cyclin-dependent kinases. *Genes & Development*, 9:1149-1163.

Sherr, CJ, et al. (2002). The RB and p53 pathways in cancer. *Cancer Cell*, 2:103-112.

Slansky JE, Farnham PJ. (1996) Introduction to the E2F family: protein structure and gene regulation. [Review]. *Curr Top Microbiol Immunol* 208(1):1-30.

Stiegler P, Kasten M, Giordano A. (1998)The RB family of cell cycle regulatory factors. *J Cell Biochem Suppl* 31:30-6.

Supplementary European Search Report dated Aug. 30, 2011 for European Appln. No. 06838400.7 (7 pgs.).

Tait A and Di Bella M (1990) Reactivity Toward Cysteine of Antimicrobial Carbamimidothioic acid phenylalkylesters salts *Bollettino Chimico Farmaceutico* 248-50.

Tait A, et al (1990) Carbamimidothioic acid phenylmethyl ester salts and their N,N'-Tetramethyl derivatives as possible antimicrobial agents. *Il Farmaco* 45(6), 617-630.

Takahashi Y, Rayman JB, Dynlacht BD. (2000) Analysis of promoter binding by the E2F and pRb families in vivo: distinct E2F proteins mediate activation and repression. *Genes Dev* 14:804-16.

Taya Y, Yasuda H, Kamijo M, et al. (1989) In vitro phosphorylation of the tumor suppressor gene RBprotein by mitosis-specific histone H1 kinase. *Biochem Biophys Res Commun* 164(1):580-6.

Taya Y. (1997) RB kinases and RB-binding proteins: new points of view. [Review] [50 refs]. *Trends Biochem Sci* 22(1):14-7.

Taylor, WR, et al. (2001). Regulation of the G2/M transition by p53. *Oncogene*, 20:1803-1815.

Thompson, HE, et al. (1946). New growth-regulating compounds. 1. Summary of growth-inhibitory activities of some organic compounds as determined by three tests. *Botanical Gazette*, pp. 476-507.

Tonini, T, et al. (2002). Interview with the retinoblastoma family members: Do they help each other? *Journal of Cellular Physiology*, 192:138-150.

Trimarchi JM, Lees JA. (2002) Transcription: Sibling rivalry in the E2F family. *Nat Rev Mol Cell Bio* 3(1):11-20.

Tulecki et al., Annales Pharmaceutici, 13:139-152 (1978).

Tulecki et al., caplus an 1980:22187.

University of South Florida, PCT International Search Report & Written Opinion dated Nov. 6, 2007 of PCT/US/45410 filed Nov. 22, 2006.

Walchshofer et al., "Recherche des paramètres structuraux influençant l' activité anthelminthique de dérivés thiazoliques," European Journal of Medicinal Chemistry, 21(1):59-64, 1986 (with English summary).

(56) References Cited

OTHER PUBLICATIONS

Wang, S, et al. (1998). Raf-1 physically interacts with Rb and regulates its function: a link between mitogenic signaling and cell cycle regulation. *Molecular and Cellular Biology,* 18(12):7487-7498.
Wang, S, et al. (1999). Regulation of Rb and E2F by signal transduction cascades: divergent effects of JNK1 and p38 kinases. *The EMBO Journal,* 18(6):1559-1570.
Weinberg RA.(1996) E2F and cell proliferation: a world turned upside down. [Review]. *Cell*;85(4):457-9.
Weinberg, RA (1995). The retinoblastoma protein and cell cycle control. *Cell,* 81:323-330.
Welch, PJ, et al. (1993). A C-terminal protein-binding domain in the retinoblastoma protein regulates nuclear c-Abl tyrosine kinase in the cell cycle. *Cell,* 75:779-790.
Welch, PJ, et al. (1995). Disruption of retinoblastoma protein function by coexpression of its C pocket fragment. *Genes & Development,* 9:31-46.
Wilhelm S, et al. (2006) Discovery and development of sorafenib: a multikinase inhibitor for treating cancer. *Nature Reviews Drug Discovery* 5(10), 8358-8344.
Wilhelm, SM, et al. (2004) BAY 43/9006 exhibits broad spectrum oral antitumor activity and targets the RAF/MEK/ERK pathway and receptor tyrosine kinases involved in tumor progression and angiogenesis. *Cancer Research* 64, 7099-7109.
Yin H, Hamilton AD. (2005) Strategies for targeting protein-protein interactions with synthetic agents. *Angewandte Chemie International Ed. in English* 44(27), 4130-4163.
Yong, YF, et al. (1997) Facile and efficient guanylation of amines using thioureas and Mukaiyama's reagent. *Journal of Organic Chemistry* 62, 1540-1542.

\* cited by examiner

| Cell Line/ Origin | Mutations | % Inhibition (BrdU) RRD 251 20µM |
|---|---|---|
| H1650/ NSCLC | EGFR mut (Iressa sensitive) | 90% |
| Aspc1/ Pancreatic | p16 (2bp deletion) Ras mut, p53 mut | 65% |
| PANC1/Pancreatic | p16 (HD),Ras mut p53 mut, AKT2 amplification | 53% |
| CAPAN2/Pancreatic | P16 mut, Ras, mut | 51% |
| U87MG/ Glioma | p16 null, PTEN null | 54% |
| U251MG/ Glioma | p16 null, PTEN null | 35% |
| U2-OS/ Osteosarcoma | Mut p16 WT Rb | 60% |
| Saos-2/ Osteosarcoma | WT p16, Rb (-) p53 (-) | 10% |
| MDA-MB-231/ Breast | K-Ras mut EGFR (OE) | 56% |
| A549/NSCLC | K-Ras/ WT EGFR | 60% |
| A549-shNH1 | Non-Homologous | 46% |
| A549-sh-6 | Rb silenced | 2% |
| A549-sh-8 | Rb silenced | 1% |
| A375/Melanoma | V600E | 58% |
| LNCap/Prostate | PTEN mut, K-Ras mut | 86% |
| PC3/Prostate | PTEN mut, K-Ras mut | 35% |

FIGURE 3D

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: PCR primer

<400> SEQUENCE: 1
ggcctcacag cgactctaag a                                             21

<210> SEQ ID NO 2
<211> LENGTH: 18
<212> TYPE: DNA
<213> ORGANISM: Artificial Sequence
<220> FEATURE:
<223> OTHER INFORMATION: PCR primer

<400> SEQUENCE: 2
ctcggactca ccacaagc                                                 18

<210> SEQ ID NO 3
<211> LENGTH: 19
<212> TYPE: DNA
<213> ORGANISM: Artificial Sequence
<220> FEATURE:
<223> OTHER INFORMATION: PCR primers

<400> SEQUENCE: 3
gacggaggca ggccaagtg                                                19
```

INHIBITION OF CELL PROLIFERATION

CROSS REFERENCE TO RELATED APPLICATIONS

This application is a divisional of U.S. application Ser. No. 11/562,903, filed Nov. 22, 2006, which claims the benefit of U.S. Provisional Appl. Ser. No. 60/738,776, filed Nov. 22, 2005. The entire disclosure each of the prior applications is incorporated herein by reference.

GOVERNMENT SUPPORT

This invention was made with government support under 5R01CA063136-14 awarded by the National Cancer Institute. The government has certain rights in the invention.

TECHNICAL FIELD

This application relates to compounds, pharmaceutical compositions, and methods for modulating the Rb:Raf-1 interaction in vitro or in vivo, and more particularly to treatment of disorders modulated by the Rb:Raf-1 interaction, for example, proliferation disorders such as cancer.

BACKGROUND

The inactivation of the retinoblastoma tumor suppressor protein Rb by cell cycle regulatory kinases is disrupted in almost all cancers. In normal cells, inactivation of Rb is necessary for the G1 to S phase progression of the cell cycle. Rb controls entry into the S phase by repressing the transcriptional activity of the E2F family of transcription factors, especially E2Fs 1, 2, and 3. Rb is inactivated through multiple phosphorylation events mediated by kinases associated with D and E type cyclins in the G1 phase of the cell cycle. It was found that the signaling kinase Raf-1 initiates the phosphorylation events; Raf-1 signaling kinase is known to play a role in promoting cancer, and studies have shown that Rb:Raf-1 binding facilitates cell proliferation. It has also been found that the Rb:Raf-1 interaction is elevated in human tumors compared to adjacent normal tissue in 80% of samples examined. Because Raf-1 is persistently activated in many tumors, a few attempts have been made to selectively inhibit tumors by modulating Rb and/or Raf-1 activity with Raf-1 antisense oligonucleotides, the multikinase inhibitor Sorafenib, and a peptide fragment of Raf-1 coupled to a carrier peptide. However, there is still a need for effective modulators of the Rb:Raf-1 interaction.

SUMMARY

Applicants have discovered modulators of Rb:Raf-1 interactions that are surprisingly effective in inhibiting the tumor growth and survival of a wide variety of cancer cells. For example, certain disclosed compounds are potent, selective disruptors of Rb:Raf-1 binding, with $IC_{50}$ values ranging from 80 nM to 500 nM (Examples 5-8). Also, the disclosed compounds are surprisingly effective in inhibiting the tumor growth and survival of a wide variety of cancer cells, including osteosarcoma (Example 9), epithelial lung carcinoma (Example 10), non-small cell lung carcinoma (Example 11), three different pancreatic cancer cell lines (Example 12), two different glioblastoma cell lines (Example 13), metastatic breast cancer (Example 14), melanoma (Example 15), and prostate cancer (Example 16). Moreover, the disclosed compounds effectively disrupt angiogenesis (Example 18), significantly inhibited anchorage independent tumor growth (Example 19) and significantly inhibited the growth of human epithelial lung carcinoma in nude mice (Example 20). Accordingly, compounds, pharmaceutical compositions comprising the compounds, methods of inhibiting cell proliferation, methods of treating subjects with cancer, and methods of preparing the disclosed compounds are provided herein.

The compound is represented by structural formula Ia:

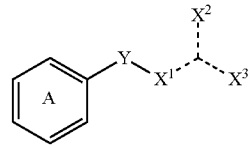

and pharmaceutically acceptable salts and solvates thereof.

In the compound represented by structural formula Ia, each dashed line (- - -) represents a single bond, or one dashed line (- - -) is a double bond. Typically, one dashed line is a double bond and the other dashed lines are single bonds.

In the compound represented by structural formula Ia, Ring A is optionally substituted. Zero, one, or two of the ring atoms in Ring A are N. Further, Ring A is fused with zero, one, or two optionally substituted 3-15 membered monocyclic or polycyclic rings selected from the group consisting of aryl, heteroaryl, heterocyclyl, and cycloaliphatic. For example, in some embodiments, the ring represented by Ring A, together with any rings to which it can be fused, is an optionally substituted phenyl, biphenyl, naphthyl, pyrenyl, anthracyl, 9,10-dihydroanthracyl, fluorenyl, pyridyl, pyrimidyl, pyrazinyl, triazinyl, quinolinyl, isoquinolinyl, quinazolinyl, napthyridyl, pyridopyrimidyl, benzothienyl, benzothiazolyl, benzoisothiazolyl, thienopyridyl, thiazolopyridyl, isothiazolopyridyl, benzofuranyl, benzooxazolyl, benzoisooxazolyl, furanopyridyl, oxazolopyridyl, isooxazolopyridyl, indolyl, isoindolyl, benzimidazolyl, benzopyrazolyl, pyrrolopyridyl, isopyrrolopyridyl, imidazopyridyl, or pyrazolopyridyl group. In certain embodiments, the ring represented by Ring A, together with any rings to which it can be fused, is an optionally substituted phenyl, naphthyl, anthracyl, fluorenyl, 9,10-dihydroanthracyl, pyridyl, pyrimidyl, pyrazinyl, triazinyl, quinolinyl, isoquinolinyl, quinazolinyl, or napthyridyl group. In particular embodiments, the ring represented by Ring A, together with any rings to which it can be fused, is an optionally substituted naphthyl, pyridyl, quinolinyl, or isoquinolinyl group, or a substituted phenyl group.

In some embodiments, one, two or three substitutable carbons in the ring represented by Ring A can be substituted with —F, —Cl, —Br, —I, —CN, —$NO_2$, $C_{1-6}$ alkyl, $C_{1-6}$ alkoxy, —$CF_3$, or $C_{1-6}$ haloalkoxy, or two substitutable carbons in the ring represented by Ring A are linked with $C_{1-2}$ alkylenedioxy. In some embodiments, at least one ring atom of Ring A adjacent to the point of attachment of Ring A to the rest of the compound is unsubstituted, for example, when Ring A is phenyl and Y is at the 1-position, either the 2 or the 6 position is unsubstituted.

In some embodiments, Ring A can be a six-membered ring that is monsubstituted at its 2, 3, or 4 positions or disubstituted at its 2,3, 2,4, 2,5 or 3,4 positions with substituents independently selected from the group consisting of —F, —Cl, —Br, —NO$_2$, C$_{1-6}$ alkyl, —CF$_3$, and methylenedioxy, where the 1 position is the point of attachment of Ring A to the rest of the compound, e.g., the point of attachment of Ring A to Y. In some embodiments, Ring A is a phenyl independently disubstituted with —Br, —Cl, —F, or —CF$_3$ at the 2,3, 2,4, or 2,5 positions of Ring A, where the 1 position is the point of attachment of Ring A to the rest of the compound.

In the compound represented by structural formula Ia, Y is an optionally substituted C$_{1-3}$ alkylene or C$_{1-3}$ alkenylene linking group. In some embodiments, Y can be optionally substituted with —OH, C$_{1-6}$ alkyl, C$_{1-6}$ alkoxy, C$_{1-6}$ haloalkyl, C$_{1-6}$ haloalkoxy, or C$_{1-6}$ aralkyl, =O, or =S. Generally, Y is optionally substituted with —OH, C$_{1-6}$ alkyl, C$_{1-6}$ alkoxy, C$_{1-6}$ aralkyl, =O, or =S. Preferably, Y is unsubstituted or substituted with C$_{1-3}$ alkyl. Typically, Y can be ethylene or methylene. In certain embodiments, Y is unsubstituted or substituted with C$_{1-3}$ alkyl. When a substituent, is bonded to Y, such a substituent may be bound to any carbon in Y. Typically, a substituent can be bonded to the carbon in Y adjacent to Ring A.

In the compound represented by structural formula Ia, X$^1$ is independently —O—, —S—, or optionally substituted —CH$_2$—, —CH=, —NH—, or —N=, and X$^2$ and X$^3$ are independently =S, or optionally substituted —NH$_2$, =NH, or —SH, or an optionally substituted 3-7 membered aryl, heteroaryl, heterocyclyl, or cycloaliphatic ring. Or, X$^2$ and X$^3$ are independently —S—, or optionally substituted —NH—, —N=, or =N—, and X$^2$ and X$^3$ are linked α, β, or γ through an optionally substituted alkyl, alkenyl, heteroalkyl, heteroalkenyl, heteroatom, aryl, heteroaryl, heterocyclyl, or cycloaliphatic linking group, thereby forming an optionally substituted heteroaryl or heterocyclyl ring. Or, X$^2$ is independently —S— or optionally substituted —NH—, —N=, or =N—, and X$^2$ is linked α, β, or γ to a carbon of Y through an optionally substituted alkyl, alkenyl, heteroalkyl, heteroalkenyl, or heteroatom linking group, thereby forming an optionally substituted heteroaryl or heterocyclyl ring, and wherein X$^3$ is optionally —H, and wherein X$^3$ is optionally —H. In some embodiments, X$^3$ is not —H.

Each substitutable carbon in structural formula Ia and the variables represented in structural formula Ia can be optionally substituted with a carbon substituent independently selected from the group consisting of —F, —Cl, —Br, —I, —CN, —NO$_2$, —R$^a$, —OR$^a$, —C(O)R$^a$, —OC(O)R$^a$, —C(O)OR$^a$, —SR$^a$, —C(S)R$^a$, —OC(S)R$^a$, —C(S)OR$^a$, —C(O)SR$^a$, —C(S)SR$^a$, —S(O)R$^a$, —SO$_2$R$^a$, —SO$_3$R$^a$, —OSO$_2$R$^a$, —OSO$_3$R$^a$, —PO$_2$R$^a$R$^b$, —OPO$_2$R$^a$R$^b$, —PO$_3$R$^a$R$^b$, —OPO$_3$R$^a$R$^b$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —NR$^a$SO$_2$R$^b$, —NR$^c$C(O)R$^a$, —NR$^c$C(O)OR$^a$, —NR$^c$C(O)N(R$^a$R$^b$), —C(NR$^c$)—N(R$^a$R$^b$), —NR$^d$—C(NR$^c$)—N(R$^a$R$^b$), —NR$^a$N(R$^a$R$^b$), —CR$^c$=CR$^a$R$^b$, —C≡CR$^a$, =O, =S, =CR$^a$R$^b$, =NR$^a$, =NOR$^a$, and =NNR$^a$, or two substitutable carbons can be linked with C$_{1-3}$alkylenedioxy. In some embodiments, each substitutable carbon can be optionally substituted with —F, —Cl, —Br, —I, —CN, —NO$_2$, —R$^a$, —OR$^a$, —C(O)R$^a$, —OC(O)R$^a$, —C(O)OR$^a$, —SR$^a$, —SO$_2$R$^a$, —SO$_3$R$^a$, —OSO$_2$R$^a$, —OSO$_3$R$^a$, —N(R$^a$R$^b$), —C(O)N(R$^a$R$^b$), —C(O)NR$^a$NR$^b$SO$_2$R$^c$, —C(O)NR$^a$SO$_2$R$^c$, —SO$_2$N(R$^a$R$^b$), —NR$^a$SO$_2$R$^b$, —NR$^c$C(O)R$^a$, —NR$^c$C(O)OR$^a$, =S, or =O, or two substitutable carbons can be linked with C$_{1-3}$alkylenedioxy.

Each substitutable nitrogen in structural formula Ia and the variables represented in structural formula Ia can optionally substituted with a nitrogen substituent independently selected from the group consisting of —CN, —NO$_2$, —R$^a$, —OR$^a$, —C(O)R$^a$, —C(O)R$^a$-aryl, —OC(O)R$^a$, —C(O)OR$^a$, —SR$^a$, —S(O)R$^a$, —SO$_2$R$^a$, —SO$_3$R$^a$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —NR$^a$SO$_2$R$^b$, —NR$^c$C(O)R$^a$, —NR$^c$C(O)OR$^a$, —NR$^c$C(O)N(R$^a$R$^b$), and oxygen to form an N-oxide. Further, each substitutable nitrogen in structural formula Ia and the variables represented in structural formula Ia can be optionally protonated or quaternary substituted to carry a positive charge, which can be balanced by a pharmaceutically acceptable counterion.

Substitutable carbons or nitrogens in structural formula Ia include the carbons in Ring A which are not bound to Y, or the nitrogens which replace one or two carbons in Ring A. Further, examples of substitutable carbons or nitrogens in the variables represented in structural formula Ia include, e.g., the carbons in linker Y, the carbons in X$^1$ when X$^1$ is —CH$_2$— or —CH=, the nitrogens in X$^1$ when X$^1$ is —NH— or —N=, the nitrogens when X$^2$ and X$^3$ are —NH$_2$, =NH, substitutable carbons in the 3-7 membered aryl, heteroaryl, heterocyclyl, or cycloaliphatic rings which can be selected for X$^2$ and X$^3$, and the like.

In the compound represented by structural formula Ia, each R$^a$-R$^d$ is independently —H, C$_{1-6}$alkyl, C$_{1-6}$alkoxy, C$_{1-6}$haloalkyl, C$_{1-6}$haloalkoxy, C$_{1-6}$ aralkyl, aryl, heteroaryl, heterocyclyl, or cycloaliphatic, or, —N(R$^a$R$^b$), taken together, is an optionally substituted heterocyclic group. In some embodiments, each R$^a$-R$^d$ is independently —H, C$_{1-6}$ alkyl, C$_{1-6}$ alkoxy, C$_{1-6}$ haloalkyl, C$_{1-6}$ haloalkoxy, C$_{1-6}$ aralkyl, aryl, heteroaryl, heterocyclyl, or cycloaliphatic. In some embodiments, each R$^a$-R$^d$ is independently —H or C$_{1-6}$ alkyl.

In the compound represented by structural formula Ia, one or more protecting groups may optionally protect one or more of X$^2$, X$^3$, each nitrogen substitutent, and each carbon substituent.

In some embodiments, the compound represented by structural formula Ia does not include benzyl N,N'-bis(tert-butoxycarbonyloxy)carbamimidothioate. In some embodiments, the compound represented by structural formula Ia is not benzyl carbamimidothioate.

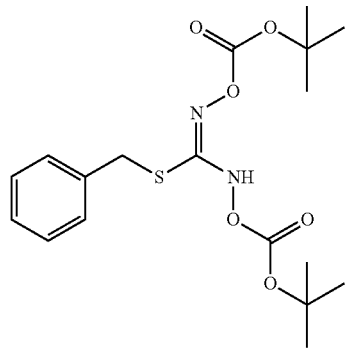

benzyl N, N'-bis(tert-butoxy carbonyloxy) carbamimidothioate

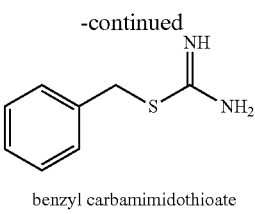

benzyl carbamimidothioate

In some embodiments, the compound represented by structural formula Ia does not include the 3,4,6-trichloro-2-nitrophenolate salt of 2,4-dichlorobenzyl carbamimidothioate or the 2,4-dinitrophenolate salt of (4-chloronaphthalen-1-yl)methyl carbamimidothioate:

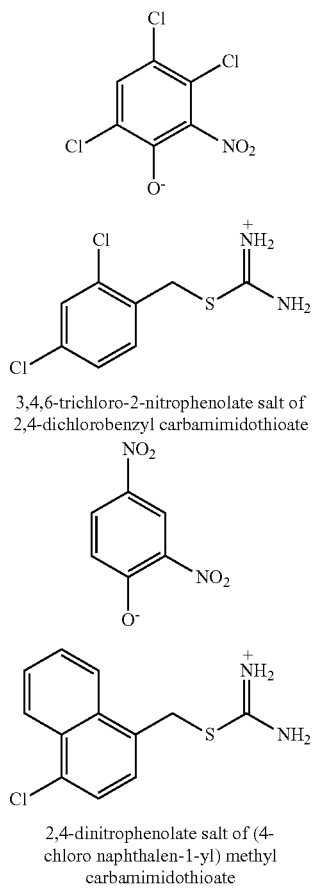

3,4,6-trichloro-2-nitrophenolate salt of 2,4-dichlorobenzyl carbamimidothioate 2,4-dinitrophenolate salt of (4-chloro naphthalen-1-yl) methyl carbamimidothioate In certain embodiments, the compound is not 2,4-dichlorobenzyl carbamimidothioate or (4-chloronaphthalen-1-yl) methyl carbamimidothioate. In particular embodiments, the compounds represented by structural formula Ia do not include 3,4,6-trichloro-2-nitrophenolate or 2,4-dinitrophenolate salts.

In some embodiments, Ring A and Y, taken together, are not an unsubstituted benzyl group. In certain embodiments, Ring A is not an unsubstituted phenyl group. In some embodiments, $X^1$, $X^2$, and $X^3$, taken together with the carbon atom between them are not an unsubstituted guanidinyl group. Likewise, in some embodiments, the second reagent is not unsubstituted guanidine. In some embodiments, $X^1$, $X^2$, and $X^3$, taken together with the carbon atom between them are not an unsubstituted thioureayl group where $X^1$ is S. In certain embodiments, $X^1$, $X^2$, and $X^3$, taken together with the carbon atom between them are not an unsubstituted thioureayl group. Likewise, in some embodiments, the second reagent is not unsubstituted thiourea. In some embodiments, $X^1$, $X^2$, and $X^3$, taken together with the carbon atom between them are not an unsubstituted ureayl group where $X^1$ is O. In certain embodiments, $X^1$, $X^2$, and $X^3$, taken together with the carbon atom between them are not an unsubstituted ureayl group. Likewise, in some embodiments, the second reagent is not unsubstituted urea.

In some embodiments, the compound is represented by structural formula Ib:

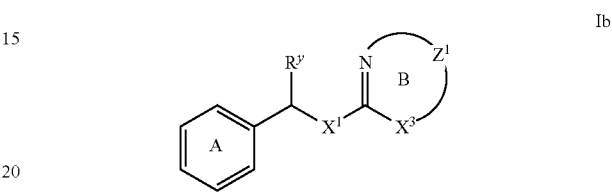

The variables in structural formula Ib can take any values as described for those variables herein. In some embodiments, in the compound represented by structural formula Ib, $R^y$ is —H, —OH, $C_{1-6}$ alkyl, $C_{1-6}$ alkoxy, $C_{1-6}$ haloalkyl, $C_{1-6}$ haloalkoxy, or $C_{1-6}$ aralkyl, or —$R^y$ is =O or =S. $X^1$ and $X^3$ are independently N or S. $Z^1$ is a heteroatom or a β- or γ-bonded alkyl, alkenyl, heteroalkyl, heteroalkenyl, aryl, heteroaryl, heterocyclyl, or cycloaliphatic linking group, whereby Ring B is a heterocyclyl or heteroaryl ring. Ring B is optionally substituted at any substitutable ring atom with halogen, —CN, —$NO_2$, —$R^a$, —$OR^a$, —$C(O)R^a$, —$OC(O)R^a$, —$C(O)OR^a$, —$SR^a$, —$SO_2R^a$, —$SO_3R^a$, —$OSO_2R^a$, —$OSO_3R^a$, —$N(R^aR^b)$, —$C(O)N(R^aR^b)$, —$SO_2N(R^aR^b)$, —$NR^aSO_2R^b$, —$NR^cC(O)R^a$, —$NR^cC(O)OR^a$, or =O.

In some embodiments, the compound is represented by structural formula Ic:

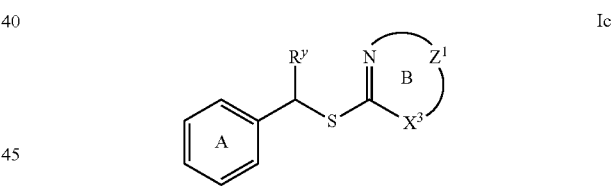

The variables in structural formula Ic can take any values as described for those variables herein. In some embodiments, in the compound represented by structural formula Ic, $Z^1$ is 1,2-phenylene, —$CH_2CH_2$—, —CH=CH—, or —N=$CH_2$—; and Ring B is optionally substituted at any substitutable ring atom with halogen, —CN, —$NO_2$, —$R^a$, —$OR^a$, —$N(R^aR^b)$, —$C(O)N(R^aR^b)$, —$NR^cC(O)R^a$, or =O. In some embodiments, $Z^1$ is —N=$CH_2$-optionally substituted with —$N(R^aR^b)$. In certain embodiments, the compound, e.g., represented by structural formula Ic, is selected from the group consisting of:

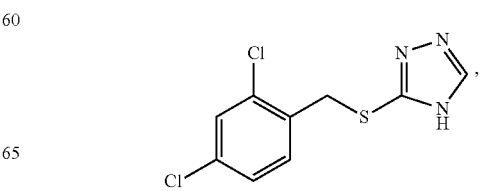

-continued

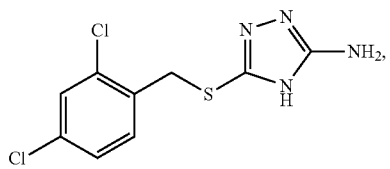

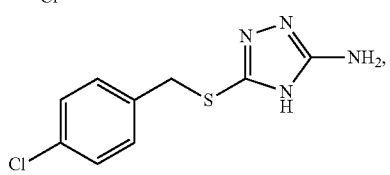

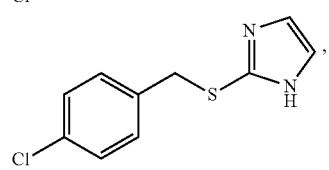

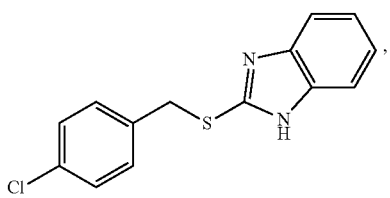

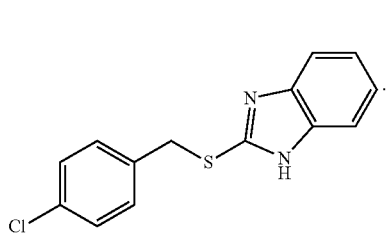 [SMILES: Clc1ccc(CSc2nc3ccccc3[nH]2)cc1]

In some embodiments, the compound is represented by structural formula Id:

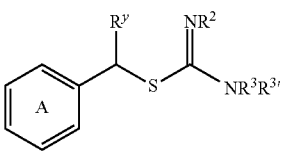

The variables in structural formula Id can take any values as described for those variables herein. In some embodiments, in the compound represented by structural formula Id, $R^3$, $R^{3'}$, $R^y$ and $R^2$ are independently —H, —OH, $C_{1-6}$ alkyl, $C_{1-6}$ alkoxy, $C_{1-6}$ haloalkyl, $C_{1-6}$ haloalkoxy, $C_{1-6}$ aralkyl, aryl, heteroaryl, heterocyclyl, or cycloaliphatic, or —$R^y$ is =O or =S. In some embodiments, $R^y$ is —H, $C_{1-6}$alkyl, $C_{1-6}$ aralkyl, or =O. In certain embodiments, the compound, e.g., represented by structural formula Id, is selected from the group consisting of:

In certain embodiments, the compound, e.g., represented by structural formula Id, is selected from the group consisting of:
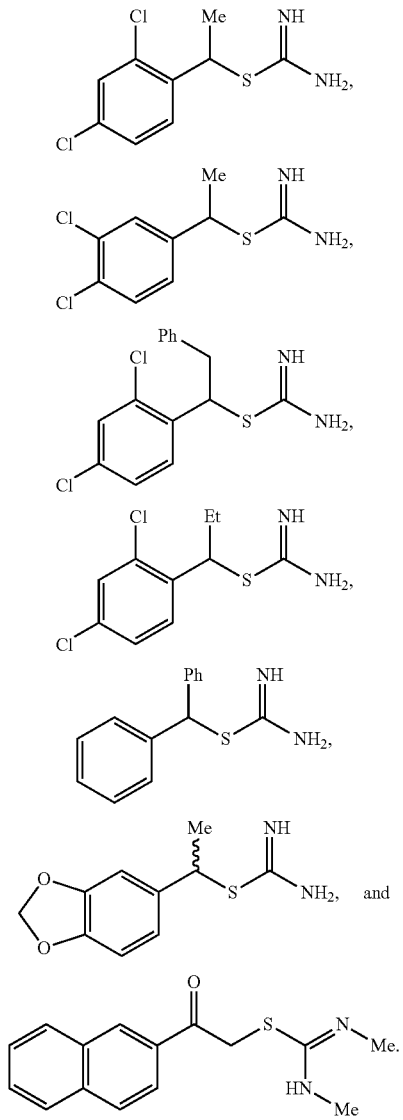
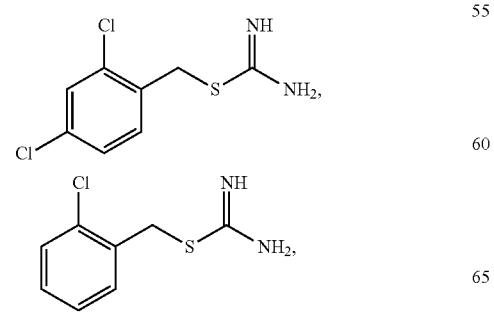
In certain embodiments, the compound, e.g., represented by structural formula Id, is selected from the group consisting of:
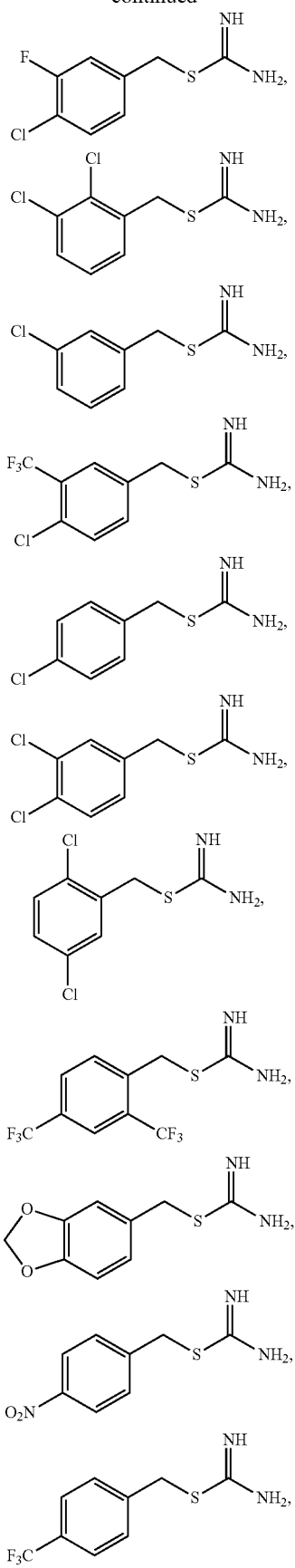

-continued

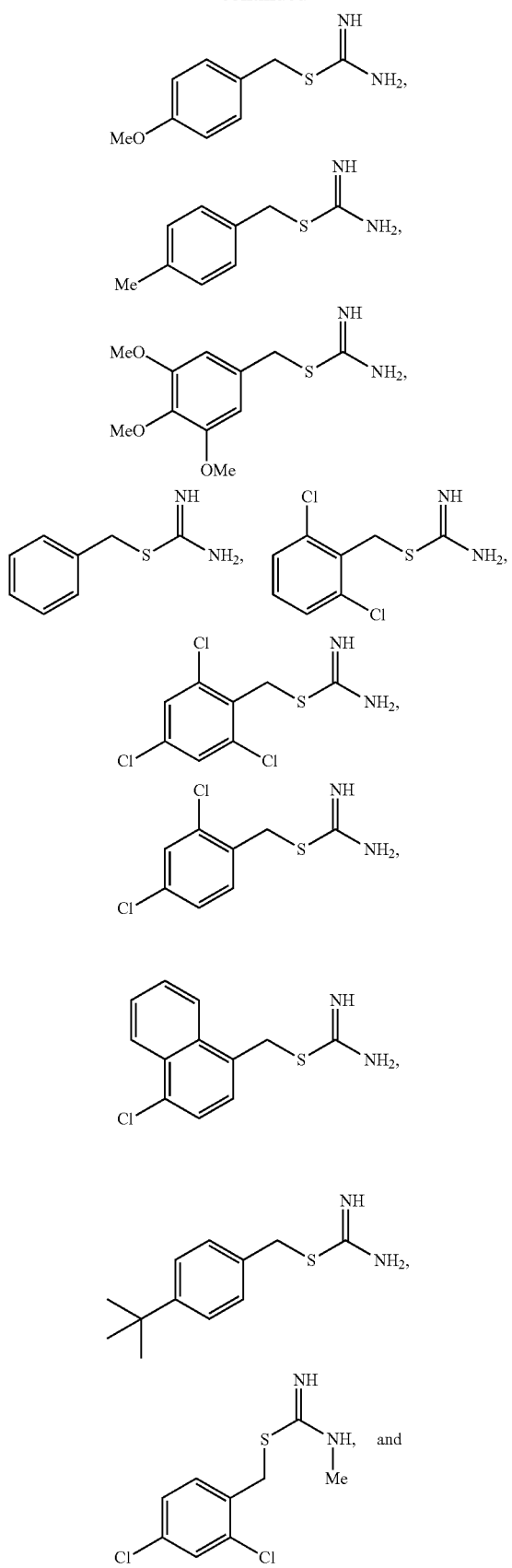

-continued

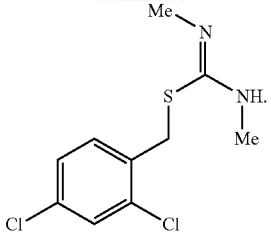

In some embodiments, the compound is represented by structural formula Ie:

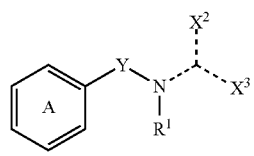

Ie

The variables in structural formula Ie can take any values as described for those variables herein. In some embodiments, in the compound represented by structural formula Ie, $R^1$ is —H, —OH, $C_{1-6}$ alkyl, $C_{1-6}$alkoxy, $C_{1-6}$haloalkyl, $C_{1-6}$haloalkoxy, $C_{1-6}$ aralkyl, aryl, heteroaryl, heterocyclyl, or cycloaliphatic, or —$R^1$ represents a lone pair of the nitrogen to which it is attached.

In some embodiments, the compound is represented by structural formula If:

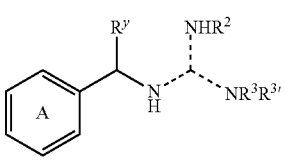

If

The variables in structural formula If can take any values as described for those variables herein. In some embodiments, in the compound represented by structural formula If, $R^3$, $R^{3\prime}$, $R^y$ and $R^2$ are independently —H, —OH, $C_{1-6}$alkyl, $C_{1-6}$alkoxy, $C_{1-6}$ haloalkyl, $C_{1-6}$haloalkoxy, $C_{1-6}$ aralkyl, aryl, heteroaryl, heterocyclyl, or cycloaliphatic, or —$R^y$ is =O or =S. In some embodiments, $R^y$ is —H, $C_{1-6}$alkyl, or $C_{1-6}$ aralkyl, or —$R^y$ is =O. In certain embodiments, the compound, e.g., represented by structural formula If, is selected from the group consisting of:

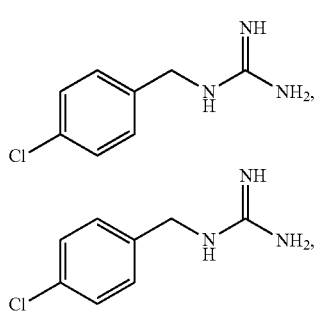

-continued

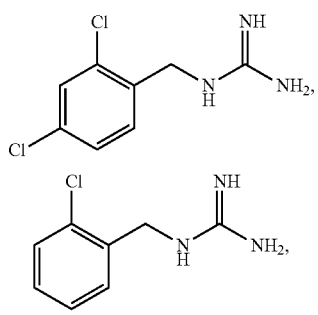

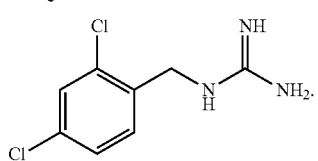

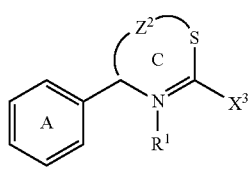

In some embodiments, the compound is represented by structural formula Ig:

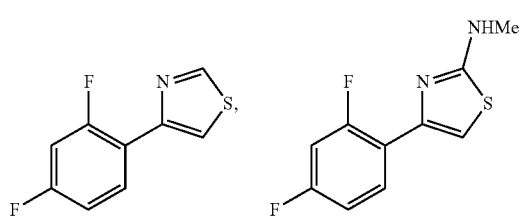

Ig

The variables in structural formula Ie can take any values as described for those variables herein. In some embodiments, in the compound represented by structural formula Ie, $X^3$ is —$NR^3R^{3'}$ or optionally halogenated phenyl; $R^3$, $R^{3'}$, and $R^1$ are independently —H, $C_{1-6}$ alkyl, $C_{1-6}$ alkanoyl or $C_{1-6}$ aralkanoyl, or —$R^1$ represents a lone pair of the nitrogen to which it is attached; $Z^2$ is a β-bonded alkyl or alkenyl linking group, whereby Ring C is a heterocyclyl or heteroaryl ring; and Ring C is optionally substituted at any substitutable ring atom with halogen, —CN, —$NO_2$, —$R^a$, —$OR^a$, —$N(R^aR^b)$, =O, or phenyl. In certain embodiments, the compound, e.g., represented by structural formula Ig, is selected from the group consisting of:

-continued

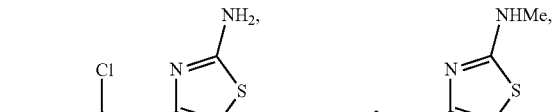

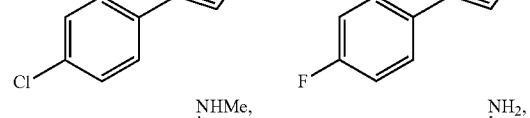

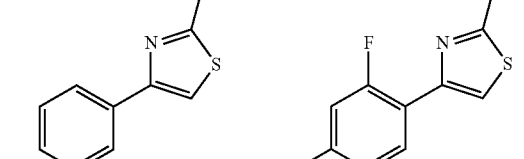

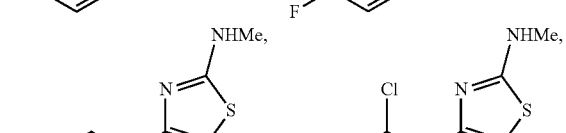

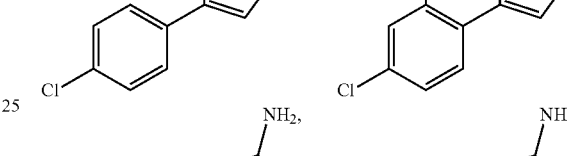

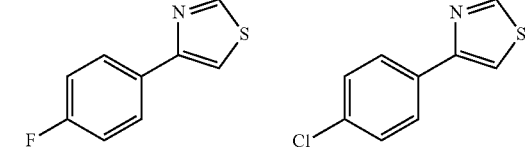

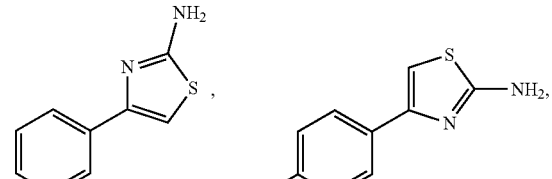

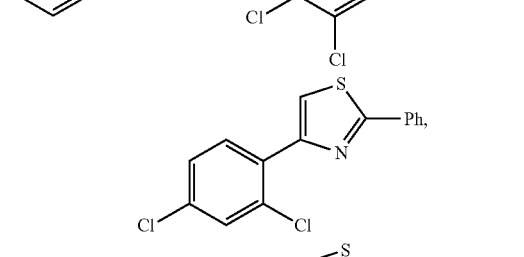

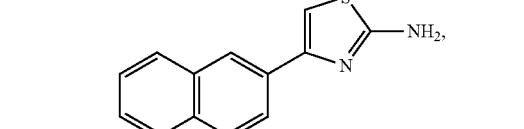

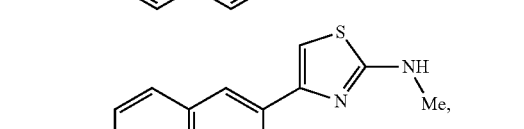

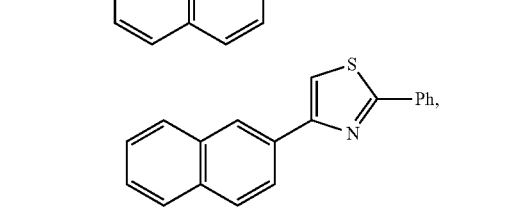

15
-continued

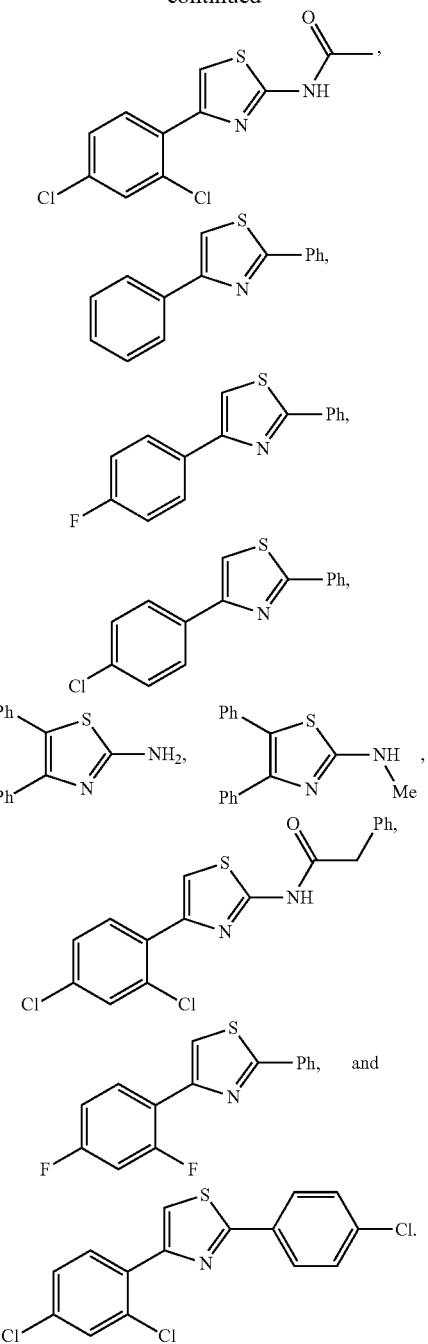

In certain embodiments, the compound, e.g., represented by structural formula Ig, is selected from the group consisting of:

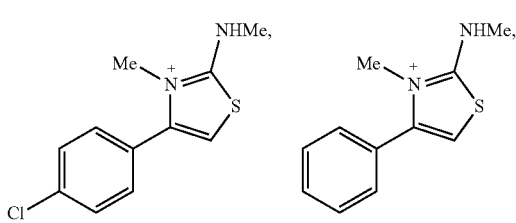

16
-continued

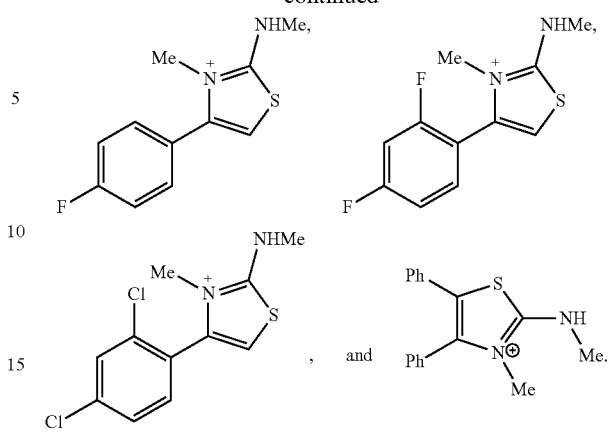

In some embodiments, the compound is represented by structural formula Ih:

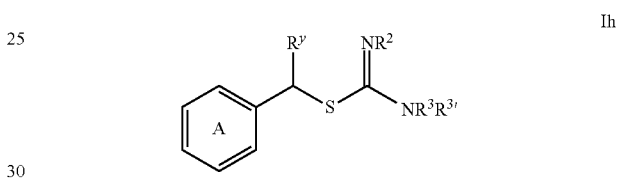

Ih

The variables in structural formula Ih can take any values as described for those variables herein. In some embodiments, in the compound represented by structural formula Ih, $R^3$, $R^{3'}$, $R^y$ and $R^2$ are independently —H, —OH, $C_{1-6}$ alkyl, $C_{1-6}$ alkoxy, or $C_{1-6}$ aralkyl, provided that at least two of $R^3$, $R^{3'}$, $R^y$ and $R^2$ are —H; or $R^3$ and $R^2$ together are —N=CH— or —CH=N—, optionally substituted with —N($R^aR^b$) or —C(O)N($R^aR^b$). The ring represented by Ring A is an optionally substituted naphthyl, pyridyl, quinolinyl, or isoquinolinyl; or a phenyl that is monsubstituted at its 2, 3, or 4 positions or disubstituted at its 2,3, 2,4, or 2,5 or 3,4 positions, wherein the 1 position is the point of attachment of Ring A to the rest of the compound. Typically, substituents for Ring A are independently —Br, —Cl, —F, —CN, —NO₂, $C_{1-6}$ alkoxy, methylenedioxy or —CF₃, provided that when Ring A is phenyl at least one substituent of Ring A is —F or —Cl.

A method of synthesizing a compound represented by structural formula Ia includes reacting a first reagent represented by structural formula IIa with a second reagent represented by structural formula IIIa, thereby forming the a compound represented by structural formula Ia:

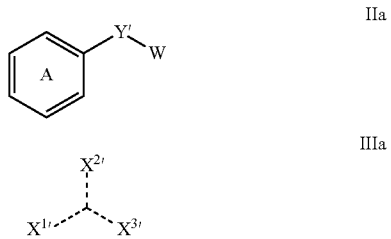

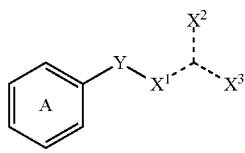

Ia

In the above structural formulas, each dashed line (- - -) represents a single bond, or one (- - -) is a double bond.

Y and Y' are an optionally substituted $C_{1-3}$alkylene or $C_{1-3}$alkenylene.

$X^{1'}$ is independently $=CH_2$, $—NH_2$, $=NH$, $—OH$, $—SH$, $=O$, or $=S$, and $X^1$ is correspondingly $—O—$, $—S—$, or optionally substituted $—CH_2—$, $—CH=$, $—NH—$, or $—N=$, wherein when W is unsubstituted $—NH_2$, $X^{1'}$ is and $X^1$ is optionally substituted $—NH—$ or $—N=$. $X^{2'}$ and $X^{3'}$ are independently $=S$ or optionally substituted $—NH_2$, $=NH$, or $—SR^a$, or an optionally substituted 3-7 membered aryl, heteroaryl, heterocyclyl, or cycloaliphatic ring, and $X^2$ and $X^3$ correspond to $X^{2'}$ and $X^{3'}$, respectively, or $X^{2'}$ and $X^{3'}$ are independently $—S—$ or optionally substituted $—NH—$, $—N=$, or $=N—$, and are optionally linked α, β, or γ through an optionally substituted alkyl, alkenyl, heteroalkyl, heteroalkenyl, heteroatom, aryl, heteroaryl, heterocyclyl, or cycloaliphatic linking group, thereby forming an optionally substituted heteroaryl or heterocyclyl ring, wherein $X^2$ and $X^3$ are likewised linked to correspond to $X^{2'}$ and $X^{3'}$, respectively; or $X^{2'}$ is independently $=S$ or optionally substituted $—NH_2$, $=NH$, or $—SH$, $X^2$ is correspondingly $—S—$ or optionally substituted $—NH—$, $—N=$, or $=N—$, and $X^2$ is linked α, β, or γ to a carbon of Y through an optionally substituted alkyl, alkenyl, heteroalkyl, heteroalkenyl, or heteroatom linking group, thereby forming an optionally substituted heteroaryl or heterocyclyl ring, and wherein $X^3$ is optionally $—H$. In some embodiments, $X^3$ is not $—H$. In some embodiments, $X^{1'}$ is $—OH$, $=O$, $—SH$, or $=S$, and $X^1$ is correspondingly $—O—$ or $—S—$. In some embodiments, $X^{1'}$ is $—SH$ or $=S$ and $X^1$ is correspondingly $—S—$.

W is a leaving group or unsubstituted $—NH_2$. The variable W can represent any leaving group known to the art. For example, in some embodiments, W can be halogen, perchlorate, amonioalkanesulfonate, halosulfonate, haloalkyl sulfonate, alkyl sulfonate, optionally substituted aryl sulfonate, or optionally substituted $—N(arylsulfonate)_2$. W can also be optionally alkylated halonium ion or optionally alkylated oxonium ion, prepared in situ. In some embodiments, W is $—Cl$, $—Br$, $—I$, $—OSO_2F$, $—OSO_2CF_3$, $—OSO_2C_4F_9$, $—OSO_2CH_2CF_3$, $—OSO_2CH_3$, tosylate, brosylate, nosylate, or $—N(tosylate)_2$. In certain embodiments, W is $—Cl$ or $—Br$.

Each substitutable carbon and nitrogen is optionally substituted as described herein above for any of structural formulas Ia-Ih. $X^{2'}$, $X^{3'}$, $X^2$, $X^3$, each nitrogen substituent, and each carbon substituent are each optionally protected with a protecting group as described herein above for structural formula Ia.

The method is provided that the compound is not benzyl N,N'-bis(tert-butoxy carbonyloxy) carbamimidothioate or a salt represented by

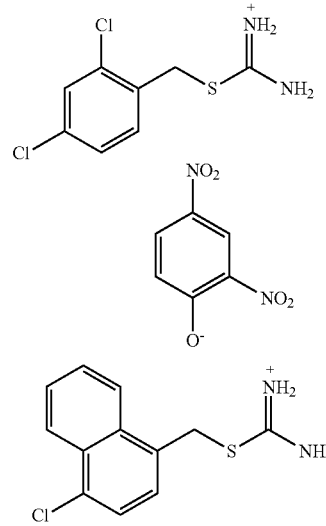

In various embodiments of the method, the first and second reagents are reacted together under microwave irradiation.

In some embodiments, the first reagent is represented by structural formula IIb and the second reagent is represented by structural formula IIIb, whereby the compound produced is represented by structural formula Ib:

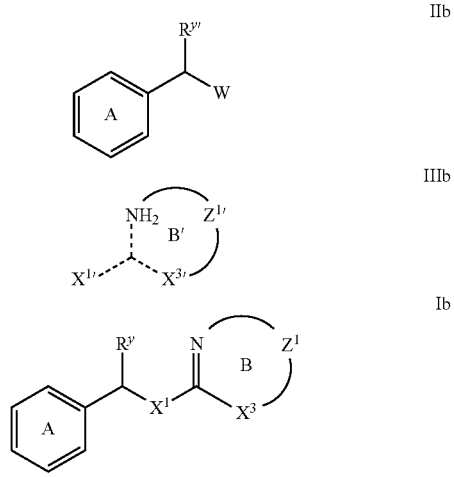

In the above structural formulas Ib, IIb and IIIb, $R^y$ and $R^{y'}$ are $—H$, $—OH$, $C_{1-6}$ alkyl, $C_{1-6}$alkoxy, $C_{1-6}$haloalkyl, $C_{1-6}$haloalkoxy, or $C_{1-6}$ aralkyl, or $—R^y$ and $—R^{y'}$ are $=O$ or $=S$; $X^{3'}$ and $X^3$ are N or S; $X^{1'}$ is $—OH$ or $—SH$ and $X^1$ is correspondingly $—O—$ or $—S—$; $Z^1$ and $Z^{1'}$ are each a heteroatom or a β- or γ-bonded alkyl, alkenyl, heteroalkyl, heteroalkenyl, aryl, heteroaryl, heterocyclyl, or cycloaliphatic linking group, whereby Ring B and Ring B' are corresponding heterocyclyl or heteroaryl rings; and Ring B and Ring B' are optionally substituted at any substitutable ring atom with halogen, —CN, —NO$_2$, —R$^a$, —OR$^a$, —C(O)R$^a$, —OC(O)R$^a$, —C(O)OR$^a$, —SR$^a$, —SO$_2$R$^a$, —SO$_3$R$^a$, —OSO$_2$R$^a$, —OSO$_3$R$^a$, —N(R$^a$R$^b$), —C(O)N(R$^a$R$^b$), —SO$_2$N(R$^a$R$^b$), —NR$^a$SO$_2$Rb, —NR$^c$C(O)R$^a$, —NR$^c$C(O)OR$^a$, or =O. In some embodiments, X$^{1'}$ is —SH and X$^1$ is correspondingly —S—. In some embodiments, Z$^1$ and Z$^{1'}$ are each 1,2-phenylene, —CH$_2$CH$_2$—, —CH=CH—, or —N=CH$_2$—; and Ring B and Ring B' are optionally substituted at any substitutable ring atom with halogen, —CN, —NO$_2$, —R$^a$, —OR$^a$, —N(R$^a$R$^b$), —C(O)N(R$^a$R$^b$), —NR$^c$C(O)R$^a$, or =O. In some embodiments, Z$^1$ and Z$^{1'}$ are —N=CH$_2$— optionally substituted with —N(R$^a$R$^b$). In certain embodiments, the compound produced using the first reagent represented by IIb and the second reagent represented by structural formula IIIb is selected from the group of specific compounds shown above under structural formula Ib.

In some embodiments, the second reagent is represented by structural formula IIIc, whereby the compound produced is represented by structural formula Id:

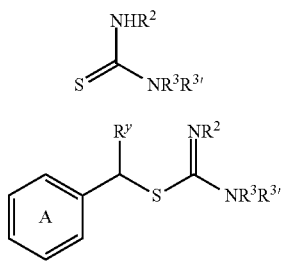

IIIc

Id

In the above structural formulas IIIc and Id, R$^3$, R$^{3'}$, R$^y$ and R$^2$ are independently —H, —OH, C$_{1-6}$ alkyl, C$_{1-6}$ alkoxy, C$_{1-6}$ haloalkyl, C$_{1-6}$ haloalkoxy, C$_{1-6}$ aralkyl, aryl, heteroaryl, heterocyclyl, or cycloaliphatic, or —R$^y$ is =O or =S. In some embodiments, R$^y$ is —H, C$_{1-6}$ alkyl, C$_{1-6}$ aralkyl, or =O. In certain embodiments, the compound produced is selected from the group of specific compounds shown above under by structural formula Id.

In some embodiments of the method, the first reagent is represented by structural formula IIc, whereby the compound is represented by structural formula Ie:

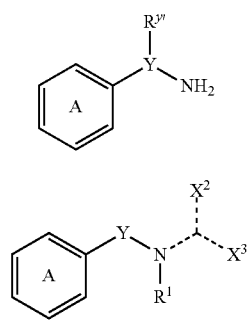

IIc

Ie

In the above structural formulas IIc and Ie, X$^{1'}$ is; none of X$^{2'}$, X$^{3'}$ X$^2$, or X$^3$ is unsubstituted —NH$_2$ or =NH; R$^1$ is —H, —OH, C$_{1-6}$ alkyl, C$_{1-6}$ alkoxy, C$_{1-6}$ haloalkyl, C$_{1-6}$ haloalkoxy, C$_{1-6}$ aralkyl, aryl, heteroaryl, heterocyclyl, or cycloaliphatic, or —R$^1$ represents a lone pair of the nitrogen to which it is attached; and one dashed line (- - -) represents a double bond and the other dashed lines represent single bonds.

In some embodiments, the second reagent is represented by structural formula IIId, thereby producing a protected intermediate represented by structural formula Ii:

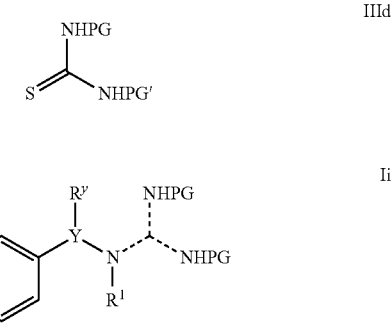

IIId

Ii

In the above structural formulas IIId and Ii, R$^1$ is —H, —OH, C$_{1-6}$ alkyl, C$_{1-6}$ alkoxy, C$_{1-6}$ haloalkyl, C$_{1-6}$ haloalkoxy, C$_{1-6}$ aralkyl, aryl, heteroaryl, heterocyclyl, or cycloaliphatic, or —R$^1$ represents a lone pair of the nitrogen to which it is attached. PG and PG' are amine protecting groups. The protecting groups PG and PG' can independently be any suitable amine protecting group, for example t-butyloxycarbonyl or benzyloxycarbonyl.

In some embodiments, the first reagent and the second reagent are reacted together in the presence of an optionally substituted 1-alkyl-2-halopyridinium salt or an optionally substituted 1-aryl-2-halopyridinium salt. In certain embodiments, the first reagent and the second reagent are reacted together in the presence of 1-methyl-2-chloropyridinium halide or 1-phenyl-2-chloropyridinium halide, typically 1-methyl-2-chloropyridinium iodide.

The method can further include removing protecting groups PG and PG' from the protected intermediate, thereby producing the compound, represented by structural formula Ij:

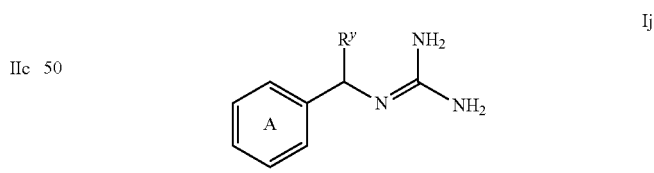

Ij

In some embodiments, when PG and PG' are t-butyloxycarbonyl or benzyloxycarbonyl, the step of removing PG and PG' from the protected intermediate can include contacting the protected intermediate with trifluoracetic acid or SnCl$_4$. In certain embodiments, the compound produced is selected from the group of specific compounds shown above under structural formula Ij.

In some embodiments, the first reagent is represented by structural formula IId, and the second reagent is represented by structural formula IIIe, whereby the compound is represented by structural formula Ig:

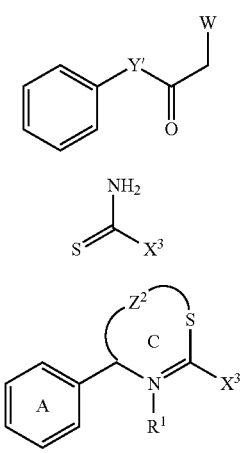

IId

IIIe

Ig

In the above structural formulas IId, IIIe, and Ig, Y' is methylene or a bond; $X^3$ is —$NR^3R^{3\prime}$ or optionally halogenated phenyl; $R^3$, $R^{3\prime}$, and $R^1$ are independently —H, $C_{1-6}$ alkyl, $C_{1-6}$ alkanoyl or $C_{1-6}$ aralkanoyl, or —$R^1$ represents a lone pair of the nitrogen to which it is attached; $Z^2$ is a β-bonded alkyl or alkenyl linking group, whereby Ring C is a heterocyclyl or heteroaryl ring; and Ring C is optionally substituted at any substitutable ring atom with halogen, —CN, —$NO_2$, —$R^a$, —$OR^a$, —$N(R^aR^b)$, =O, or phenyl. In certain embodiments, the compound produced is selected from the group of specific compounds shown above under structural formula Ig.

In some embodiments, the first reagent is represented by structural formula IIe, and the second reagent is represented by structural formula IIIf, whereby the compound is represented by structural formula Ih:

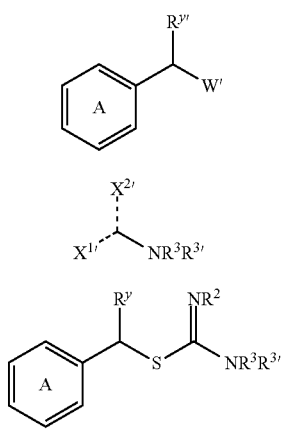

IIe

IIIf

Ih

In the above structural formulas IIe, IIIf, and Ih, $X^{1\prime}$ is —SH and $X^{2\prime}$ is =$NR^2$, or $X^{1\prime}$ is =S and $X^{2\prime}$ is —$NHR^2$; W' is —Cl, —Br, or —I; and $R^3$, $R^{3\prime}$, $R^y$ and $R^2$ are independently —H, —OH, $C_{1-6}$ alkyl, $C_{1-6}$ alkoxy, or $C_{1-6}$ aralkyl, provided that at least two of $R^3$, $R^{3\prime}$, $R^y$ and $R^2$ are —H; or $R^3$ and $R^2$ together are —N=CH— or —CH=N—, optionally substituted with —$N(R^aR^b)$ or —$C(O)N(R^aR^b)$.

The ring represented by Ring A is an optionally substituted naphthyl, pyridyl, quinolinyl, or isoquinolinyl; or a phenyl that is monosubstituted at its 2, 3, or 4 positions or disubstituted at its 2,3, 2,4, or 2,5 or 3,4 positions, wherein the 1 position is the point of attachment of Ring A to the rest of the compound. Substituents for Ring A are independently —Br, —Cl, —F, —CN, —$NO_2$, $C_{1-6}$ alkoxy, methylenedioxy or —$CF_3$, provided that when Ring A is phenyl at least one substituent of Ring A is —F or —Cl.

In some embodiments, the first reagent is prepared from a third reagent represented by structural formula IV:

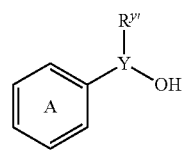

IV by converting the hydroxyl group bound to Y in the third reagent to the groups represented by W such as —$NH_2$ or a leaving group selected from halogen, optionally alkylated halonium ion, optionally alkylated oxonium ion, perchlorate, amonioalkanesulfonate, halosulfonate, haloalkyl sulfonate, alkyl sulfonate, optionally substituted aryl sulfonate, or optionally substituted —$N(arylsulfonate)_2$.

In some embodiments, the third reagent is prepared by reacting a fourth reagent represented by structural formula Va:

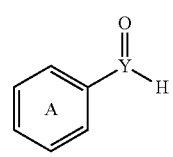

Va with $R^{y\prime\prime}$MgCl, $R^{y\prime\prime}$MgBr, $R^{y\prime\prime}$MgI, $R^{y\prime\prime}$Li, $R^{y\prime\prime}$Na, or $R^{y\prime\prime}$K. Such derivatives can be readily prepared from the corresponding $R^{y\prime\prime}$-halide.

In some embodiments, the third reagent can be prepared by reducing a fifth reagent represented by structural formula Vb:

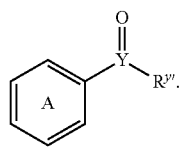

Vb

Typical reagents and conditions for reducing carbonyls to alcohols are well-known, for example, lithium aluminum hydride, sodium borohydride, lithium hydride, sodium hydride, potassium hydride, hydrogen in the presence of a catalyst, e.g., Pd or Pt on carbon, electrochemical methods, and the like.

A pharmaceutical composition includes a compound represented by structural formulas Ia-Ih and optionally a pharmaceutically acceptable carrier or excipient.

A protein:ligand complex includes a compound represented by structural formula Ia and at least one protein selected from the group consisting of retinoblastoma tumor suppressor protein and serine-threonine kinase Raf-1. The complex can include a disclosed compound, retinoblastoma tumor suppressor protein, and serine-threonine kinase Raf-1.

Various methods of treatment of cells and subjects are included. For example, a method of inhibiting proliferation of a cell includes contacting the cell with an effective amount of the disclosed compounds or compositions. Typically, regulation of proliferation in the cell is mediated by at least one protein selected from the group consisting of retinoblastoma tumor suppressor protein and serine-threonine kinase Raf-1. For example, in various embodiments, the cells have an elevated level of Rb, Raf-1, or Rb bound to Raf-1. In some embodiment, the method includes assaying the level of Rb, Raf-1, or Rb bound to Raf-1 in the cell.

A method of modulating the Rb:Raf-1 interaction in a proliferating cell includes contacting the cell with an effective amount of the disclosed compounds or compositions.

A method of modulating the Rb:Raf-1 interaction in a proliferating cell includes contacting the cell with a modulator of the Rb:Raf-1 interaction that is suitable for oral administration. In some embodiments, the modulator of the Rb:Raf-1 interaction is orally administered.

A method of treating or ameliorating a cell proliferation disorder includes contacting the proliferating cells with an effective amount of the disclosed compounds or compositions Typically, regulation of cell proliferation in the disorder can be mediated by at least one protein selected from the group consisting of retinoblastoma tumor suppressor protein and serine-threonine kinase Raf-1. In some embodiments, the regulation of proliferation in the cells is mediated by the interaction between retinoblastoma tumor suppressor protein and serine-threonine kinase Raf-1. In various embodiments, the cell proliferation disorder is cancer or a non-cancerous cell proliferation disorder. In some embodiments, the cell proliferation disorder includes angiogenesis or the cell proliferation disorder is mediated by angiogenesis.

In various embodiments, the cell proliferation disorder is or the proliferating cells are derived from a cancerous or a non-cancerous cell proliferation disorder. Exemplary cancerous and non-cancerous cell proliferation disorders include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, acute lymphocytic leukemia, lymphocytic leukemia, large granular lymphocytic leukemia, acute myelocytic leukemia, chronic leukemia, polycythemia vera, Hodgkin's lymphoma, non-Hodgkin's lymphoma, multiple myeloma, Waldenstrobm's macroglobulinemia, heavy chain disease, lymphoblastic leukemia, T-cell leukemia, T-lymphocytic leukemia, T-lymphoblastic leukemia, B cell leukemia, B-lymphocytic leukemia, mixed cell leukemias, myeloid leukemias, myelocytic leukemia, myelogenous leukemia, neutrophilic leukemia, eosinophilic leukemia, monocytic leukemia, myelomonocytic leukemia, Naegeli-type myeloid leukemia, nonlymphocytic leukemia, osteosarcoma, promyelocytic leukemia, non-small cell lung cancer, epithelial lung carcinoma, pancreatic carcinoma, pancreatic ductal adenocarcinoma, glioblastoma, metastatic breast cancer, melanoma, and prostate cancer. In certain embodiments, the cell proliferation disorder is osteosarcoma, promyelocytic leukemia, non-small cell lung cancer, epithelial lung carcinoma, pancreatic carcinoma, pancreatic ductal adenocarcinoma, glioblastoma, metastatic breast cancer, melanoma, or prostate cancer.

A method of inhibiting angiogenic tubule formation in a subject in need thereof includes administering to the subject an effective amount of the disclosed compounds or compositions.

In some embodiments, the preceding methods of treating subjects or cells can also include coadministration of an anticancer drug or a compound that modulates angiogenic tubule formation, particularly coadministration of a compound that inhibits angiogenic tubule formation. Exemplary anticancer drugs and compounds that can modulate angiogenic tubule formation are provided in the detailed description.

A method of assessing a subject for treatment with an inhibitor of Rb:Raf-1 binding interactions includes determining, in the subject or in a sample from the subject, a level of Rb, Raf-1, or Rb bound to Raf-1, wherein treatment with an inhibitor of Rb:Raf-1 binding interactions is indicated when the level of Rb, Raf-1, or Rb bound to Raf-1 is elevated compared to normal.

A method of identifying a subject for therapy includes the steps of providing a sample from the subject, determining a level of Rb, Raf-1, or Rb bound to Raf-1 in the sample; and identifying the subject for therapy with an inhibitor of Rb:Raf-1 binding interactions when the level of Rb, Raf-1, or Rb bound to Raf-1 is elevated compared to normal.

A kit includes an antibody specific for Rb, Raf-1, or Rb bound to Raf-1; and instructions for determining the level of Rb, Raf-1, or Rb bound to Raf-1 in a sample using the antibody specific for Rb, Raf-1, or Rb bound to Raf-1.

In various embodiments, methods relating to cells can be conducted on cells in vitro or in vivo, particularly wherein the cell is in vivo in a subject. The subject can be, for example, a bird, a fish, or a mammal, e.g., a human.

In conclusion, the compounds, pharmaceutical compositions, and methods of treatment described in this application are believed to be effective for inhibiting cellular proliferation, particularly of cells which proliferate due to a mutation or other defect in the Rb:Raf-1 regulatory pathway. In particular, the disclosed compounds, pharmaceutical compositions, and methods of treatment are believed to be effective for treating cancer and other proliferative disorders which can be inhibited by disrupting Rb:Raf-1 binding interactions in the proliferating cells.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3D: BrdU incorporation assay showing the growth arrest mediated by 3a in a variety of tumor cell lines harboring various mutations. 3a could effectively arrest cells with mutations in EGFR, p16, PTEN, K-Ras, and p53. In contrast cells lacking the Rb gene rendered the cells resistant to 3a.

DETAILED DESCRIPTION

Figure 1A:
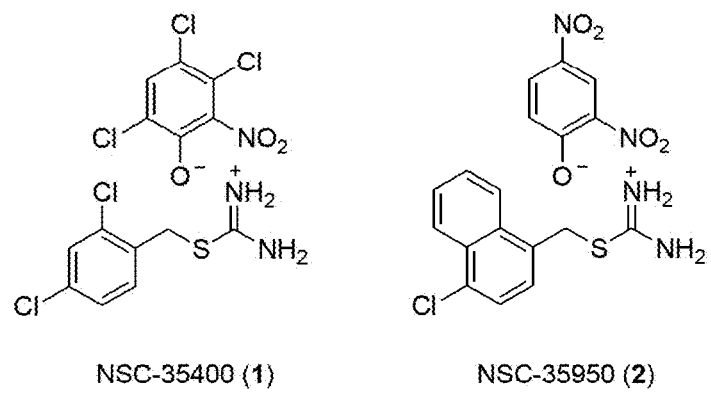
FIG. 1A: Identification of novel Rb:Raf-1 inhibitors. Compounds identified in the DTP diversity set that showed the highest inhibition of Rb:Raf-1 by ELISA. Highest scoring compounds (1) and (2) are both benzyl isothiourea derivatives.

This application relates to compounds, pharmaceutical compositions, and methods for modulating cell proliferation and/or Rb:Raf-1 interaction in a cell, either in vitro or in vivo. For example, disorders that can be treated with the disclosed compounds, compositions, and methods include diseases such as cancer as well as non-cancerous proliferation disorders. Without wishing to be bound by theory, it is believed that the pharmaceutical activity of the disclosed compounds arises, at least in part, to modulation of Rb:Raf-1 binding interactions by the disclosed compound, and more particularly to disruption of Rb:Raf-1 binding.

In various embodiments, the disclosed compounds are modulators of Rb:Raf-1 binding interactions. A modulator can change the action or activity of the molecule, enzyme, or system which it targets. For example, the disclosed modulators can modulate Rb:Raf 1 binding interactions to inhibit, disrupt, prevent, block or antagonize Rb, Raf-1, or Rb:Raf-1 binding interactions, or otherwise prevent association or interaction between Rb and Raf-1. Thus, the disclosed compounds can be inhibitors, disruptors, blockers, or antagonists of Rb or Raf-1 activity, or of Rb:Raf-1 binding interactions.

Thus, the compounds, pharmaceutical compositions, and methods of use described in this application are believed to be effective for inhibiting cellular proliferation, particularly of cells which proliferate due to a mutation or other defect in the Rb:Raf-1 regulatory pathway. In particular, the disclosed compounds, pharmaceutical compositions, and methods of use are believed to be effective for treating cancer and other proliferative disorders which can be inhibited by disrupting Rb:Raf-1 binding interactions in the proliferating cells.

Definitions

An aliphatic group is a straight chained, branched non-aromatic hydrocarbon which is completely saturated or which contains one or more units of unsaturation. A cycloaliphatic group is an aliphatic group that forms a ring. Alkyl and cycloalkyl groups are saturated aliphatic and saturated cycloaliphatic groups, respectively. Typically, a straight chained or branched aliphatic group has from 1 to about 10 carbon atoms, typically from 1 to about 6, and preferably from 1 to about 4, and a cyclic aliphatic group has from 3 to about 10 carbon atoms, typically from 3 to about 8, and preferably from 3 to about 6. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. $C_{1-6}$ straight chained or branched alkyl or alkoxy groups or a $C_{3-8}$ cyclic alkyl or alkoxy group (preferably $C_{1-6}$ straight chained or branched alkyl or alkoxy group) are also referred to as a "lower alkyl" or "lower alkoxy" groups; such groups substituted with —F, —Cl, —Br, or —I are "lower haloalkyl" or "lower haloalkoxy" groups; a "lower hydroxyalkyl" is a lower alkyl substituted with —OH; and the like.

An "alkylene" group is a linking alkyl chain represented by —$(CH_2)_n$—, wherein n, the number of "backbone" atoms in the chain, is an integer from 1-10, typically 1-6, and preferably 1-4. An "alkenylene" group is a linking alkyl chain having one or more double bonds, wherein the number of backbone atoms is an integer from 1-10, typically 1-6, and preferably 1-4. An "alkynylene" group is a linking alkyl chain having one or more triple bonds and optionally one or more double bonds, wherein the number of "backbone" atoms is an integer from 1-10, typically 1-6, and preferably 1-4.

"Heteroalkylene," "heteroalkenylene," and "heteroalkynylene" groups are alkylene, alkenylene, and alkynylene groups, respectively, wherein one or more carbons are replaced with heteroatoms such as N, O, or S.

A heterocyclic group is a non-aromatic cycloaliphatic group which has from 3 to about 10 ring atoms, typically from 3 to about 8, and preferably from 3 to about 6, wherein one or more of the ring atoms is a heteroatom such as N, O, or S in the ring. Examples of heterocyclic groups include oxazolinyl, thiazolinyl, oxazolidinyl, thiazolidinyl, tetrahydrofuranyl, tetrahyrothiophenyl, morpholino, thiomorpholino, pyrrolidinyl, piperazinyl, piperidinyl, thiazolidinyl, and the like.

The term "aryl" refers to $C_{6-14}$ carbocyclic aromatic groups such as phenyl, biphenyl, and the like. Aryl groups also include fused polycyclic aromatic ring systems in which a carbocyclic aromatic ring is fused to other aryl, cycloalkyl, or cycloaliphatic rings, such as naphthyl, pyrenyl, anthracyl, 9,10-dihydroanthracyl, fluorenyl, and the like.

The term "heteroaryl" refers to 5-14 membered aryl groups having 1 or more O, S, or N heteroatoms. Examples of heteroaryl groups include pyridyl, pyrimidyl, pyrazinyl, triazinyl, pyranyl, pyrrolyl, imidazolyl, pyrazolyl, 1,2,3-trizaolyl, 1,2,4-triazolyl, tetrazolyl, thienyl, thiazoyl, isothiazolyl, furanyl, oxazolyl, isooxazolyl, and the like. Heteroaryl groups also include fused polycyclic aromatic ring systems in which a carbocyclic aromatic ring or heteroaryl ring is fused to one or more other heteroaryl rings. Examples include quinolinyl, isoquinolinyl, quinazolinyl, napthyridyl, pyridopyrimidyl, benzothienyl, benzothiazolyl, benzoisothiazolyl, thienopyridyl, thiazolopyridyl, isothiazolopyridyl, benzofuranyl, benzooxazolyl, benzoisooxazolyl, furanopyridyl, oxazolopyridyl, isooxazolopyridyl, indolyl, isoindolyl, benzimidazolyl, benzopyrazolyl, pyrrolopyridyl, isopyrrolopyridyl, imidazopyridyl, pyrazolopyridyl, and the like. A ring recited as a substituent herein can be bonded via any substitutable atom in the ring.

Suitable optional substituents for a substitutable atom in the preceding groups, e.g., alkyl, cycloalkyl, aliphatic, cycloaliphatic, alkylene, alkenylene, alkynylene, heteroalkylene, heteroalkenylene, heteroalkynylene, heterocyclic, aryl, and heteroaryl groups, are those substituents that do not substantially interfere with the pharmaceutical activity of the disclosed compounds. A "substitutable atom" is an atom that has one or more valences or charges available to form one or more corresponding covalent or ionic bonds with a substituent. For example, a carbon atom with one valence available (e.g., —C(—H)═) can form a single bond to an alkyl group (e.g., —C(-alkyl)═), a carbon atom with two valences available (e.g., —C(H$_2$)—) can form one or two single bonds to one or two substituents (e.g., —C(alkyl)(H)—, —C(alkyl)(Br))—,) or a double bond to one substituent (e.g., —C(═O)—), and the like. Substitutions contemplated herein include only those substitutions that form stable compounds.

For example, suitable optional substituents for substitutable carbon atoms include —F, —Cl, —Br, —I, —CN, —NO$_2$, —OR$^a$, —C(O)R$^a$, —OC(O)R$^a$, —C(O)OR$^a$, —SR$^a$, —C(S)R$^a$, —OC(S)R$^a$, —C(S)OR$^a$, —C(O)SR$^a$, —C(S)SR$^a$, —S(O)R$^a$, —SO$_2$R$^a$, —SO$_3$R$^a$, —OSO$_2$R$^a$, —OSO$_3$R$^a$, —PO$_2$R$^a$R$^b$, —OPO$_2$R$^a$R$^b$, —PO$_3$R$^a$R$^b$, —OPO$_3$R$^a$R$^b$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), —C(NR$^c$)—N(R$^a$R$^b$), —NR$^d$—C(NR$^c$)—N(R$^a$R$^b$), —NR$^a$N(R$^a$R$^b$), —CR$^c$═CR$^a$R$^b$, —C≡CR$^a$, ═O, ═S, ═CR$^a$R$^b$, ═NR$^a$, ═NOR$^a$, ═NNR$^a$, optionally substituted alkyl, optionally substituted cycloalkyl, optionally substituted aliphatic, optionally substituted cycloaliphatic, optionally substituted heterocyclic, optionally substituted benzyl, optionally substituted aryl, and optionally substituted heteroaryl, wherein R$^a$-R$^d$ are each independently —H or an optionally substituted aliphatic, optionally substituted cycloaliphatic, optionally substituted heterocyclic, optionally substituted benzyl, optionally substituted aryl, or optionally substituted heteroaryl, or, —N(R$^a$R$^b$), taken together, is an optionally substituted heterocyclic group.

Suitable substituents for nitrogen atoms having two covalent bonds to other atoms include, for example, optionally substituted alkyl, optionally substituted cycloalkyl, optionally substituted aliphatic, optionally substituted cycloaliphatic, optionally substituted heterocyclic, optionally substituted benzyl, optionally substituted aryl, optionally substituted heteroaryl, —CN, —NO$_2$, —OR$^a$, —C(O)R$^a$, —OC(O)R$^a$, —C(O)OR$^a$, —SR$^a$, —S(O)R$^a$, —SO$_2$R$^a$, —SO$_3$R$^a$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), and the like.

A nitrogen-containing group, for example, a heteroaryl or non-aromatic heterocycle, can be substituted with oxygen to form an N-oxide, e.g., as in a pyridyl N-oxide, piperidyl N-oxide, and the like. For example, in various embodiments, a ring nitrogen atom in a nitrogen-containing heterocyclic or heteroaryl group can be substituted to form an N-oxide.

Suitable substituents for nitrogen atoms having three covalent bonds to other atoms include —OH, alkyl, and alkoxy (preferably $C_{1-6}$ alkyl and alkoxy). Substituted ring nitrogen atoms that have three covalent bonds to other ring atoms are positively charged, which is balanced by counteranions corresponding to those found in pharmaceutically acceptable salts, such as chloride, bromide, fluoride, iodide, formate, acetate and the like. Examples of other suitable counteranions are provided in the section below directed to suitable pharmacologically acceptable salts.

It will also be understood that certain disclosed compounds can be obtained as different stereoisomers (e.g., diastereomers and enantiomers) and that the invention includes all isomeric forms and racemic mixtures of the disclosed compounds and methods of treating a subject with both pure isomers and mixtures thereof, including racemic mixtures. Stereoisomers can be separated and isolated using any suitable method, such as chromatography.

Also included in the present invention are pharmaceutically acceptable salts of the disclosed compounds. These disclosed compounds can have one or more sufficiently acidic protons that can react with a suitable organic or inorganic base to form a base addition salt. When it is stated that a compound has a hydrogen atom bonded to an oxygen, nitrogen, or sulfur atom, it is contemplated that the compound also includes salts thereof where this hydrogen atom has been reacted with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like.

For example, pharmaceutically acceptable salts of the disclosed compounds can include those formed by the reaction of the disclosed compounds with one equivalent of a suitable base to form a monovalent salt (i.e., the compound has single negative charge that is balanced by a pharmaceutically acceptable counter cation, e.g., a monovalent cation) or with two equivalents of a suitable base to form a divalent salt (e.g., the compound has a two-electron negative charge that is balanced by two pharmaceutically acceptable counter cations, e.g., two pharmaceutically acceptable monovalent cations or a single pharmaceutically acceptable divalent cation). "Pharmaceutically acceptable" means that the cation is suitable for administration to a subject. Examples include $Li^+$, $Na^+$, $K^+$, $Mg^{2+}$, $Ca^{2+}$ and $NR_4^+$, wherein each R is independently hydrogen, an optionally substituted aliphatic group (e.g., a hydroxyalkyl group, aminoalkyl group or ammoniumalkyl group) or optionally substituted aryl group, or two R groups, taken together, form an optionally substituted non-aromatic heterocyclic ring optionally fused to an aromatic ring. Generally, the pharmaceutically acceptable cation is $Li^+$, $Na^+$, $K^+$, $NH_3(C_2H_5OH)^+$ or $N(CH_3)_3(C_2H_5OH)^+$.

Pharmaceutically acceptable salts of the disclosed compounds with a sufficiently basic group, such as an amine, can be formed by reaction of the disclosed compounds with an organic or inorganic acid to form an acid addition salt. Acids commonly employed to form acid addition salts from compounds with basic groups can include inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate-, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like. In certain embodiments, the disclosed compound forms a pharmaceutically acceptable salt with HCl, HF, HBr, HI, trifluoracetic acid, or sulfuric acid. In particular embodiments, the disclosed compound forms a pharmaceutically acceptable salt with sulfuric acid. Also included are pharmaceutically acceptable solvates. As used herein, the term "solvate" means a compound of the present invention or a salt thereof, that further includes a stoichiometric or non-stoichiometric amount of solvent, e.g., water or organic solvent, bound by non-covalent intermolecular forces.

Preparation Methods

Synthetic chemistry functional group transformations useful in synthesizing the disclosed compounds are known in the art and include, for example, those described in R. Larock, Comprehensive Organic Transformations, VCH Publishers (1989); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995). The entire teachings of these documents are incorporated herein by reference. For example, suitable techniques for converting the —OH group in the third reagent represented by formula IV to the amine or leaving group represented by variable W in the first reagent represented by formula IIa are well known. In particular, the —OH in structural formula IV can be converted to —Cl, for example, using a chlorinating reagent such as thionyl chloride or N-chlorosuccinimide in combination with ultraviolet irradiation. Also, typical reagents and conditions for reducing carbonyls to alcohols (e.g., carbonyl Vb to alcohol IV) are well-known, for example, lithium aluminum hydride, sodium borohydride, lithium hydride, sodium hydride, potassium hydride, hydrogen in the presence of a catalyst, e.g., Pd or Pt on carbon, electrochemical methods, and the like. Further, typical reagents and conditions for preparing Grignard or organoalkali derivatives of $R^{3"}$ to convert carbonyl Vb to alcohol IV such as $R^{3"}MgCl$, $R^{3"}MgBr$, $R^{3"}MgI$, $R^{3"}Li$, $R^{3"}Na$, or $R^{3"}K$ can be readily prepared from the corresponding $R^{3"}$-halide, e.g., when $R^{3"}$ is $C_{1-6}$ alkyl, $C_{1-6}$ aralkyl, or aryl.

As used herein, "suitable protecting groups" and strategies for protecting and deprotecting functional groups using protecting groups useful in synthesizing the disclosed compounds are known in the art and include, for example, those described in T. W. Greene and P. G. M. Wuts, Protective Groups in Organic Synthesis, 2nd Ed., John Wiley and Sons (1991),), the entire teachings of which are incorporated herein by reference. For example, suitable hydroxyl protecting groups include, but are not limited to substituted methyl ethers (e.g., methoxymethyl, benzyloxymethyl) substituted ethyl ethers (e.g., ethoxymethyl, ethoxyethyl)benzyl ethers (benzyl, nitrobenzyl, halobenzyl) silyl ethers (e.g., trimethylsilyl), esters, and the like. Examples of suitable amine protecting groups include benzyloxycarbonyl, tert-butoxycarbonyl, tert-butyl, benzyl and fluorenylmethyloxy-carbonyl (Fmoc). Examples of suitable thiol protecting groups include benzyl, tert-butyl, acetyl, methoxymethyl and the like.

The reactions described herein may be conducted in any suitable solvent for the reagents and products in a particular reaction. Suitable solvents are those that facilitate the intended reaction but do not react with the reagents or the products of the reaction. Suitable solvents can include, for example: ethereal solvents such as diethyl ether or tetrahydrofuran; ketone solvents such as acetone or methyl ethyl ketone; halogenated solvents such as dichloromethane, chloroform, carbon tetrachloride, or trichloroethane; aromatic solvents such as benzene, toluene, xylene, or pyridine; polar aprotic organic solvents such as acetonitrile, dimethyl sulfoxide, dimethyl formamide, N-methyl pyrrolidone, hexamethyl phosphoramide, nitromethane, nitrobenzene, or the like; polar protic solvents such as methanol, ethanol, propanol, butanol, ethylene glycol, tetraethylene glycol, or the like; nonpolar hydrocarbons such as pentane, hexane, cyclohexane, cyclopentane, heptane, octance, or the like; basic amine solvents such as pyridine, triethyleamine, or the like; and other solvents known to the art.

Reactions or reagents which are water sensitive may be handled under anhydrous conditions. Reactions or reagents which are oxygen sensitive may be handled under an inert atmosphere, such as nitrogen, helium, neon, argon, and the like. Reactions or reagents which are light sensitive may be handled in the dark or with suitably filtered illumination.

Reactions or reagents which are temperature-sensitive, e.g., reagents that are sensitive to high temperature or reactions which are exothermic may be conducted under temperature controlled conditions. For example, reactions that are strongly exothermic may be conducted while being cooled to a reduced temperature.

Reactions that are not strongly exothermic may be conducted at higher temperatures to facilitate the intended reaction, for example, by heating to the reflux temperature of the reaction solvent. Reactions can also be conducted under microwave irradiation conditions. For example, in various embodiments of the method, the first and second reagents are reacted together under microwave irradiation.

Reactions may also be conducted at atmospheric pressure, reduced pressure compared to atmospheric, or elevated pressure compared to atmospheric pressure. For example, a reduction reaction may be conducted in the presence of an elevated pressure of hydrogen gas in combination with a hydrogenation catalyst.

Reactions may be conducted at stoichiometric ratios of reagents, or where one or more reagents are in excess. For example, in forming the compound, e.g., represented by formula Ia, using the first reagent, e.g., represented by IIa and the second reagent, e.g., represented by formula IIIa, the first reagent may be used in a molar ratio to the second reagent of about 20:1, 10:1, 5:1, 2.5:1, 2:1, 1.5:1, 1.3:1, 1.2:1, 1.1:1, 1:1, 0.91:1, 0.83:1, 0.77:1, 0.67:1, 0.5:1, 0.4:1, 0.2:1, 0.1:1 or 0.5:1. Typically, the first reagent may be used in a molar ratio to the second reagent of about 5:1, 2.5:1, 2:1, 1.5:1, 1.3:1, 1.2:1, 1.1:1, 1:1, 0.91:1, 0.83:1, 0.77:1, 0.67:1, 0.5:1, 0.4:1. In certain embodiments, the first reagent may be used in a molar ratio to the second reagent of about 1.5:1, 1.3:1, 1.2:1, 1.1:1, 1:1, 0.91:1, 0.83:1, 0.77:1, or 0.67:1. Preferably, first reagent may be used in a molar ratio to the second reagent of between about 1.1:1 and 0.9:1, typically about 1:1. The same ratios may be used for other reagents in the reaction. For example, when the first reagent and the second reagent are reacted together in the presence of a pyridinium salt (e.g., 1-alkyl-2-halopyridinium salt or an optionally substituted 1-aryl-2-halopyridinium salt), the first reagent may be used in a molar ratio to the pyridinium salt independently selected from the preceding ranges of ratios between the first reagent and the second reagent. Likewise, when the third reagent is prepared by reacting a fourth reagent represented by structural formula Va with a Grignard or organoalkali (e.g., R³"MgCl, R³"MgBr, R³"MgI, R³"Li, R³"Na, or R³"K, wherein R³" is $C_{1-6}$ alkyl, $C_{1-6}$ aralkyl, or aryl), the fourth reagent may be used in a molar ratio to the Grignard or organoalkali independently selected from the preceding ranges of ratios between the first reagent and the second reagent. Similarly, when the fourth reagent is prepared by reducing the fifth reagent, the ratio between the reducing agent and the fifth reagent can be independently selected from the preceding ranges of ratios between the first reagent and the second reagent.

Assay Methods

The disclosed compounds can be assayed for binding and biological activity by any means described herein or known to the art. For example, the disclosed compounds can be screened for binding activity in an ELISA assay (see Methods, Example 1), the $IC_{50}$ values of the disclosed compounds can be determined by in vitro binding assays (see Methods, Example 4), the binding selectivity of the disclosed compounds can be measured in competitive ELISA assays (see Example 5 and 8), and the ability of the disclosed compounds to disrupt Rb:Raf-1 in vitro (see Example 6) or in vivo (see Example 7) can be assayed.

Further, the disclosed compounds can be tested for their ability to kill or inhibit the growth of tumor cells or angiogenic tubules. Suitable assays include, for example, (a) tumor cell in anchorage/independent growth (soft agar assays, see Methods and Example 19) (b) tumor cell in anchorage-dependent growth (3-(4,5-Dimethylthiazol-2-yl)-2,5-diphenyltetrazolium bromide (MTT), trypan blue and DNA synthesis assays) (c) tumor cell survival (TUNEL, PARP cleavage, caspace activation and other apoptosis assays, see Methods and Example 20) (d) tumor cell invasion and metastasis (see methods) (e) endothelial cell migration, invasion and angiogenesis (see Methods and Example 18) (f) tumor cell proliferation inhibition assays (see Examples 9-16) (g) anti-tumor activity assays in animal models (see Example 20), and other such assays known to the art.

Certain assays can be used to assess a subject for treatment with an inhibitor of Rb:Raf-1 binding interactions or to identify a subject for therapy. The level of Rb, Raf-1, or Rb bound to Raf-1 can be determined in the subject or in a sample from the subject, e.g., a subject with a cell proliferation disorder. treatment with the disclosed compounds is indicated when the level of Rb, Raf-1, or Rb bound to Raf-1 is elevated compared to normal. "Elevated compared to normal" means that the levels are higher than in a reference sample of cells of the same type that are healthy. For example, the level of Rb, Raf-1, or Rb bound to Raf-1 in cells from a non-small cell lung cancer tumor can be compared to the level of Rb, Raf-1, or Rb bound to Raf-1 in normal, noncancerous cells. For example, Enzyme Linked ImmunoSorbent Assay (ELISA) can be used in combination with antibodies to Rb, Raf-1, or Rb bound to Raf-1 (see Methods, In vitro library screening assays and Example 5). The assay can be embodied in a kit. For example, a kit includes a reagent or indicator, such as an antibody, that is specific for Rb, Raf-1, or Rb bound to Raf-1. The kit can also include instructions for determining the level of Rb, Raf-1, or Rb bound to Raf-1 in a sample using the reagent or indicator, such as an antibody, that is specific for Rb, Raf-1, or Rb bound to Raf-1.

Utility

In various embodiments, methods relating to cells can be conducted on cells in vitro or in vivo, particularly wherein the cell is in vivo, i.e., the cell is located in a subject. A "subject" can be any animal with a proliferative disorder, for example, mammals, birds, reptiles, or fish. Preferably, the animal is a mammal. More preferably, the mammal is selected from the group consisting of dogs, cats, sheep, goats, cattle, horses, pigs, mice, non-human primates, and humans. Most preferably, the mammal is a human.

Disease Indications

As used herein, a "cell proliferation disorder" includes cancer and non-cancerous cell proliferation disorders. In some embodiments, the cell proliferation disorder is angiogenesis or the cell proliferation disorder is mediated by angiogenesis.

As used herein, a "cancer" includes, for example, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, acute lymphocytic leukemia, lymphocytic leukemia, large granular lymphocytic leukemia, acute myelocytic leukemia, chronic leukemia, polycythemia vera, Hodgkin's lymphoma, non-Hodgkin's lymphoma, multiple myeloma, Waldenstrobm's macroglobulinemia, heavy chain disease, lymphoblastic leukemia, T-cell leukemia, T-lymphocytic leukemia, T-lymphoblastic leukemia, B cell leukemia, B-lymphocytic leukemia, mixed cell leukemias, myeloid leukemias, myelocytic leukemia, myelogenous leukemia, neutrophilic leukemia, eosinophilic leukemia, monocytic leukemia, myelomonocytic leukemia, Naegeli-type myeloid leukemia, nonlymphocytic leukemia, osteosarcoma, promyelocytic leukemia, non-small cell lung cancer, epithelial lung carcinoma, pancreatic carcinoma, pancreatic ductal adenocarcinoma, glioblastoma, metastatic breast cancer, melanoma, or prostate cancer.

In various embodiments, the cancer includes cells that have a mutation or defect in the Rb:Raf-1 pathway. In certain embodiments, the cancer is osteosarcoma, promyelocytic leukemia, non-small cell lung cancer, epithelial lung carcinoma, pancreatic carcinoma, pancreatic ductal adenocarcinoma, glioblastoma, metastatic breast cancer, melanoma, or prostate cancer.

In various embodiments, the non-cancerous cell proliferation disorder includes cells that have a mutation or defect in the Rb:Raf-1 pathway. A non-cancerous cell proliferation disorder can include, for example, smooth muscle cell proliferation, systemic sclerosis, cirrhosis of the liver, adult respiratory distress syndrome, idiopathic cardiomyopathy, lupus erythematosus, retinopathy, cardiac hyperplasia, benign prostatic hyperplasia, ovarian cysts, pulmonary fibrosis, endometriosis, fibromatosis, harmatomas, lymphangiomatosis, sarcoidosis, desmoid tumors, intimal smooth muscle cell hyperplasia, restenosis, vascular occlusion, hyperplasia in the bile duct, hyperplasia in the bronchial airways, hyperplasia in the kidneys of patients with renal interstitial fibrosis, psoriasis, Reiter's syndrome, pityriasis rubra pilaris, a hyperproliferative disorder of keratinization, or scleroderma.

Pharmaceutical Compositions and Formulations

Also included are pharmaceutical compositions comprising the disclosed compounds. A "pharmaceutical composition" comprises a disclosed compound, typically in conjunction with an acceptable pharmaceutical carrier as part of a pharmaceutical composition for administration to a subject. Suitable formulations for administration include, for example, injection compositions, infusion compositions, topical administration solutions, emulsions, capsules, creams, ointments, tablets, pills, lozenges, suppositories, depot preparations, implanted reservoirs, intravaginal rings, coatings on implantable medical devices (e.g., a stent), impregnation in implantable medical devices, and the like. Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/mL benzyl alcohol), phosphate-buffered saline, Hank's solution, Ringer's-lactate and the like. Methods for encapsulating compositions (such as in a coating of hard gelatin or cyclodextrasn) are known in the art (Baker, et al., "Controlled Release of Biological Active Agents", John Wiley and Sons, 1986).

For example, a sterile injectable composition such as a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Other examples of acceptable vehicles and solvents include mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives can be useful in the preparation of injectables, as well as natural pharmaceutically-acceptable oils, such as olive oil or castor oil, for example in their polyoxyethylated versions. Oil solutions or suspensions can also contain a long-chain alcohol diluent or dispersant, or carboxymethyl cellulose or similar dispersing agents.

A composition for oral administration, for example, can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

As used herein, the term "pharmaceutically acceptable" means that the materials (e.g., compositions, carriers, diluents, reagents, salts, and the like) are capable of administration to or upon a mammal with a minimum of undesirable physiological effects such as nausea, dizziness or gastric upset.

Mode of Administration

Formulation of the compound to be administered will vary according to the route of administration selected, e.g., parenteral, oral, buccal, epicutaneous, inhalational, opthalamic, intraear, intranasal, intravenous, intraarterial, intramuscular, intracardiac, subcutaneous, intraosseous, intracutaneous, intradermal, intraperitoneal, topically, transdermal, transmucosal, intraarticular, intrasynovial, intrasternal, intralesional, intracranial inhalational, insufflation, pulmonary, epidural, intratumoral, intrathecal, vaginal, rectal, or intravitreal administration.

An "effective amount" to be administered is the quantity of compound in which a beneficial outcome is achieved when the compound is administered to a subject or alternatively, the quantity of compound that possess a desired activity in vivo or in vitro. In the case of cell proliferation disorders, a beneficial clinical outcome includes reduction in the extent or severity of the symptoms associated with the disease or disorder and/or an increase in the longevity and/or quality of life of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of disorder. The skilled artisan will be able to determine appropriate dosages depending on these and other factors. The interrelationship of dosages for animals and humans (based on milligrams per meter squared of body surface) is described, for example, in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of the disclosed compounds can range from about 0.001 mg/kg to about 1000 mg/kg, more preferably 0.01 mg/kg to about 500 mg/kg, more preferably 1 mg/kg to about 200 mg/kg. Effective doses will also vary, as recognized by those skilled in the art, depending on the diseases treated, route of administration, excipient usage, and the possibility of co-usage with other therapeutic treatments such as use of other agents.

The disclosed compounds can be co-administered with anti-cancer agents or chemotherapeutic agents such as alkylating agents, antimetabolites, natural products, hormones, metal coordination compounds, or other anticancer drugs. Examples of alkylating agents include nitrogen mustards (e.g., cyclophosphamide), ethylenimine and methylmelamines (e.g., hexamethylmelamine, thiotepa), alkyl sulfonates (e.g., busulfan), nitrosoureas (e.g., streptozocin), or triazenes (decarbazine, etc.). Examples of antimetabolites include folic acid analogs (e.g., methotrexate), pyrimidine analogs (e.g., fluorouracil), purine analogs (e.g., mercaptopurine). Examples of natural products include vinca alkaloids (e.g., vincristine), epipodophyllotoxins (e.g., etoposide), antibiotics (e.g., doxorubicin,), enzymes (e.g., L-asparaginase), or biological response modifiers (e.g., interferon alpha). Examples of hormones and antagonists include adrenocorticosteroids (e.g., prednisone), progestins (e.g., hydroxyprogesterone), estrogens (e.g., diethlystilbestrol), antiestrogen (e.g., tamoxifen), androgens (e.g., testosterone), antiandrogen (e.g., flutamide), and gonadotropin releasing hormone analog (e.g., leuprolide). Other agents that can be used in the methods and with the compositions of the invention for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), or adrenocortical suppressants (e.g., mitotane).

In various embodiments compounds can be coadministered with compounds that can inhibit angiogenesis or inhibit angiogenic tubule formation include, for example, matrix metalloproteinase inhibitors (dalteparin, suramin), endothelial cell inhibitors (e.g., thalidomide, squalamine, 2-methoxyestradiol), inhibitors of angiogenesis activation (e.g., avastatin, endostatin), celecoxib and the like.

Methods

Chemistry. $^1$H NMR spectra were recorded using a Mercury 400 NMR spectrometer (Varian, Palo Alto, Calif.). $^{13}$C NMR spectra were recorded using Distortionless Enhancement by Polarization Transfer. Both $^1$H and $^{13}$C spectra were recorded using CDCl$_3$ or d$_6$-DMSO (dimethyl sulfoxide) as internal standard. Atmospheric pressure ionization (API) and electrospray (ES) mass spectra and accurate mass determinations were recorded using a time of flight (TOF) mass spectrometer (an Agilent/Hewlett Packard, Santa Clara, Calif.). High Performance Liquid Chromatography (HPLC) analysis was performed using a HPLC system equipped with a PU-2089 Plus quaternary gradient pump and a UV-2075 Plus UV-VIS detector (JASCO, Easton, Md.). Infra red spectra were recorded using a FTIR-4100 spectrometer (JASCO). Melting points were determined using a MEL-TEMP Electrothermal melting point apparatus and were uncorrected. Column chromatography was conducted using silica gel 63-200 mesh (Merck & Co., Whitehouse Station, N.J.). Silica thin layer chromatography (TLC) was conducted on pre-coated aluminum sheets (60 $F_{254}$, Merck & Co.).

Cell culture and transfection. The human promyelocytic leukemia cell line U937 was cultured in RPMI (Mediatech, Hernden, Va.) containing 10% fetal bovine serum (FBS; Mediatech). U2-OS, Saos-2, MCF7, PANC1 and MDA-MB-231 cell lines were cultured in Dulbecco modified Eagle Medium (DMEM; Mediatech) containing 10% FBS. A549 cells and A549 shRNA Rb cell lines were maintained in Ham F-12K supplemented with 10% FBS. ShRNA cells lines were maintained in media containing 0.5 μg/mL puromycin. H1650, PC-9 and Aspc1 cell line were cultured in RPMI (Gibco/Invitrogen, Carlsbad, Calif.) containing 10% FBS. PANC1 and CAPAN2 pancreatic cell lines and the A375 Melanoma cell line was grown in DMEM supplemented with 10% FBS. Human aortic endothelial cells (HAECs, Clonetics, San Diego, Calif.) were cultured in endothelial growth medium, supplemented with 5% FBS, according to the manufacturer's instructions. U251MG and U87MG glioma cell lines were maintained in DMEM supplemented with non-essential amino acids, 50 mM (β-mercaptoethanol, and 10% FBS. ShRNA cell lines were made by stably transfecting A549 cells with two different shRNA constructs that specifically target Rb obtained from a library. The adenovirus (Ad) constructs Ad-green fluorescent protein (GFP) and Ad-E2F1 were obtained from W.D. Cress. Ad-cyclin D was provided by I. Cozar-Castellano.

In vitro library screening assays. Enzyme Linked ImmunoSorbent Assay (ELISA) 96-well plates were coated with 1 µg/mL of a glutathione S-transferase (GST) Raf-1 (1-149aa) overnight at 4° C. Subsequently the plates were blocked and GST Rb at 20 µg/mL was rotated at room temperature (RT) for 30 minutes in the presence or absence of the compounds at 20 micromolar (µM). GST-Rb +/− compounds were then added to the plate and incubated for 90 minutes (min) at 37° C. The amount of Rb bound to Raf-1 was detected by Rb polyclonal antibody (Santa Cruz Biotechnology, Santa Cruz, Calif.) 1:1000 incubated for 60 min at 37° C. Donkey-anti-rabbit-IgG-HRP (1:10,000) was added to the plate and incubated at 37° C. for 60 minutes. The color was developed with orthophenylenediamine (Sigma, St. Louis, Mo.) and the reaction was terminated with 3 molar (M) $H_2SO_4$. Absorbance was read at 490 nanometers (nm). To determine disruption of Rb to E2F1, Phb, or HDAC1 the above protocol was used with the exception of coating GST Rb on the ELISA plate and adding the drugs in the presence or absence of GST E2F1, Phb, or HDAC1. E2F1 monoclonal antibody (1:2000) was used to detect the amount of Rb bound to E2F1. Prohibitin monoclonal antibody was used at 1:1000 to detect the amount of Rb bound to Prohibitin. For disruption of MEK-Raf-1 binding ELISAs, Raf-1 1 microgram/milliliter (µg/mL) was coated on the plate and GST-MEK (20 µg/mL) was incubated +/− the compounds for 30 minutes at room temperature. Mek1 polyclonal antibody was used at 1:1000 to detect the binding of Raf-1 to Mek1. The $IC_{50}$ concentrations for the Rb:Raf-1 inhibitors were determined by plotting with Origin 7.5 software (Origin, Northampton, Mass.).

In vitro binding assays. Glutathione S-transferase (GST) fusion of Rb, Raf-1, E2F1, and MEK1 have been previously described (Dasgupta P, Sun J, Wang S, et al. Mol Cell Biol 2004; 24(21):9527-9541). First, 200 micrograms (µg) of U937 asynchronous lysates were pre-incubated with 10 µM of the indicated drugs or 1 µM of the Raf-1 peptide for 30 minutes at 4° C. Next, 200 µg of the U937 lysates were incubated with glutathione beads carrying an equal amount of the GST fusion proteins in 200l of protein binding buffer (20 mM Tris [pH 7.5], 50 mM KCL, 0.5 mM EDTA, 1 mM dithiothreitol, 0.5% NP-40, 3 mg of bovine serum albumin/mL) at 4° C. for 2 h. (Wang S, Ghosh R, Chellappan S. Mol Cell Biol 1998; 18(12):7487-7498).

Matrigel assays. Matrigel (Collaborative Biomedical Products) was used to promote the differentiation of HAECs into capillary tube-like structures (Dasgupta P, Sun J, Wang S, et al. Mol Cell Biol 2004; 24(21):9527-9541). A total of 100 µl of thawed Matrigel was added to 96-well tissue culture plates, followed by incubation at 37° C. for 60 minutes to allow polymerization. Subsequently, $1 \times 10^4$ HAECs were seeded on the gels in EGM medium supplemented with 5% FBS in the presence or absence of 20µM concentrations of the indicated compounds, followed by incubation for 24 hours at 37° C. Capillary tube formation assessed by using a Leica DMIL phase contrast microscope.

Lysate preparation, pmmunoprecipitation, and pestern plotting. Lysates from cells treated with different agents were prepared by NP-40 lysis as described earlier (Wang 1998). Tumor lysates were prepared with T-Per tissue lysis buffer (Pierce) and a Fischer PowerGen 125 dounce homogenizer. Physical interaction between proteins in vivo was analyzed by immunoprecipitation—Western blot analyses with 200 µg of lysate with 1 µg of the indicated antibody as previously described (Wang 1998). Polyclonal E2F1 and Cyclin D were obtained from Santa Cruz Biotechnology. Monoclonal Rb and Raf-1 were supplied by BD Transduction laboratories (San Jose, Calif.). Polyclonal antibodies to phospho-Rb (807,811) phospho-MEK1/2, MEK1/2, phospho-Erk1/2 and ERK1/2 were supplied by Cell Signaling (Danvers, Mass.).

Chromatin immunoprecipitation (ChIP) assay. A549 cells were rendered quiescent by serum starvation and re-stimulated with serum for 2h or 16h in the presence or absence of RRD 251 at 20µM. Cells were cross-linked with 1% formaldehyde for 10 minutes at room temperature. Subsequently, the cells were harvested and lysates were prepared. Immunoprecipitations were analyzed for the presence of E2F1, Rb, Raf-1, Brg1, HP1, and HDAC1 by PCR as previously described (Dasgupta 2004). Rabbit anti-mouse secondary antibody was used as the control for all reactions. The sequences of the PCR primers used in the PCRs were as follows: Cdc6 promoter (forward primer), 5'- GGCCT-CACAG CGACTCTAAGA-3' (SEQ ID NO:1); and Cdc6 promoter (reverse primer), 5'-CTCGGACTCACCA-CAAGC-3' (SEQ ID NO:2). TS promoter (forward primer), and 5'-GAC GGA GGC AGG CCA AGT G-3' SEQ ID NO:3) TS promoter (reverse primer). The cdc25A and c-fos primers are described in (Dasgupta, 2004).

In vitro kinase assay. The kinase reaction for Raf-1 was carried out with 100 nanograms (ng) of Raf-1 (Upstate Signaling, Charlottesville, Va.), 0.5 µg of full-length Rb protein (QED Bioscience, San Diego, Calif.) as the substrate, 10 µM ATP, 10 µCi of [$\gamma$-$^{32}$P] ATP in the kinase assay buffer in the presence or absence of the drugs at 30° C. for 30 minutes. Cyclin D and E kinase assays are described in (Dasgupta 2004).

Proliferation assays. Bromodeoxyuridine (BrdU) labeling kits were obtained from Roche Biochemicals (Indianapolis, Ind.). Cells were plated in poly-D-lysine coated chamber slides at a density of 10,000 cells per well and rendered quiescent by serum starvation for 24 hours. Cells were then re-stimulated with serum in the presence or absence of the indicated drugs for 18 h. S-phase cells were visualized by microscopy and quantitated by counting 3 fields of 100 in quadruplicate.

Soft Agar Assay. Soft agar assays were done in triplicate in 12-well plates (Corning, Corning N.Y.). First, the bottom layer of agar (0.6%) was allowed to solidify at room temperature. Next the top layer of agar was (0.3%) was mixed with 5,000 cells per well and the indicated drug. The drugs were added twice weekly in complete media to the agar wells. Colonies were quantified by staining with MTT (3-(4,5-Dimethylthiazol-2-yl)-2,5-diphenyltetrazolium bromide) 1 mg/mL for 1 hour at 37° C.

Animal Studies. Nude mice (Charles River, Wilminton, Mass., USA) were maintained in accordance with Institutional Animal Care and Use Committee (IAUCUC) procedures and guidelines. A549 cells were harvested and resuspended in PBS, and then injected s.c. into the right and left flanks ($10 \times 10^6$ cells per flank) of 8-week old female nude mice as reported previously (Sun 99). When tumors reached about 100-200 mm$^3$, animals were dosed intraperitoneally i.p. or orally by gavage with 0.1 mL solution once daily. Control animals received a vehicle, whereas treated animals were given 3a or RRD-238a at the indicated doses. The tumor volumes were determined by measuring the length (l) and the width (w) and calculating the volume ($V=lw^2/2$) as described previously (Sun 99). Statistical significance between control and treated animals were evaluated using Student's t-test.

Immunohistochemistry staining. Upon termination of xenograft anti-tumor experiments, tumors were removed and fixed in 10% neutral-buffered formalin before processing into paraffin blocks. Tissue sections (5 micrometers (μm) thick) were cut from the blocks and stained with Ki-67, CD31, TUNEL, and phospho-Rb antibodies. Paraffin sections were rehydrated to PBS and processed using the following protocols. Sections were rinsed in dH$_2$O, and then subjected to microwave 'antigen retrieval' for 20 minutes on 70% power, with a 1 minute cooling period after every 5 minutes, in 0.01 M sodium citrate, pH 6.0 (Janssen P J, Brinkmann A O, Boersma W J, Van der Kwast T H. J Histochem Cytochem 1994; 42(8):1169-75; Shi S R, Key M E, Kalra K L. J Histochem Cytochem 1991; 39(6):741-748). Sections were cooled for 20 minutes, rinsed 3 times in dH$_2$O, twice in PBS and incubated in 5% normal goat serum for 30 minutes. Sections were incubated in primary antibody for 1 hour in 5% normal goat serum, rinsed 3 times in PBS. For color development the slides were treated with ABC kit (Vector Labs, Burlingame, Calif.) rinsed in dH$_2$O, and developed using DAB as chromogen. After a final rinse in dH$_2$O, sections were lightly counterstained in hematoxylin, dehydrated, cleared and coverslipped. Tissue sections were stained with hematoxylin and eosin (H&E) using standard histological techniques. Tissue sections were also subjected to immunostaining for CD31 (BD Biosciences, San Diego, Calif., USA) using the avidin-biotin peroxidase complex technique. Mouse monoclonal antibody was used at 1:50 dilution following microwave antigen retrieval (four cycles of 5 min each on high in 0.1 M citrate buffer). Apoptotic cells were detected using DeadEnd Colorimetric TUNEL system (Promega, Madison, Wis.).

EXAMPLE 1

Identification, Design, and Synthesis of Disclosed Compounds

A screen was developed to identify small molecule inhibitors of the Rb:Raf-1 interaction. A diversity set, comprising 1981 compounds (National Cancer Institute, Bethesda, Md.) was examined using a glutathione S-transferase-retinoblastoma/glutathione S-transferase-Raf-1 kinase Enzyme-Linked ImmunoSorbent Assay screen (GST-Rb/GST-Raf-1 ELISA). Two structurally related compounds (1) and (2) were discovered that strongly inhibited the Rb:Raf-1 interaction at a concentration of 20 μM (100% for 1 and 95% for 2):

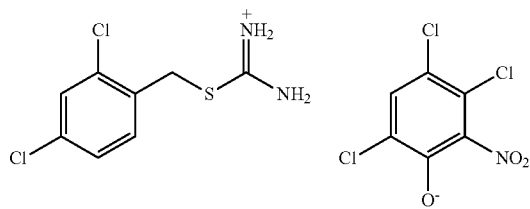

NSC-35400

(1)

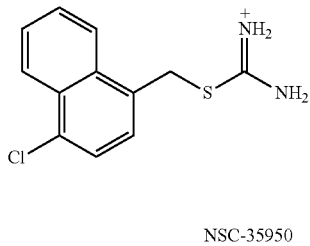 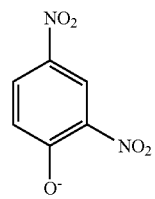

NSC-35950

(2)

A library of small molecule inhibitors of Rb:Raf-1 binding based on the hits 1 and 2 were designed, synthesized, and assessed for biological activity.

To determine the effects of various phenyl substituents on the ability to inhibit Rb:Raf-1 binding, several benzylisothiourea derivatives 3, lacking substitution at the α benzylic position, were prepared in good yields by reaction of thiourea with the appropriate benzyl halide (Scheme 1, Table 2). (Yong 1997) This method allowed us to rapidly generate a small library of benzylisothioureas, since a number of substituted benzyl halides are commercially available. When not commercially available the desired benzyl halides were obtained from the corresponding benzyl alcohols prepared when necessary by NaBH$_4$ reduction of the corresponding aldehyde) followed by reaction with thionyl chloride to generate the corresponding benzyl chloride. The corresponding benzylisothiourea derivatives 3 were usually obtained in good to quantitative yields.

To evaluate the importance of the benzylic position to activity, the benzylisothiouronium derivatives 4 bearing an alkyl group at the benzylic position were prepared by the reaction of thiourea with the appropriate α-substituted benzyl halides (Scheme 1, Table 1). (Yong 1997) The α-substituted benzyl halides were prepared by addition of an alkylmagnesium bromide to the appropriate benzaldehyde, followed by treatment of the intermediate alcohol with thionyl chloride.

The aryl methyl-, and hetero aryl methyl-thioureas 5 were obtained in moderate to good yields from thiourea and the appropriate benzyl halide (Scheme 1, Table 3) in a similar fashion to the benzylisothiourea derivatives 3.

To determine the importance of the isothiourea sulfur atom, the benzylguanidinium salts 6 (Scheme 1, Table 4) were obtained via the reaction between di-tert-butoxycarbonyl thiourea and the appropriate benzylamine, (Yong 1997) followed by deprotection of the corresponding di-tert-butoxycarbonyl guanidine product with tin(IV) chloride (Miel 1997) or trifluoroacetic acid, (Guisado 2002) in moderate to good yields. The condensation of α-halo ketones and thiourea, or methylthiourea, was carried out efficiently under microwave irradiation conditions to afford good to quantitative yields of aminothiazolium salts of type 7 (Scheme 2, Table 5). Similarly, the condensation of α-halo ketones and dimethylthiourea under microwave conditions afforded good yields of the aminothiazolium quaternary salts of type 8 (Scheme 2, Table 6). A further set of analogues of the isothioureas was obtained by reaction of various thio-functionalized heterocycles (3-mercaptotriazole, 5-amino-3-mercaptotriazole, 2-mercaptobenzoimidazole, 2-mercaptoimidazole, and 4,5-dihydro-2-mercaptoimidazole) with 4-chlorobenzyl chloride or 2,4-dichlorobenzyl chloride. The corresponding products 9a-d were obtained in good to quantitative yield (Scheme 3, Table 7).

Scheme 1.

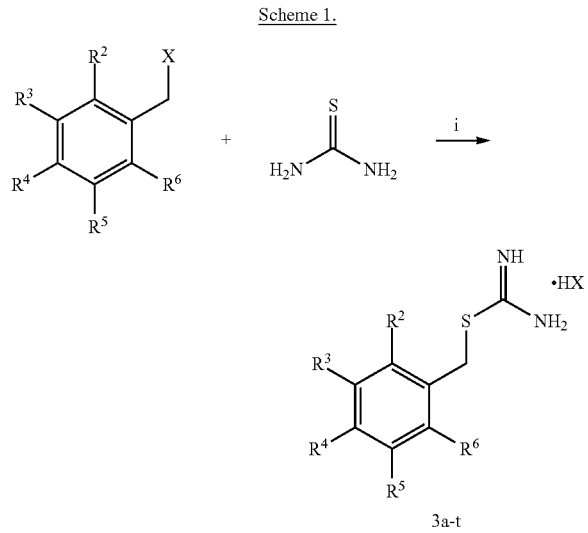

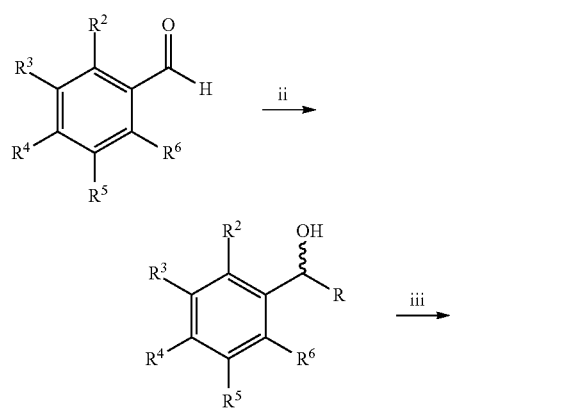

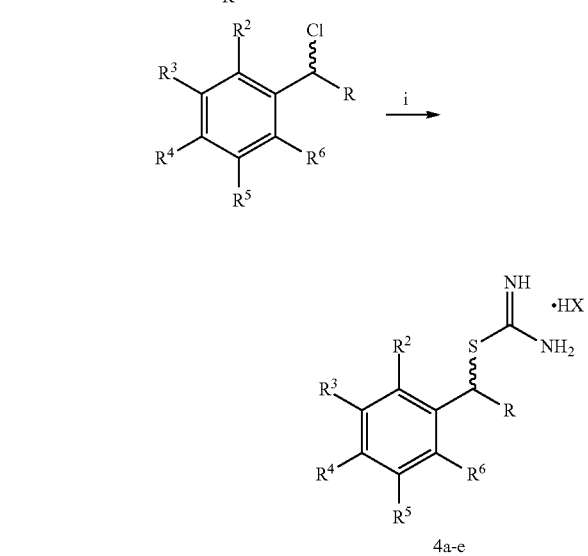

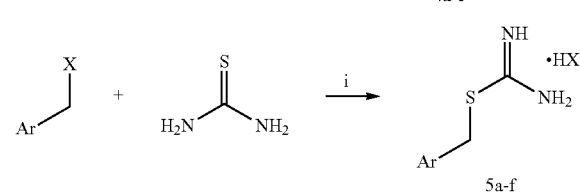

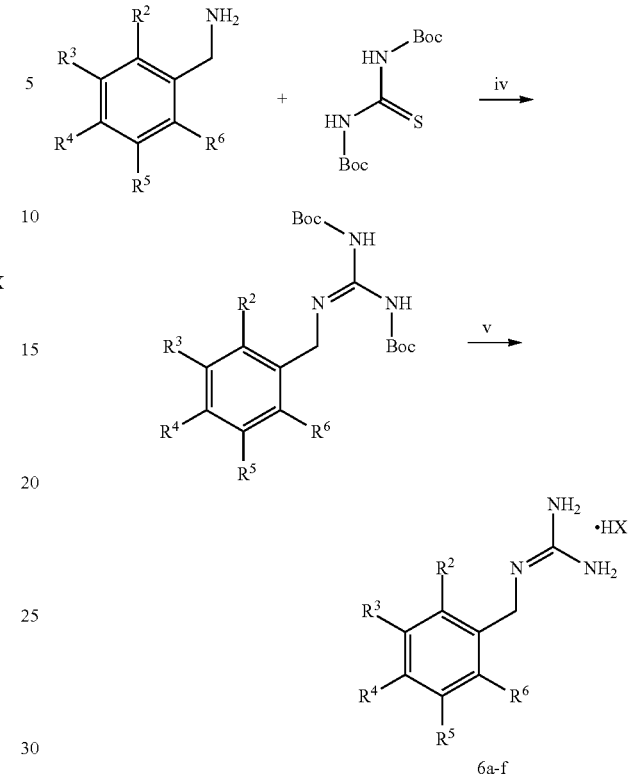

Reagents and Conditions: i. ethanol, 100° C., 1-2 hours, or microwave irradiation, 100° C., 10 minutes, 100 Watts; ii. RCH$_2$MgBr, tetrahydrofuran or diethyl ether, reflux, 1 hour, iii. Toluene, thionyl chloride, 100° C., 2-10 hours; iv. Mukaiyama's reagent (1-methyl-2-chloropyridinium iodide), triethylamine, dimethylformamide, room temperature, 20 minutes; v. CF$_3$CO$_2$H, dichloromethane, room temperature, overnight or SnCl$_4$, ethyl acetate, room temperature, overnight.

Scheme 2.

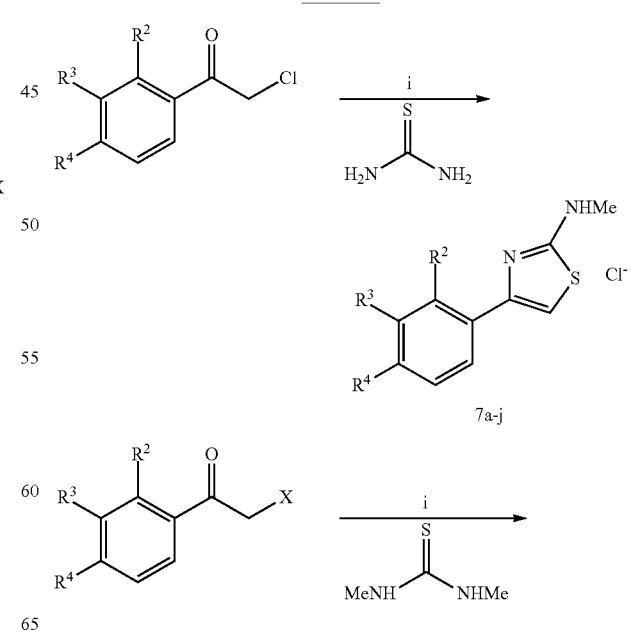

-continued

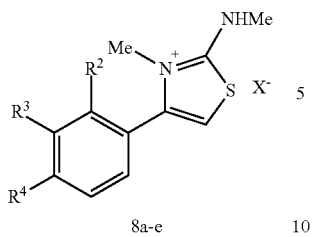

8a-e

Reagents and Conditions: i. ethanol, microwave irradiation, 100° C., 10 minutes, 100 Watts.

Scheme 3.

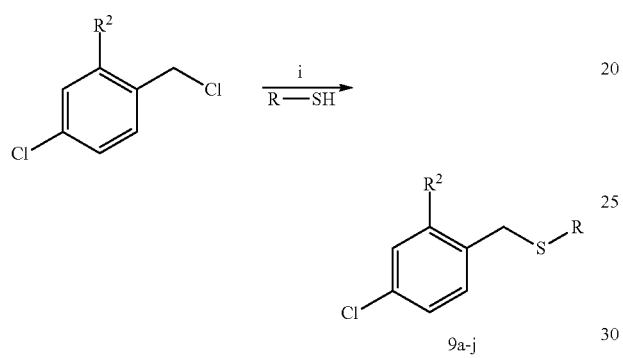

Reagents and Conditions: i. ethanol, microwave irradiation, 100° C., 10 minutes, 100 Watts.

EXAMPLE 2

General Procedure for the Synthesis of Compounds 3a-t

A 10 milliliter (mL) microwave reaction tube was charged with the benzyl halide (1.0 millimole, mmol) and thiourea (76 mg, 1.0 mmol) in ethanol (1.5 mL). The tube was capped and irradiated in the microwave reactor (single-mode CEM Discover™ system, CEM, Matthews, N.C.) at 100° C. for 15 minutes. The solid was filtered and solid washed with cold ethanol. The solid product was dried under high vacuum to give the product.

EXAMPLE 3

General Procedure for the Synthesis of Compounds 7a-j and 8a-e

A 10 mL microwave reaction tube was charged with a mixture of the appropriate α-haloacetophenone (1.0 mmol) and thiourea (76 mg, 1.0 mmol) in ethanol (2.0 mL). The tube was capped and irradiated in the microwave synthesizer actor (single-mode CEM Discover™ system) at 120° C. for 10 minutes. The solid formed was filtered on a sintered funnel, washed with cold ethyl acetate and finally dried in vacuo.

Compound Analytical Data

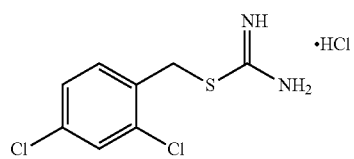 [SMILES: N=C(N)SCc1ccc(Cl)cc1Cl ; Cl]

3a—White solid, mp 222-223° C.; $^1$H NMR (400 MHz, d$_6$-DMSO) δ 4.58 (s, 2H), 7.47 (dd, J=8.0 and 2.0 Hz, 1H), 7.63 (d, J=8.0 Hz, 1H), 7.70 (d, J=2.0 Hz, 1H), 9.31 (br s, 2H), 9.39 (br s, 2H); $^{13}$C NMR (100 MHz, d$_6$-DMSO) δ 32.6, 128.5, 130.0, 132.5, 133.3, 134.5, 135.1, 169.4; MS (ESI) m/z 235.0 (100%, [M+H]$^+$); HRMS calcd for C$_8$H$_9$Cl$_2$N$_2$S: 234.9858; observed: 234.9854; HPLC analysis (Alltech C18): 90% methanol, 10% acetonitrile, flow rate 0.5 mL/min: t$_R$ 3.26 min. 90% acetonitrile, 10% water, flow rate 0.75 mL/min: t$_R$ 2.05 min. 100% methanol, flow rate 0.5 mL/min: t$_R$ 3.05 min.

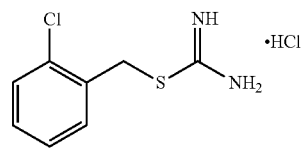 [SMILES: N=C(N)SCc1ccccc1Cl ; Cl]

3b—White solid, mp 199-200° C. $^1$H NMR (400 MHz, d$_6$-DMSO) δ δ 4.61 (s, 2H), 7.34-7.39 (m, 2H), 7.49-7.51 (m, 1H), 7.60-7.63 (m, 1H), 9.38 (br s, 2H), 9.46 (br s, 2H); MS (ESI) m/z 201.0 (100%, [M+H]$^+$); HRMS calcd for C$_8$H$_{10}$ClN$_2$S: 201.0247; observed: 201.0250; HPLC analysis (Alltech C18): 90% methanol, 10% acetonitrile, flow rate 0.5 mL/min: t$_R$ 2.85 min; 90% acetonitrile, 10% water, flow rate 0.75 mL/min: t$_R$ 1.86 min.

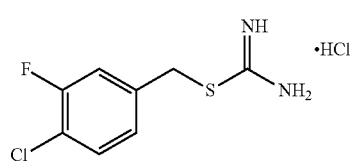 [SMILES: N=C(N)SCc1ccc(Cl)c(F)c1 ; Cl]

3c—Light yellow solid, mp 203-204° C. $^1$H NMR (400 MHz, d$_6$-DMSO) δ 4.42 (s, 2H), 7.23 (d, J=8.0 Hz, 1H), 7.33 (d, J=8.0 Hz, 1H), 7.47 (t, J=8.0 Hz, 1H); MS (ESI) m/z 219.0 (100%, [M+H]$^+$); HRMS calcd for C$_8$H$_9$ClFN$_2$S: 219.0153; observed: 219.0157; HPLC analysis (Alltech C18): 90% methanol, 10% acetonitrile, flow rate 0.5 mL/min: t$_R$ 2.90 min; 90% acetonitrile, 10% water, flow rate 0.75 mL/min: t$_R$ 2.08 min.

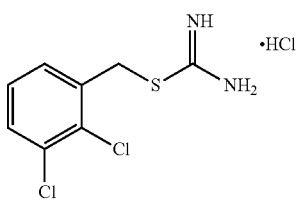 [SMILES: N=C(N)SCc1cccc(Cl)c1Cl ; Cl]

3d—White solid, mp 253-254° C. $^1$H NMR (400 MHz, d$_6$-DMSO) δ 4.64 (s, 2H), 7.41 (t, J=8.0 Hz, 1H), 7.58 (dd, J=8.0 and 1.6 Hz, 1H), 7.67 (dd, J=8.0 and 1.6 Hz, 1H), 9.31 (br s, 4H); MS (ESI) m/z 234.9 (100%, [M+H]$^+$); HRMS calcd for C$_8$H$_9$Cl$_2$N$_2$S: 234.9858; observed: 234.9859; HPLC analysis (Alltech C18): 90% methanol, 10% acetonitrile, flow rate 0.5 mL/min: t$_R$ 3.08 min; 90% acetonitrile, 10% water, flow rate 0.75 mL/min: t$_R$ 2.05 min.

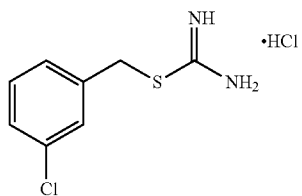 [SMILES: N=C(N)SCc1cccc(Cl)c1 ; Cl]

3e—White solid, mp 191-192° C. $^1$H NMR (400 MHz, d$_4$-MeOH) δ 4.42 (s, 2H), 7.35-7.37 (m, 3H), 7.46 (s, 1H); MS (ESI) m/z 201.0 (100%, [M+H]$^+$); HRMS calcd for C$_8$H$_{10}$ClN$_2$S: 201.0247; observed: 201.0248; HPLC analysis (Alltech C18): 90% methanol, 10% acetonitrile, flow rate 0.5 mL/min: t$_R$ 2.85 min; 90% acetonitrile, 10% water, flow rate 0.75 mL/min: t$_R$ 2.01 min.

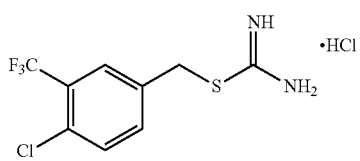 [SMILES: N=C(N)SCc1ccc(Cl)c(C(F)(F)F)c1 ; Cl]

3f—Pale yellow solid, mp 163-164° C. $^1$H NMR (250 MHz, d$_4$-MeOH) δ 4.49 (s, 2H), 7.64 (d, J=8.0 Hz, 1H), 7.67 (dd, J=8.0 and 2.0 Hz, 1H), 7.86 (d, J=2.0 Hz, 1H); MS (ESI) m/z 269.0 (100%, [M+H]$^+$); HRMS calcd for C$_9$H$_9$ClF$_3$N$_2$S: 269.0121; observed: 269.0123; HPLC analysis (Alltech C18): 90% methanol, 10% acetonitrile, flow rate 0.5 mL/min: t$_R$ 3.18 min; 90% acetonitrile, 10% water, flow rate 0.75 mL/min: t$_R$ 2.11 min.

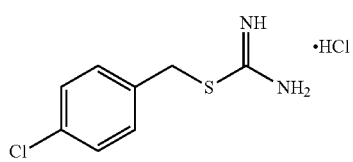 [SMILES: N=C(N)SCc1ccc(Cl)cc1 ; Cl]

3g—White plates, mp 171-172° C. $^1$H NMR (400 MHz, d$_6$-DMSO) δ 4.57 (s, 2H), 7.40 (dd, J=6.8 and 1.6 Hz, 2H), 7.46 (dd, J=6.8 and 1.6 Hz, 2H), 9.33 (br s, 2H), 9.46 (br s, 2H); $^{13}$C NMR (100 MHz, d$_6$-DMSO) 39.7, 129.3 (2C), 131.5 (2C), 133.3, 135.3, 169.6; MS (ESI) m/z 201.0 (100%, [(M+H)]$^+$); HRMS calcd for C$_8$H$_{10}$N$_2$SCl: 201.0247; observed: 201.0247; HPLC analysis (Alltech C18): 90% methanol, 10% acetonitrile, flow rate 0.5 mL/min: t$_R$ 3.03 min; 90% acetonitrile, 10% water, flow rate 0.75 mL/min: t$_R$ 1.95 min.

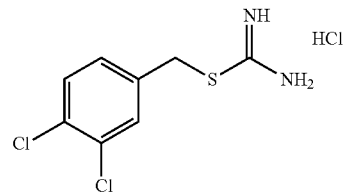 [SMILES: N=C(N)SCc1ccc(Cl)c(Cl)c1 ; Cl]

3h—White solid, mp 240-241° C. $^1$H NMR (400 MHz, d$_6$-DMSO) δ 4.39 (s, 2H), 7.34 (dd, J=8.0 and 2.0 Hz, 1H), 7.53 (d, J=8.0 Hz, 1H), 7.60 (d, J=2.0 Hz, 1H); MS (ESI) m/z 234.9 (100%, [M+H]$^+$); HRMS calcd for C$_8$H$_9$Cl$_2$N$_2$S: 234.9858; observed: 234.9860; HPLC analysis (Alltech C18): 90% methanol, 10% acetonitrile, flow rate 0.5 mL/min: t$_R$ 2.83 min; 90% acetonitrile, 10% water, flow rate 0.75 mL/min: t$_R$ 1.88 min.

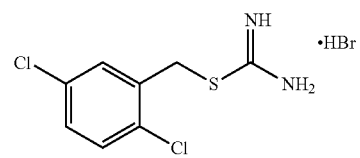 [SMILES: N=C(N)SCc1cc(Cl)ccc1Cl ; Br]

3i—White solid, mp 218-219° C. $^1$H NMR (400 MHz, d$_6$-DMSO) δ 4.49 (s, 2H), 7.37 (dd, J=8.4 and 2.0 Hz, 1H), 7.46 (d, J=8.4 Hz, 1H), 7.55 (d, J=2.0 Hz, 1H); MS (ESI) m/z 234.9 (100%, [M+H]$^+$); HRMS calcd for C$_8$H$_9$Cl$_2$N$_2$S: 234.9858; observed: 234.9859; HPLC analysis (Alltech C18): 90% methanol, 10% acetonitrile, flow rate 0.5 mL/min: t$_R$ 2.80 min; 90% acetonitrile, 10% water, flow rate 0.75 mL/min: t$_R$ 1.98 min.

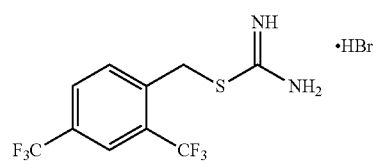

3j—White solid, mp 233-234° C. $^1$H NMR (400 MHz, d$_4$-MeOH) δ 4.67 (s, 2H), 7.91 (d, J=8.0 Hz, 1H), 8.01 (d, J=8.0 Hz, 1H), 8.03 (s, 1H); MS (ESI) m/z 303.0 (100%, [M+H]$^+$); HRMS calcd for C$_{10}$H$_9$F$_6$N$_2$S: 303.0391; observed: 303.0391; HPLC analysis (Alltech C18): 90% methanol, 10% acetonitrile, flow rate 0.5 mL/min: t$_R$ 2.66 min; 90% acetonitrile, 10% water, flow rate 0.75 mL/min: t$_R$ 2.83 min.

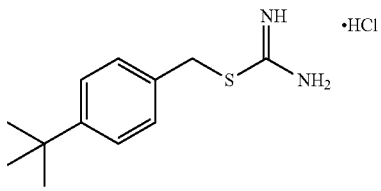

3k—White solid, mp 234-235° C. $^1$H NMR (400 MHz, d$_4$-MeOH) δ 1.33 (s, 9H), 4.43 (s, 2H), 7.39 (d, J=11.0 Hz, 2H), 7.43 (d, J=11.0 Hz, 2H); $^{13}$C NMR (100 MHz, d$_6$-DMSO) 31.7 (3C), 34.4, 34.9, 126.2 (2C), 129.4 (2C), 132.7, 151.0, 170.0; MS (ESI) m/z 241.2 (20%, [(M+NH$_4$)]$^+$), 102.1 (100%). HRMS calcd for C$_{12}$H$_{19}$N$_2$S: 223.1263; observed: 223.1259; HPLC analysis (Alltech C18): 90% methanol, 10% acetonitrile, flow rate 0.5 mL/min: t$_R$ 3.11 min; 90% acetonitrile, 10% water, flow rate 0.75 mL/min: t$_R$ 2.08 min.

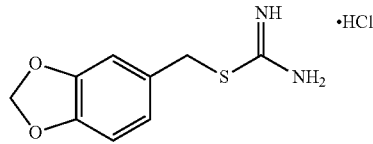 [SMILES: N=C(N)SCc1ccc2c(c1)OCO2 ; Cl]

3l—Brown solid, mp 158-159° C. $^1$H NMR (400 MHz, d$_6$-DMSO) δ 4.35 (s, 2H), 5.96 (s, 2H), 6.80 (d, J=8.0 Hz, 1H), 6.88 (dd, J=8.0 and 1.6 Hz, 1H), 6.90 (d, J=2.0 Hz, 1H); MS (ESI) m/z 211.0 (100%, [M+H]$^+$), 135.0 (14%, [M-CH$_3$N$_2$S]$^+$); HRMS calcd for C$_9$H$_{11}$N$_2$O$_2$S: 211.0535; observed: 211.0539; HPLC analysis (Alltech C18): 90% methanol, 10% acetonitrile, flow rate 0.5 mL/min: t$_R$ 2.93 min; 90% acetonitrile, 10% water, flow rate 0.75 mL/min: t$_R$ 1.95 min.

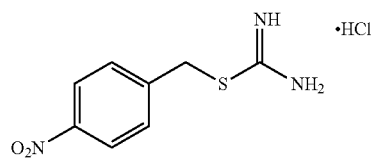 [SMILES: N=C(N)SCc1ccc([N+](=O)[O-])cc1 ; Cl]

3m—White solid, mp 227-228° C. $^1$H NMR (400 MHz, d$_6$-DMSO) δ 4.72 (s, 2H), 7.71 (d, J=9.2 Hz, 2H), 8.19 (d, J=9.2 Hz, 2H), 9.32 (br s, 2H), 9.52 (br s, 2H); $^{13}$C NMR (100 MHz, d$_6$-DMSO) δ 33.7, 124.4 (2C), 130.9 (2C), 144.4, 147.6, 169.3; MS (ESI) m/z 212.0 (100%, [M+H]$^+$); HRMS calcd for C$_8$H$_{10}$O$_2$N$_3$S: 212.0488; observed: 212.0489; HPLC analysis (Alltech C18): 90% methanol, 10% acetonitrile, flow rate 0.5 mL/min: t$_R$ 3.00 min; 90% acetonitrile, 10% water, flow rate 0.75 mL/min: t$_R$ 1.93 min.

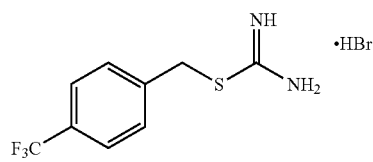

3n—Colorless solid, mp 206-207° C. $^1$H NMR (400 MHz, d$_4$-MeOH) δ 4.54 (s, 2H), 7.39 (d, J=8.2 Hz, 2H), 7.43 (d, J=8.2 Hz, 2H); MS (ESI) m/z 235.0 (100%, [M+H]$^+$); HRMS calcd for C$_9$H$_{11}$F$_3$N$_2$S: 235.0511; observed: 235.0512; HPLC analysis (Alltech C18): 90% methanol, 10% acetonitrile, flow rate 0.5 mL/min: t$_R$ 2.80 min; 90% acetonitrile, 10% water, flow rate 0.75 mL/min: t$_R$ 1.85 min.

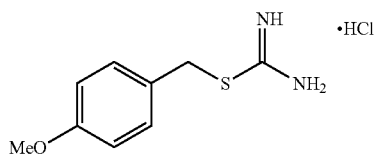 [SMILES: COc1ccc(CSC(=N)N)cc1 ; Cl]

3o—White solid, mp 148-149° C. $^1$H NMR (400 MHz, d$_6$-DMSO) δ 4.49 (s, 2H), 6.89 (d, J=4.8 Hz, 2H), 7.34 (d, J=4.8 Hz, 2H), 9.35 (br s, 4H); $^{13}$C NMR (100 MHz, d$_6$-DMSO) δ 34.5, 55.8, 114.8 (2 C), 127.0, 131.0 (2 C), 159.5, 170.0; MS (ESI) m/z 197.0 (18%, [M+H]$^+$), 121.0 (100%, [M-CH$_3$N$_2$S]$^+$); HRMS calcd for C$_9$H$_{13}$ON$_2$S: 197.0743; observed: 197.0733; HPLC analysis (Alltech C18): 90% methanol, 10% acetonitrile, flow rate 0.5 mL/min: t$_R$ 3.06 min; 90% acetonitrile, 10% water, flow rate 0.75 mL/min: t$_R$ 1.96 min.

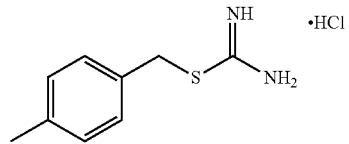

3p—Colorless solid, mp 161-162° C. $^1$H NMR (400 MHz, d$_4$-MeOH) δ 2.35 (s, 3H), 4.41 (s, 2H), 7.21 (d, J=8.0 Hz, 2H), 7.34 (d, J=8.0 Hz, 2H); MS (ESI) m/z 181.0 (100%, [M+H]$^+$); HRMS calcd for C$_9$H$_{13}$N$_2$S: 181.0794; observed: 181.0793; HPLC analysis (Alltech C18): 90% methanol, 10% acetonitrile, flow rate 0.5 mL/min: t$_R$ 3.03 min; 90% acetonitrile, 10% water, flow rate 0.75 mL/min: t$_R$ 2.00 min.

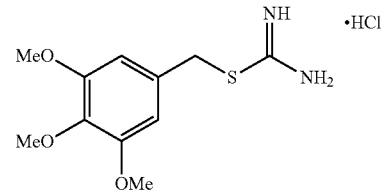 [SMILES: COc1cc(CSC(=N)N)cc(OC)c1OC ; Cl]

3q—Light brown solid, mp 172-173° C. $^1$H NMR (400 MHz, d$_4$-MeOH) δ 3.73 (s, 3H), 3.82 (s, 6H), 4.37 (s, 2H), 6.71 (s, 2H); MS (ESI) m/z 181.1 (100%, [M-CH$_3$N$_2$S]$^+$); HRMS calcd for C$_{11}$H$_{17}$N$_2$O$_3$S: 257.0954; observed: 257.0958; HPLC analysis (Alltech C18): 90% methanol, 10% acetonitrile, flow rate 0.5 mL/min: t$_R$ 2.66 min; 90% acetonitrile, 10% water, flow rate 0.75 mL/min: t$_R$ 4.21 min.

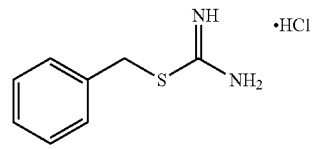 [SMILES: N=C(N)SCc1ccccc1 ; Cl]

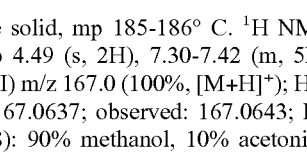

3r—White solid, mp 185-186° C. $^1$H NMR (400 MHz, d$_6$-DMSO) δ 4.49 (s, 2H), 7.30-7.42 (m, 5H), 9.22 (br s, 4H); MS (ESI) m/z 167.0 (100%, [M+H]$^+$); HRMS calcd for C$_8$H$_{11}$N$_2$S: 167.0637; observed: 167.0643; HPLC analysis (Alltech C18): 90% methanol, 10% acetonitrile, flow rate 0.5 mL/min: t$_R$ 2.98 min; 90% acetonitrile, 10% water, flow rate 0.75 mL/min: t$_R$ 1.80 min.

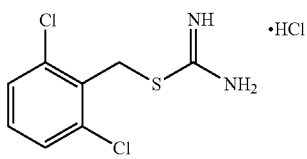 [SMILES: N=C(N)SCc1c(Cl)cccc1Cl ; Cl]

3s—White solid, mp 231-232° C. $^1$H NMR (400 MHz, d$_6$-DMSO) δ 4.67 (s, 2H), 7.42 (t, J=8.0 Hz, 1H), 7.54 (d, J=8.0 Hz, 2H), 9.51 (br s, 4H); $^{13}$C NMR (100 MHz, d$_6$-DMSO) 32.2, 129.7, 130.3, 132.0, 135.8, 169.9; MS (ESI) m/z 235.0 (100%, [M+H]$^+$); HRMS calcd for C$_8$H$_9$Cl$_2$N$_2$S: 234.9858; observed: 234.9855; HPLC analysis (Alltech C18): 90% methanol, 10% acetonitrile, flow rate 0.5 mL/min: t$_R$ 3.08 min. 90% acetonitrile, 10% water, flow rate 0.75 mL/min: t$_R$ 2.08 min.

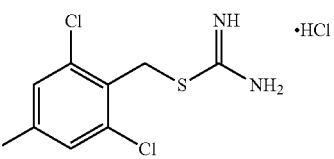

3t—White solid, mp 265-266° C. $^1$H NMR (400 MHz, d$_6$-DMSO) δ 4.64 (s, 2H), 7.79 (s, 2H), 9.45 (br s, 4H); MS (ESI) m/z 270.9 (100%, [M+H]$^+$); HRMS calcd for C$_8$H$_8$Cl$_3$N$_2$S: 268.9468; observed: 268.9469; HPLC analysis (Alltech C18): 90% methanol, 10% acetonitrile, flow rate 0.5 mL/min: t$_R$ 2.23 min; 90% acetonitrile, 10% water, flow rate 0.75 mL/min: t$_R$ 1.15 min.

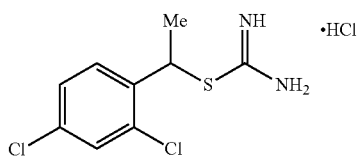 [SMILES: CC(SC(=N)N)c1ccc(Cl)cc1Cl ; Cl]

4a—Off-white solid, mp 153-154° C. $^1$H NMR (400 MHz, d$_6$-DMSO) δ 1.71 (d, J=6.8 Hz, 3H), 5.37 (q, J=6.8 Hz, 1H), 7.53 (dd, J=8.8 and 2.4 Hz, 1H), 7.69 (d, J=8.8 Hz, 1H), 7.72 (d, J=2.4 Hz, 1H), 9.18 (br s, 2H), 9.35 (br s, 2H); MS (ESI) m/z 248.9 (100%, [M+H]$^+$); HRMS calcd for C$_9$H$_{11}$Cl$_2$N$_2$S: 249.0014; observed: 249.0017; HPLC analysis (Alltech C18): 90% methanol, 10% acetonitrile, flow rate 0.5 mL/min: t$_R$ 3.26 min; 90% acetonitrile, 10% water, flow rate 0.75 mL/min: t$_R$ 2.18 min.

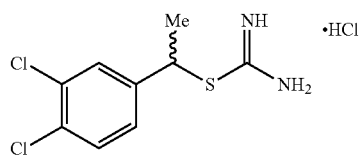 [SMILES: CC(SC(=N)N)c1ccc(Cl)c(Cl)c1 ; Cl]

4b—Beige solid, mp 108-109° C. $^1$H NMR (400 MHz, d$_4$-MeOH) δ 1.70 (d, J=7.2 Hz, 3H), 4.94 (q, J=7.2 Hz, 1H), 7.40 (dd, J=8.0 and 1.8 Hz, 1H), 7.56 (d, J=8.0 Hz, 1H), 7.64 (d, J=1.8 Hz, 1H); MS (ESI) m/z 249.0 (100%, [M+H]$^+$); HRMS calcd for C$_9$H$_{11}$Cl$_2$N$_2$S: 249.0014; observed: 249.0017; HPLC analysis (Alltech C18): 90% methanol, 10% acetonitrile, flow rate 0.5 mL/min: t$_R$ 2.68 min; 90% acetonitrile, 10% water, flow rate 0.75 mL/min: t$_R$ 1.83 min.

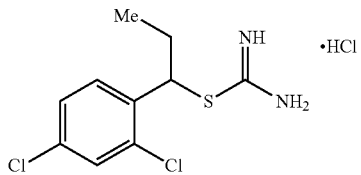 [SMILES: CCC(SC(=N)N)c1ccc(Cl)cc1Cl ; Cl]

4c—Yellow semisolid. $^1$H NMR (400 MHz, d$_6$-DMSO) δ 0.85 (t, J=7.2 Hz, 3H), 2.08 (sept, J=7.2 Hz, 2H), 5.24 (t, J=7.2 Hz, 1H), 6.85-7.25 (br s, 4H), 7.53 (dd, J=8.4 and 2.0 Hz, 1H), 7.64 (d, J=8.4 Hz, 1H), 7.72 (d, J=2.0 Hz, 1H); MS (ESI) m/z 263.0 (100%, [M+H]$^+$); HRMS calcd for C$_{10}$H$_{13}$Cl$_2$N$_2$S: 263.0176; observed: 263.0179; HPLC analysis (Alltech C18): 90% methanol, 10% acetonitrile, flow rate 0.5 mL/min: t$_R$ 3.15 min; 90% acetonitrile, 10% water, flow rate 0.75 mL/min: t$_R$ 2.11 min.

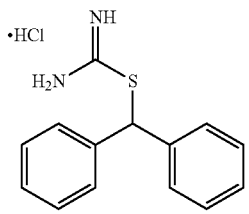 [SMILES: Cl ; N=C(N)SC(c1ccccc1)c1ccccc1]

4d—Off-white solid, mp 184-185° C. $^1$H NMR (400 MHz, d$_4$-MeOH) δ 6.25 (s, 1H), 7.31-7.45 (m, 6H), 7.46-7.53 (m, 4H); MS (ESI) m/z 243.1 (100%, [M+H]$^+$); HRMS calcd for C$_{14}$H$_{15}$N$_2$S: 243.0950; observed: 243.0953; HPLC analysis (Alltech C18): 90% methanol, 10% acetonitrile, flow rate 0.5 mL/min: t$_R$ 2.88 min; 90% acetonitrile, 10% water, flow rate 0.75 mL/min: t$_R$ 1.94 min.

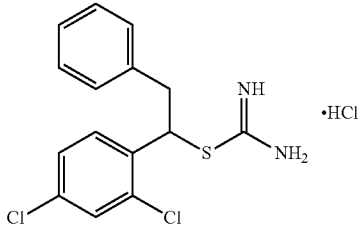 [SMILES: N=C(N)SC(Cc1ccccc1)c1ccc(Cl)cc1Cl ; Cl]

4e—White solid, mp>300° C. (dec.). $^1$H NMR (400 MHz, d$_4$-MeOH) δ 3.32 (d, J=7.6 Hz, 2H), 5.59 (t, J=7.6 Hz, 1H), 7.13-7.26 (m, 5H), 7.38 (dd, J=8.4 and 2.4 Hz, 1H), 7.43 (d, J=2.4 Hz, 1H), 7.67 (d, J=8.4 Hz, 1H); MS (ESI) m/z 325.0 (100%, [M+H]$^+$); HRMS calcd for C$_{15}$H$_{15}$Cl$_2$N$_2$S: 325.0327; observed: 325.0328; HPLC analysis (Alltech C18): 90% methanol, 10% acetonitrile, flow rate 0.5 mL/min: t$_R$ 3.23 min; 90% acetonitrile, 10% water, flow rate 0.75 mL/min: t$_R$ 2.18 min.

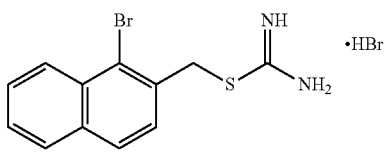 [SMILES: N=C(N)SCc1ccc2ccccc2c1Br ; Br]

5a—Off-white solid, mp 232-233° C. $^1$H NMR (250 MHz, d$_4$-MeOH) δ 4.85 (s, 2H), 7.60-7.73 (m, 3H), 7.95 (d, J=8.2 Hz, 2H), 8.33 (d, J=8.2 Hz, 2H); MS (ESI) m/z 295.0 (100%, [M+H]$^+$); HRMS calcd for C$_{12}$H$_{12}$BrN$_2$S: 294.9899; observed: 294.9896; HPLC analysis (Alltech C18): 90% methanol, 10% acetonitrile, flow rate 0.5 mL/min: $t_R$ 3.21 min; 90% acetonitrile, 10% water, flow rate 0.75 mL/min: $t_R$ 2.36 min.

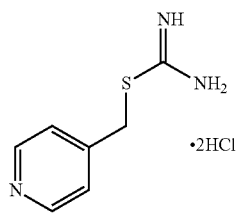 [SMILES: N=C(N)SCc1ccncc1 ; "·2HCl"]

5b—Yellow solid, mp 210-211° C. $^1$H NMR (400 MHz, d$_4$-MeOH) δ 4.84 (s, 2H), 8.15 (d, J=6.4 Hz, 2H), 8.87 (d, J=6.4 Hz, 2H); MS (ESI) m/z 168.0 (100%, [M+H]$^+$); HRMS calcd for C$_7$H$_{10}$N$_3$S: 168.0589; observed: 168.0592; HPLC analysis (Alltech C18): 90% methanol, 10% acetonitrile, flow rate 0.5 mL/min: $t_R$ 2.93 min; 90% acetonitrile, 10% water, flow rate 0.75 mL/min: $t_R$ 1.96 min.

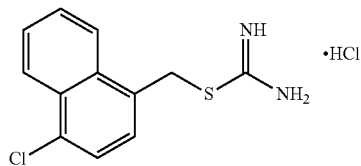 [SMILES: N=C(N)SCc1ccc(Cl)c2ccccc12 ; Cl]

5c—Off-white solid, mp 237-238° C. $^1$H NMR (400 MHz, d$_4$-MeOH) δ 4.93 (s, 2H), 7.57 (d, J=8.0 Hz, 1H), 7.61 (d, J=8.0 Hz, 1H), 7.70-7.73 (m, 2H), 8.19-8.21 (m, 1H), 8.33-8.36 (m, 1H); MS (ESI) m/z 251.0 (100%, [M+H]$^+$); HRMS calcd for C$_{12}$H$_{12}$ClN$_2$S: 251.0404; observed: 251.0405; HPLC analysis (Alltech C18): 90% methanol, 10% acetonitrile, flow rate 0.5 mL/min: $t_R$ 1.71 min; 90% acetonitrile, 10% water, flow rate 0.75 mL/min: $t_R$ 1.78 min.

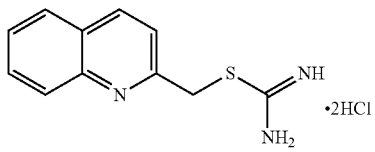 [SMILES: N=C(N)SCc1ccc2ccccc2n1]

5d—Brown solid, mp 204-205° C. $^1$H NMR (400 MHz, d$_4$-MeOH) 4.83 (s, 2H), 7.79-7.85 (m, 1H), 7.88-7.92 (m, 1H), 7.99-8.04 (m, 1H), 8.14-8.18 (m, 2H), 7.37 (dd, J=8.0 and 5.6 Hz, 1H) MS (ESI) m/z 218.0 (100%, [M+H]$^+$); HRMS calcd for C$_{11}$H$_{12}$N$_3$S: 218.0746; observed: 218.0751; HPLC analysis (Alltech C18): 90% methanol, 10% acetonitrile, flow rate 0.5 mL/min: $t_R$ 2.98 min; 90% acetonitrile, 10% water, flow rate 0.75 mL/min: $t_R$ 2.00 min.

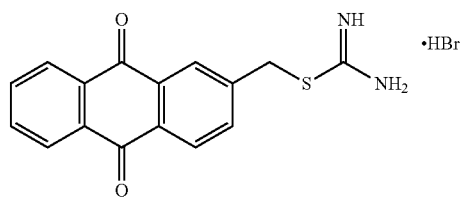 [SMILES: N=C(N)SCc1ccc2c(c1)C(=O)c1ccccc1C2=O ; Br]

5e—Off-white solid, mp 222-223° C. $^1$H NMR (400 MHz, d$_6$-DMSO) δ 4.68 (s, 2H), 7.90-7.94 (m, 3H), 8.18-8.21 (m, 3H), 8.26 (d, J=1.2 Hz, 1H), 9.01 (br s, 2H), 9.25 (br s, 2H); MS (ESI) m/z 297.0 (100%, [M+H]$^+$); HRMS calcd for C$_{16}$H$_{13}$O$_2$N$_2$S: 297.0692; observed: 297.0693; HPLC analysis (Alltech C18): 90% methanol, 10% acetonitrile, flow rate 0.5 mL/min: $t_R$ 4.83 min; 90% acetonitrile, 10% water, flow rate 0.75 mL/min: $t_R$ 3.00 min.

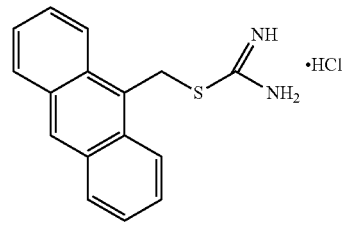 [SMILES: N=C(N)SCc1c2ccccc2cc2ccccc12 ; Cl]

5f—Yellow solid, mp 217-218° C. $^1$H NMR (400 MHz, d$_6$-DMSO) δ 5.61 (s, 2H), 7.54 (t, J=7.2 Hz, 2H), 7.65 (td, J=7.2 and 1.2 Hz, 2H), 8.11 (d, J=8.8 Hz, 2H), 8.44 (d, J=8.8 Hz, 2H), 8.66 (s, 1H), 9.52 (br s, 2H); $^{13}$C NMR (100 MHz, d$_6$-DMSO) δ 29.1, 124.1, 124.5 (2C), 126.2 (2C), 127.8 (2C), 129.5, 129.9 (2C), 130.6 (2C), 131.6 (2C), 170.5; MS (ESI) m/z 191.1 (100%, [M-CH$_3$N$_2$S]$^+$); HRMS calcd for C$_{16}$H$_{15}$N$_2$S: 267.0950; observed: 267.0951.

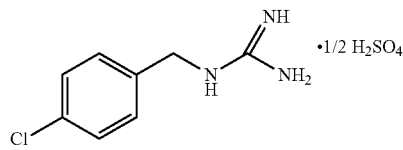

6a—White solid, mp 220-221° C.; $^1$H NMR (250 MHz, d$_4$-MeOH) δ 4.39 (s, 2 H), 7.37 (s, 4H); MS (ESI) m/z 184.0 (100%, [M+H]$^+$); HRMS calcd for C$_8$H$_{11}$ClN$_3$: 184.0636; observed: 184.0638; HPLC analysis (Alltech C18): 90% methanol, 10% acetonitrile, flow rate 0.5 mL/min: $t_R$ 3.85 min. 90% acetonitrile, 10% water, flow rate 0.75 mL/min: $t_R$ 2.03 min.

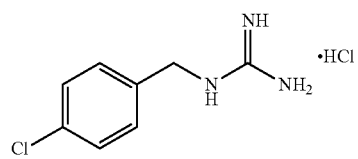 [SMILES: N=C(N)NCc1ccc(Cl)cc1 ; Cl]

6b—Off-white solid, mp 170-171° C.; $^1$H NMR (400 MHz, d$_6$-DMSO) δ 4.42 (d, J=10.0 Hz, 2 H), 7.19-7.85 (br s, 2 H), 7.35 (s, 4 H), 7.47 (d, J=6.0 Hz, 1 H), 7.93 (t, J=10.0 Hz, 1 H); MS (ESI) m/z 184.0 (100%, [M+H]$^+$); HRMS calcd for $C_8H_{11}ClN_3$: 184.0636; observed: 184.0638; HPLC analysis (Alltech C18): 90% methanol, 10% acetonitrile, flow rate 0.5 mL/min: $t_R$ 3.13 min. 90% acetonitrile, 10% water, flow rate 0.75 mL/min: $t_R$ 2.06 min.

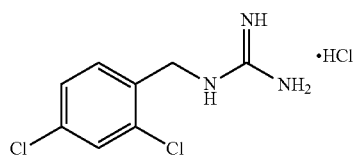 [SMILES: N=C(N)NCc1ccc(Cl)cc1Cl ; Cl]

6c—Pale yellow solid, mp 202-203° C.; $^1$H NMR (400 MHz, d$_6$-DMSO) δ 4.43 (d, J=10.0 Hz, 2 H), 7.34 (d, J=8.4 Hz, 1 H), 7.47 (dd, J=8.4 and 2.0 Hz, 1 H), 7.64 (d, J=2.0 Hz, 1 H), 7.91 (t, J=6.0 Hz, 1 H); MS (ESI) m/z 218.0 (100%, [M+H]$^+$); HRMS calcd for $C_8H_{10}Cl_2N_3$: 218.0246; observed: 218.0248; HPLC analysis (Alltech C18): 90% methanol, 10% acetonitrile, flow rate 0.5 mL/min: $t_R$ 3.01 min. 90% acetonitrile, 10% water, flow rate 0.75 mL/min: $t_R$ 2.03 min.

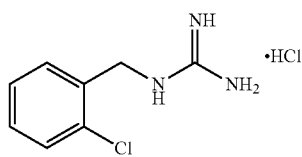 [SMILES: N=C(N)NCc1ccccc1Cl ; Cl]

6d—Off-white solid, mp 188-189° C.; $^1$H NMR (400 MHz, CDCl$_3$) δ 4.35 (s, 2 H), 7.13-7.35 (m, 4 H), 7.40 (s, 1 H), 7.61 (br s, 2 H), 9.08 (br s, 2 H); MS (ESI) m/z 184.0 (100%, [M+H]$^+$), 126.0 (70%, [M-CH$_3$N$_3$]$^+$); HRMS calcd for $C_8H_{11}ClN_3$: 184.0636; observed: 184.0634.

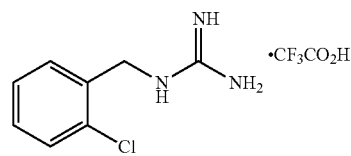 [SMILES: N=C(N)NCc1ccccc1Cl ; "·CF3CO2H"]

6e—Colorless solid, mp 124-125° C.; $^1$H NMR (400 MHz, d$_4$-MeOH) δ 4.49 (s, 2 H), 7.34-7.41 (m, 3 H), 7.45-7.48 (m, 1 H); MS (ESI) m/z 184.0 (100%, [M+H]$^+$); HRMS calcd for $C_8H_{11}ClN_3$: 184.0636; observed: 184.0640; HPLC analysis (Alltech C18): 90% methanol, 10% acetonitrile, flow rate 0.5 mL/min: $t_R$ 3.10 min. 90% acetonitrile, 10% water, flow rate 0.75 mL/min: $t_R$ 1.88 min.

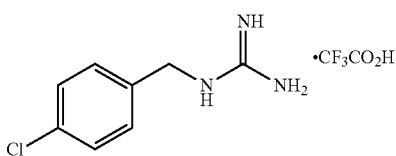 [SMILES: N=C(N)NCc1ccc(Cl)cc1 ; "·CF3CO2H"]

6f—Pale yellow solid, mp 76-77° C.; $^1$H NMR (400 MHz, d$_4$-MeOH) δ 4.38 (s, 2 H), 7.31 (d, J=8.4 Hz, 2 H), 7.39 (d, J=8.4 Hz, 2 H); MS (ESI) m/z 184.0 (100%, [M+H]$^+$); HRMS calcd for $C_8H_{11}ClN_3$: 184.0636; observed: 184.0634; HPLC analysis (Alltech C18): 90% methanol, 10% acetonitrile, flow rate 0.5 mL/min: $t_R$ 3.11 min. 90% acetonitrile, 10% water, flow rate 0.75 mL/min: $t_R$ 2.06 min.

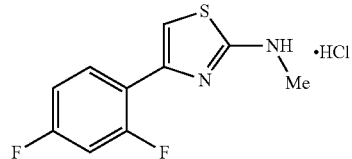 [SMILES: CNc1nc(-c2ccc(F)cc2F)cs1 ; Cl]

7a—Off-white solid, mp 75-76° C.; $^1$H NMR (400 MHz, d$_6$-DMSO) δ 2.92 (s, 3 H), 7.02 (s, 1 H), 7.17 (t, J=9.2 Hz, 1 H), 7.35 (t, J=9.8 Hz, 1 H), 7.82-7.86 (m, 1 H); MS (ESI) m/z 227.0 (100%, [M+H]$^+$); HRMS calcd for $C_{10}H_9F_2N_2S$: 227.0449; observed: 227.0448; HPLC analysis (Alltech C18): 90% methanol, 10% acetonitrile, flow rate 0.5 mL/min: $t_R$ 4.23 min. 90% acetonitrile, 10% water, flow rate 0.75 mL/min: $t_R$ 2.90 min.

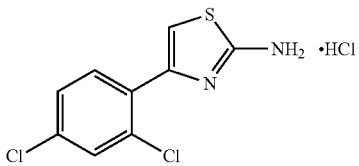 [SMILES: Nc1nc(-c2ccc(Cl)cc2Cl)cs1 ; Cl]

7b—White solid, mp 185-186° C.; $^1$H NMR (400 MHz, d$_4$-MeOH) δ 7.03 (s, 1 H), 7.50 (dd, J=8.2 and 2.0 Hz, 1 H), 7.57 (d, J=8.2 Hz, 1 H), 7.68 (d, J=2.0 Hz, 1 H); MS (ESI) m/z 244.9 (100%, [M+H]$^+$); HRMS calcd for $C_9H_7Cl_2N_2S$: 244.9701; observed: 244.9701; HPLC analysis (Alltech C18): 90% methanol, 10% acetonitrile, flow rate 0.5 mL/min: $t_R$ 4.65 min. 90% acetonitrile, 10% water, flow rate 0.75 mL/min: $t_R$ 3.05 min.

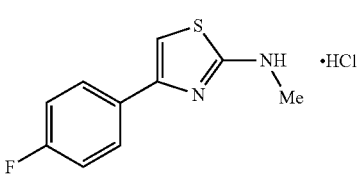 [SMILES: CNc1nc(-c2ccc(F)cc2)cs1 ; Cl]

7c—Off-white solid, mp 112-113° C.; $^1$H NMR (400 MHz, d$_6$-DMSO) δ 2.94 (s, 3 H), 7.10 (s, 1 H), 7.25 (t, J=8.8 Hz, 2 H), 7.82 (dd, J=8.8 and 5.6 Hz, 2 H); MS (ESI) m/z 209.0 (100%, [M+H]$^+$); HRMS calcd for $C_{10}H_{10}FN_2S$: 209.0543; observed: 209.0572; HPLC analysis (Alltech C18): 90% methanol, 10% acetonitrile, flow rate 0.5 mL/min: $t_R$ 4.48 min. 90% acetonitrile, 10% water, flow rate 0.75 mL/min: $t_R$ 4.11 min.

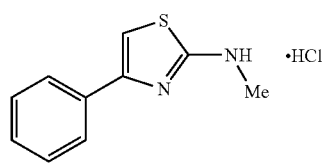 [SMILES: CNc1nc(-c2ccccc2)cs1 ; Cl]

7d—Yellow plates, mp 100-101° C.; $^1$H NMR (400 MHz, d$_6$-DMSO) δ 2.97 (s, 3 H), 7.16 (s, 1 H), 7.36 (t, J=7.2 Hz, 1 H), 7.43 (t, J=7.2 Hz, 2 H), 7.74 (d, J=7.2 Hz, 2 H); MS (ESI) m/z 191.0 (100%, [M+H]$^+$); HRMS calcd for C$_{10}$H$_{11}$N$_2$S: 191.0637; observed: 191.0640; HPLC analysis (Alltech C18): 90% methanol, 10% acetonitrile, flow rate 0.5 mL/min: t$_R$ 4.58 min. 90% acetonitrile, 10% water, flow rate 0.75 mL/min: t$_R$ 3.00 min.

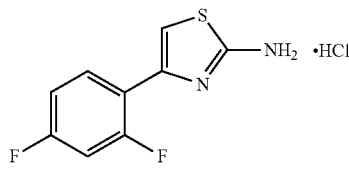 [SMILES: Nc1nc(-c2ccc(F)cc2F)cs1 ; Cl]

7e—White solid, mp 110-111° C.; $^1$H NMR (400 MHz, d$_6$-DMSO) δ 7.08 (d, J=2.0 Hz, 1 H), 7.23 (td, J=9.2 and 2.4 Hz, 1 H), 7.40-7.46 (m, 1 H), 7.84-7.90 (m, 1 H); MS (ESI) m/z 213.0 (100%, [M+H]$^+$); HRMS calcd for C$_9$H$_7$F$_2$N$_2$S: 213.0293; observed: 213.0299; HPLC analysis (Alltech C18): 90% methanol, 10% acetonitrile, flow rate 0.5 mL/min: t$_R$ 3.93 min. 90% acetonitrile, 10% water, flow rate 0.75 mL/min: t$_R$ 2.68 min.

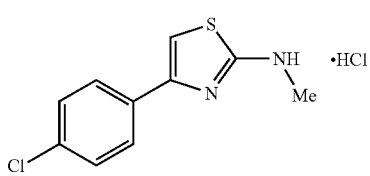 [SMILES: CNc1nc(-c2ccc(Cl)cc2)cs1 ; Cl]

7f—White needles, mp 209-210° C.; $^1$H NMR (400 MHz, d$_6$-DMSO) δ 2.97 (s, 3 H), 7.21 (s, 1 H), 7.48 (dt, J=8.4 and 2.0 Hz, 2 H), 7.82 (dt, J=8.4 and 2.0 Hz, 2 H); MS (ESI) m/z 225.0 (100%, [M+H]$^+$); HRMS calcd for C$_{10}$H$_{10}$ClN$_2$S: 225.0247; observed: 225.0248; HPLC analysis (Alltech C18): 90% methanol, 10% acetonitrile, flow rate 0.5 mL/min: t$_R$ 5.15 min. 90% acetonitrile, 10% water, flow rate 0.75 mL/min: t$_R$ 3.31 min.

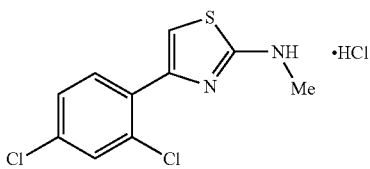 [SMILES: CNc1nc(-c2ccc(Cl)cc2Cl)cs1 ; Cl]

7g—Pale yellow solid, mp 134-135° C.; $^1$H NMR (400 MHz, d$_4$-MeOH) δ 3.12 (s, 3 H), 7.04 (s, 1 H), 7.50 (dd, J=8.8 and 2.0 Hz, 1 H), 7.58 (d, J=8.8 Hz, 1 H), 7.69 (d, J=2.0 Hz, 1 H); MS (ESI) m/z 258.9 (100%, [M+H]$^+$); HRMS calcd for C$_{10}$H$_9$Cl$_2$N$_2$S: 258.9858; observed: 258.9858; HPLC analysis (Alltech C18): 90% methanol, 10% acetonitrile, flow rate 0.5 mL/min: t$_R$ 4.90 min. 90% acetonitrile, 10% water, flow rate 0.75 mL/min: t$_R$ 3.26 min.

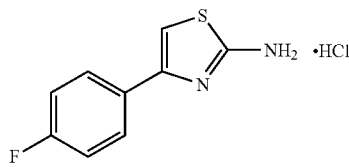 [SMILES: Nc1nc(-c2ccc(F)cc2)cs1 ; Cl]

7h—White solid, mp 219-220° C.; $^1$H NMR (400 MHz, d$_6$-DMSO) δ 7.15 (s, 1 H), 7.29 (t, J=8.8 Hz, 2 H), 7.40-7.46 (dd, J=8.4 and 5.2 Hz, 2 H); MS (ESI) m/z 195.0 (100%, [M+H]$^+$); HRMS calcd for C$_9$H$_8$FN$_2$S: 195.0386; observed: 195.0390; HPLC analysis (Alltech C18): 90% methanol, 10% acetonitrile, flow rate 0.5 mL/min: t$_R$ 3.45 min. 90% acetonitrile, 10% water, flow rate 0.75 mL/min: t$_R$ 2.36 min.

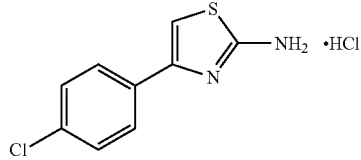 [SMILES: Nc1nc(-c2ccc(Cl)cc2)cs1 ; Cl]

7i—White solid, mp 211-212° C.; $^1$H NMR (400 MHz, d$_6$-DMSO) δ 7.25 (s, 1 H), 7.52 (d, J=8.4 Hz, 2 H), 7.78 (d, J=8.4, 2 H); MS (ESI) m/z 211.0 (100%, [M+H]$^+$); HRMS calcd for C$_9$H$_8$ClN$_2$S: 211.0091; observed: 211.0092; HPLC analysis (Alltech C18): 90% methanol, 10% acetonitrile, flow rate 0.5 mL/min: t$_R$ 4.23 min. 90% acetonitrile, 10% water, flow rate 0.75 mL/min: t$_R$ 2.78 min.

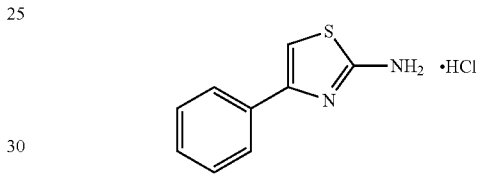

7j—White solid, mp 200-201° C.; $^1$H NMR (400 MHz, d$_6$-DMSO) δ 3.52 (br s, 2 H), 7.15 (s, 1 H), 7.35-7.39 (m, 1 H), 7.40-7.46 (m, 2 H), 7.74 (dd, J=6.8 Hz and 1.2 Hz, 1H); MS (ESI) m/z 177.0 (100%, [M+H]$^+$); HRMS calcd for C$_9$H$_9$N$_2$S: 177.0481; observed: 177.0479; HPLC analysis (Alltech C18): 90% methanol, 10% acetonitrile, flow rate 0.5 mL/min: t$_R$ 3.90 min. 90% acetonitrile, 10% water, flow rate 0.75 mL/min: t$_R$ 2.56 min.

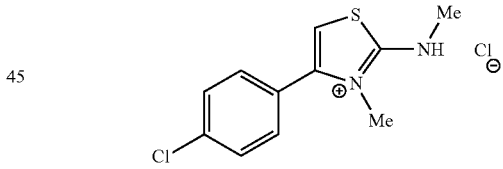

8a—White solid, mp 212-213° C.; $^1$H NMR (400 MHz, d$_6$-DMSO) δ 3.02 (s, 3 H), 3.44 (s, 3 H), 7.12 (s, 1 H), 7.54 (d, J=8.8 Hz, 2 H), 7.61 (J=8.8 Hz, 2 H), 10.40 (s, 1 H); MS (ESI) m/z 239.0 (100%, [M]$^+$); HRMS calcd for C$_{11}$H$_{12}$ClN$_2$S: 239.0404; observed: 239.0404; HPLC analysis (Alltech C18): 90% methanol, 10% acetonitrile, flow rate 0.5 mL/min: t$_R$ 3.01 min. 90% acetonitrile, 10% water, flow rate 0.75 mL/min: t$_R$ 2.01 min.

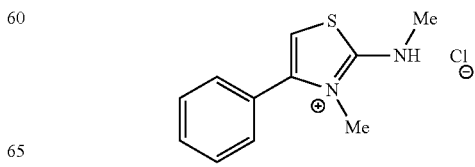

8b—Off-white solid, mp 233-234° C.; $^1$H NMR (400 MHz, d$_6$-DMSO) δ 3.02 (s, 3 H), 3.44 (s, 3 H), 7.08 (s, 1 H), 7.49-7.56 (m, 5 H), 10.40 (s, 1 H); MS (ESI) m/z 205.0 (100%, [M]$^+$); HRMS calcd for C$_{11}$H$_{13}$N$_2$S: 205.0794; observed: 205.0797; HPLC analysis (Alltech C18): 90% methanol, 10% acetonitrile, flow rate 0.5 mL/min: t$_R$ 3.01 min. 90% acetonitrile, 10% water, flow rate 0.75 mL/min: t$_R$ 1.96 min.

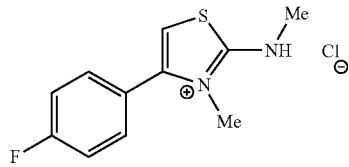 [SMILES: CNc1scc(-c2ccc(F)cc2)[n+]1C ; [Cl-]]

8c—White solid, mp 203-204° C.; $^1$H NMR (400 MHz, d$_6$-DMSO) δ 3.02 (s, 3 H), 3.43 (s, 3 H), 7.09 (s, 1 H), 7.38 (t, J=8.8 Hz, 2 H), 7.57 (m, 2 H), 10.42 (s, 1 H); MS (ESI) m/z 223.0 (100%, [M]$^+$); HRMS calcd for C$_{11}$H$_{12}$FN$_2$S: 223.0700; observed: 223.0707; HPLC analysis (Alltech C18): 90% methanol, 10% acetonitrile, flow rate 0.5 mL/min: t$_R$ 3.00 min. 90% acetonitrile, 10% water, flow rate 0.75 mL/min: t$_R$ 2.01 min.

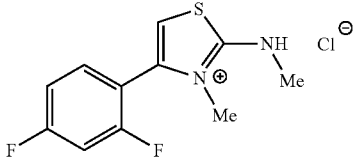 [SMILES: CNc1scc(-c2ccc(F)cc2F)[n+]1C ; [Cl-]]

8d—White solid, mp 253-254° C.; $^1$H NMR (400 MHz, d$_6$-DMSO) δ 3.02 (s, 3 H), 3.36 (s, 3 H), 7.22 (s, 1 H), 7.29 (td, J=8.4 and 2.0 Hz, 1 H), 7.52 (td, J=10.0 and 2.0 Hz, 1 H), 7.29 (qd, J=6.8 and 2.0 Hz, 1 H), 10.40 (s, 1 H); MS (ESI) m/z 241.0 (100%, [M]$^+$); HRMS calcd for C$_{11}$H$_{11}$ClF$_2$N$_2$S: 241.0605; observed: 241.0618; HPLC analysis (Alltech C18): 90% methanol, 10% acetonitrile, flow rate 0.5 mL/min: t$_R$ 3.00 min. 90% acetonitrile, 10% water, flow rate 0.75 mL/min: t$_R$ 1.98 min.

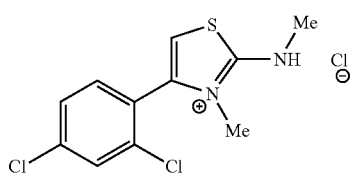 [SMILES: CNc1scc(-c2ccc(Cl)cc2Cl)[n+]1C ; [Cl-]]

8e—Off-white solid, mp 271-272° C.; $^1$H NMR (400 MHz, CDCl$_3$) δ 3.19 (s, 3 H), 3.70 (s, 3 H), 6.56 (s, 1 H), 7.30 (d, J=8.0 Hz, 2 H), 7.43 (dd, J=8.0 and 2.0 Hz, 2 H), 7.59 (d, J=2.0 Hz, 2 H); MS (ESI) m/z 273.0 (100%, [M]$^+$); HRMS calcd for C$_{11}$H$_{10}$Cl$_2$N$_2$S: 273.0014; observed: 273.0016; HPLC analysis (Alltech C18): 90% methanol, 10% acetonitrile, flow rate 0.5 mL/min: t$_R$ 3.01 min. 90% acetonitrile, 10% water, flow rate 0.75 mL/min: t$_R$ 2.03 min.

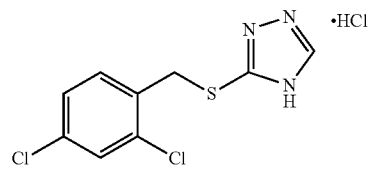 [SMILES: Clc1ccc(CSc2nnc[nH]2)c(Cl)c1 ; Cl]

9a—White solid, mp 169-170° C. $^1$H NMR (400 MHz, d$_6$-DMSO) δ 4.39 (s, 2H), 7.34 (d, J=8.0 Hz, 1H), 7.49 (d, J=8.0 Hz, 2H), 7.61 (s, 1H), 8.45 (s, 1H); $^{13}$C NMR (100 MHz, d$_6$-DMSO) 33.6, 128.0, 129.6, 132.9, 133.5, 134.8, 135.2, 146.8, 156.7; MS (ESI) m/z 259.9 (100%, [M+H]$^+$); HRMS calcd for C$_9$H$_8$Cl$_2$N$_3$S: 259.9810; observed: 259.9812; HPLC analysis (Alltech C18): 90% methanol, 10% acetonitrile, flow rate 0.5 mL/min: t$_R$ 4.56 min. 90% acetonitrile, 10% water, flow rate 0.75 mL/min: t$_R$ 2.81 min.

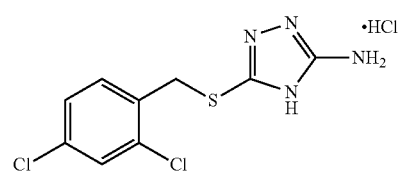 [SMILES: Nc1nnc(SCc2ccc(Cl)cc2Cl)[nH]1 ; Cl]

9b—White solid, mp 110-111° C.; $^1$H NMR (400 MHz, d$_6$-DMSO) δ 4.31 (s, 2 H), 7.37 (d, J=8.0 Hz, 1 H), 7.48 (d, J=8.0 Hz, 1 H), 7.63 (s, 1 H); MS (ESI) m/z 274.9 (100%, [M+H]$^+$); HRMS calcd for C$_9$H$_9$Cl$_2$N$_4$S: 274.9919; observed: 274.9922; HPLC analysis (Alltech C18): 90% methanol, 10% acetonitrile, flow rate 0.5 mL/min: t$_R$ 3.78 min. 90% acetonitrile, 10% water, flow rate 0.75 mL/min: t$_R$ 2.41 min.

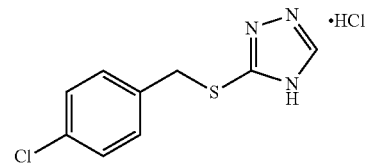 [SMILES: Clc1ccc(CSc2nnc[nH]2)cc1 ; Cl]

9c—White solid, mp 161-162° C.; $^1$H NMR (400 MHz, d$_6$-DMSO) δ 4.31 (s, 2 H), 3.32 (d, J=8.8 Hz, 2 H), 3.36 (d, J=8.8 Hz, 2 H), 8.44 (s, 1 H); MS (ESI) m/z 226.0 (100%, [M+H]$^+$); HRMS calcd for C$_9$H$_9$ClN$_3$S: 226.0200; observed: 226.0201; HPLC analysis (Alltech C18): 90% methanol, 10% acetonitrile, flow rate 0.5 mL/min: t$_R$ 3.96 min. 90% acetonitrile, 10% water, flow rate 0.75 mL/min: t$_R$ 3.43 min.

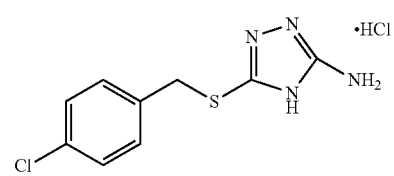 [SMILES: Nc1nnc(SCc2ccc(Cl)cc2)[nH]1 ; Cl]

9d—Pale yellow solid, mp 122-123° C.; $^1$H NMR (400 MHz, d$_6$-DMSO) δ 4.32 (s, 2 H), 7.36 (s, 4 H); MS (ESI) m/z 241.0 (100%, [M+H]$^+$); HRMS calcd for C$_9$H$_{10}$ClN$_4$S: 241.0309; observed: 241.0313; HPLC analysis (Alltech C18): 90% methanol, 10% acetonitrile, flow rate 0.5 mL/min: $t_R$ 3.56 min. 90% acetonitrile, 10% water, flow rate 0.75 mL/min: $t_R$ 2.35 min.

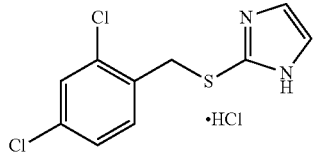 [SMILES: Clc1ccc(CSc2ncc[nH]2)c(Cl)c1 ; Cl]

9e—White solid, mp 183-184° C.; $^1$H NMR (250 MHz, CDCl$_3$) δ 4.35 (s, 2 H), 7.09-7.11 (m, 2 H), 7.13 (s, 2 H), 7.38 (m, 1 H); MS (ESI) m/z 258.9 (100%, [M+H]$^+$); HRMS calcd for $C_{10}H_9Cl_2N_2S$: 258.9858; observed: 258.9854; HPLC analysis (Alltech C18): 90% methanol, 10% acetonitrile, flow rate 0.5 mL/min: $t_R$ 4.00 min. 90% acetonitrile, 10% water, flow rate 0.75 mL/min: $t_R$ 2.66 min.

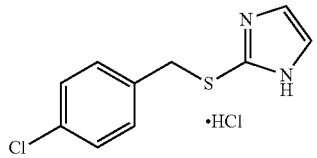 [SMILES: Clc1ccc(CSc2ncc[nH]2)cc1 ; Cl]

9f—White solid, mp 137-138° C.; $^1$H NMR (250 MHz, CDCl$_3$) δ 4.17 (s, 2 H), 7.09 (s, 2 H), 7.11 (d, J=8.5 Hz, 2 H), 7.24 (d, J=8.5 Hz, 2 H); MS (ESI) m/z 225.0 (100%, [M+H]$^+$); HRMS calcd for $C_{10}H_{10}ClN_2S$: 225.0247; observed: 225.0251; HPLC analysis (Alltech C18): 90% methanol, 10% acetonitrile, flow rate 0.5 mL/min: $t_R$ 3.81 min. 90% acetonitrile, 10% water, flow rate 0.75 mL/min: $t_R$ 2.53 min.

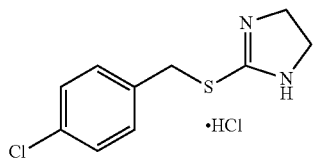 [SMILES: Clc1ccc(CSC2=NCCN2)cc1 ; Cl]

9g—White solid, mp 167-168° C.; $^1$H NMR (250 MHz, d$_6$-DMSO) δ 3.84 (s, 4 H), 4.66 (s, 2 H), 7.45 (d, J=8.6 Hz, 2 H), 7.54 (d, J=8.6 Hz, 2 H), 10.68 (s, 2 H); MS (ESI) m/z 227.0 (100%, [M+H]$^+$); HRMS calcd for $C_{10}H_{12}ClN_2S$: 227.0404; observed: 227.0410; HPLC analysis (Alltech C18): 90% methanol, 10% acetonitrile, flow rate 0.5 mL/min: $t_R$ 2.78 min. 90% acetonitrile, 10% water, flow rate 0.75 mL/min: $t_R$ 1.70 min.

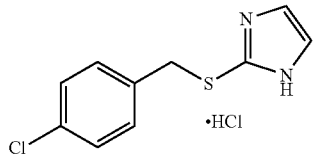 [SMILES: Clc1ccc(CSc2ncc[nH]2)cc1 ; Cl]

9h—Pale pink solid, mp 121-122° C.; $^1$H NMR (250 MHz, CDCl$_3$) δ 4.84 (s, 1 H), 7.34 (dt, J=8.5 and 2.0 Hz, 2 H), 7.48 (dt, J=8.5 and 2.0 Hz, 2 H), 7.49 (td, J=7.5 and 1.2 Hz, 1H), 7.60 (td, J=7.5 and 1.2 Hz, 1H), 7.82 (dd, J=7.5 and 1.2 Hz, 1H), 8.27 (dd, J=7.5 and 1.2 Hz, 1H); MS (ESI) m/z 292.0 (100%, [M+NH$_4$]$^+$); HPLC analysis (Alltech C18): 90% methanol, 10% acetonitrile, flow rate 0.5 mL/min: $t_R$ 7.35 min. 90% acetonitrile, 10% water, flow rate 0.75 mL/min: $t_R$ 6.70 min.

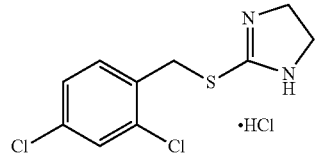 [SMILES: Clc1ccc(CSC2=NCCN2)c(Cl)c1 ; Cl]

9i—White solid, mp 223-224° C.; $^1$H NMR (250 MHz, d$_6$-DMSO) δ 3.87 (s, 4 H), 4.76 (s, 2 H), 7.49 (dd, J=8.3 and 2.1 Hz, 1 H), 7.73 (d, J=2.1 Hz, 1 H), 7.80 (d, J=8.3 Hz, 1 H), 10.83 (s, 2 H); MS (ESI) m/z 262.0 (100%, [M+H]$^+$); HRMS calcd for $C_{10}H_{11}Cl_2N_2S$: 261.0014; observed: 261.0014; HPLC analysis (Alltech C18): 90% methanol, 10% acetonitrile, flow rate 0.5 mL/min: $t_R$ 3.01 min. 90% acetonitrile, 10% water, flow rate 0.75 mL/min: $t_R$ 1.98 min.

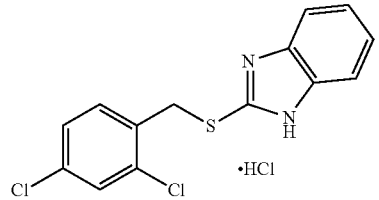 [SMILES: Clc1ccc(CSc2nc3ccccc3[nH]2)c(Cl)c1 ; Cl]

9j—Off-white solid, mp 124-125° C.; $^1$H NMR (400 MHz, CDCl$_3$) δ 4.91 (s, 2 H), 7.22 (dd, J=8.2 and 2.1 Hz, 1 H), 7.44 (t, J=8.0 Hz, 2 H), 7.56 (t, J=8.3 Hz, 1 H), 7.68 (d, J=8.3 Hz, 1 H), 7.80 (d, J=8.0 Hz, 1 H), 8.19 (d, J=8.1 Hz, 1 H); MS (ESI) m/z 325.9 (100%, [M+NH$_4$]$^+$); HPLC analysis (Alltech C18): 90% methanol, 10% acetonitrile, flow rate 0.5 mL/min: $t_R$ 8.26 min. 90% acetonitrile, 10% water, flow rate 0.75 mL/min: $t_R$ 7.86 min.

The following additional compounds were made by the preceding methods:

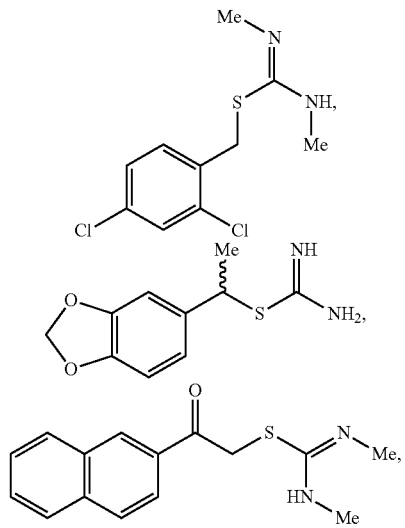

-continued

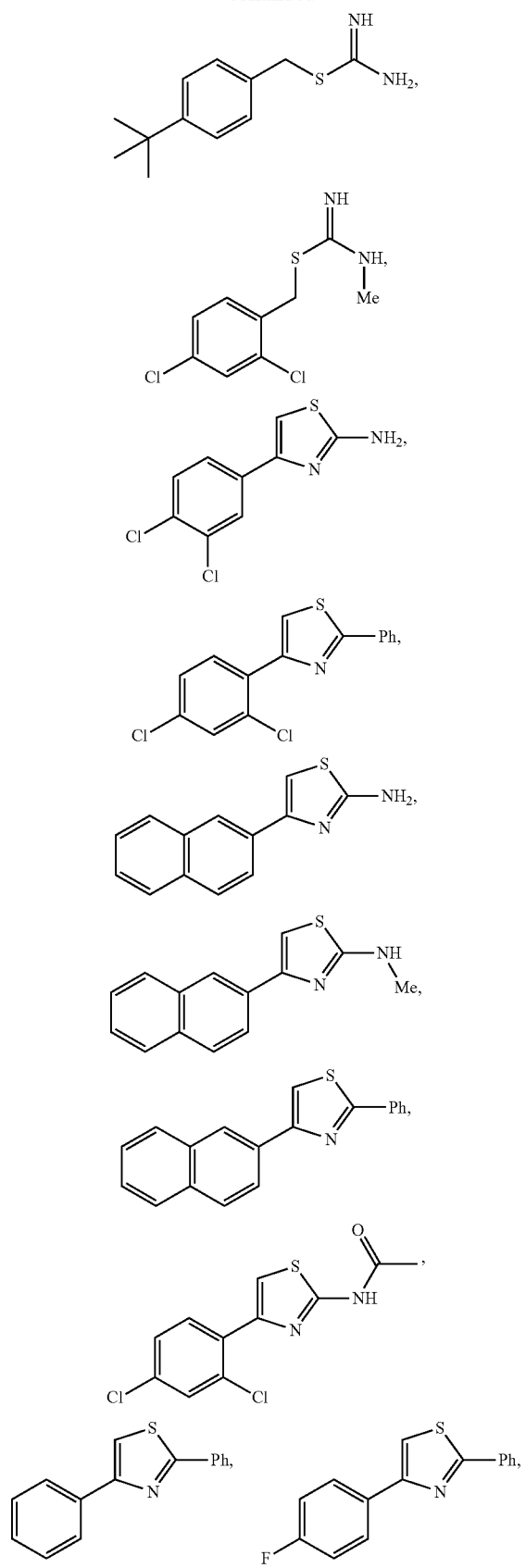

-continued

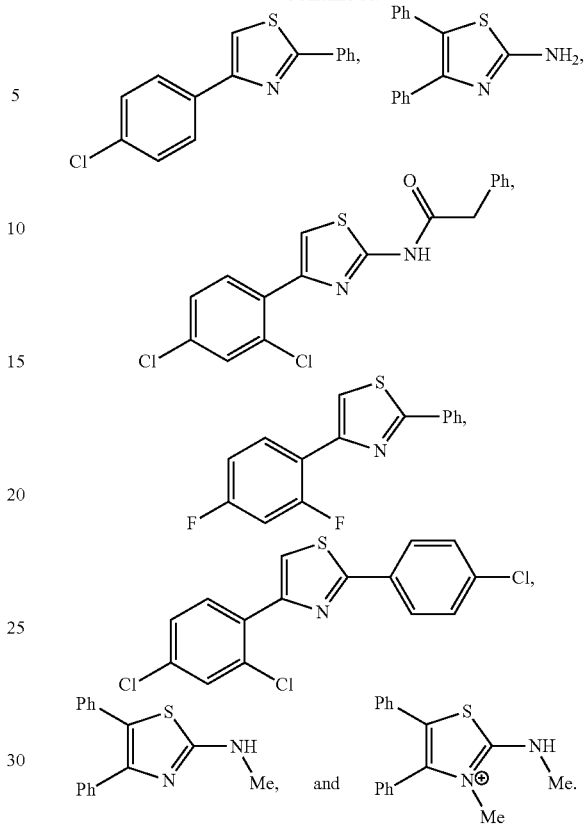

EXAMPLE 4

The Disclosed Compounds Have Rb:Raf-1 Binding Inhibition Activity

Compounds that can directly inhibit GST Rb binding to GST-Raf-1 were identified from the NCI diversity library of 1981 compounds as described under Methods, resulting in two compounds, (1) and (2), which inhibited Rb:Raf-1 binding 100% and 95% respectively. Both were benzylisothiourea derivatives of similar structure (FIG. 1a). Next, the library of compounds, comprising the benzylisothiouronium derivatives 3a-t, 4a-e and 5a-f; of the benzylguanidinium derivatives 6a-f; of the aminothiazolium derivatives 7a-j, and 8a-e; and of the mercapto analogues 9a-j was screened for Rb:Raf-1 binding inhibitory properties using the GST-Rb/GST-Raf-1 ELISA assay. The results are reported as % inhibition of Rb:Raf-1 binding at a concentration of 20 micromolar (μM, Tables 1-7). A dose response was performed for compounds able to inhibit the interaction by 80% or greater at 20 μM. The results, shown in Table 8, are reported as the concentration required to disrupt the interaction by 50% relative to an untreated control ($IC_{50}$ value).

Generally, the activities related to the aromatic substitution pattern, where the halogenated derivatives exhibited highest potencies. For the benzylisothiouronium derivatives 3a-t, active compounds tended to possess a monosustituted or disubstituted benzene ring, bearing at least one halide in either one of the positions ortho, meta, or para to the carbon bound to the isothiouronium group. The sensitivity to halide substitution is shown by comparison of 3b (100% inhibition), 3g (88% inhibition) and 3r (inactive). The presence of either 2- or 4-chloro substituent strongly affects the activity. The activity of 3a suggested that the activity of 1 derives from the presence of the benzylisothiouronium ion and not the nitrophenolate ion.

Most of the chlorine-containing derivatives display $IC_{50}$ values in the submicromolar range (3b 0.575, 3c 0.081, 3e 0.230 and 3f 0.312 µM). The 2,4-dichloro aromatic substitution pattern, which is common to 3a and to the hit (1), particularly tended to enhance the inhibitory activity ($IC_{50}$ values: 3a, 77 nM; 1, 100 nM). By contrast, derivative 3r, having 2 hydrogens in place of the 2 chlorines of 3a or 1 tended to be inactive. Thus, the chlorines tend to increase the compound's ability to disrupt the binding of Rb to Raf-1 (Tables 1 and 8). Two chlorines on the phenyl ring tended to be better one as 3a was 3 to 6-fold more potent than 3b (2-chlorobenzylisothiourea, $IC_{50}$=575 nM), 3e (3-chlorobenzylisothiourea, $IC_{50}$=230 nM) and 3g (4-chlorobenzylisothiourea, $IC_{50}$=274 nM). Placement of the chlorines tends to affect activity strongly because the 2,3-dichloro derivative 3d was more than 2-fold less active compared to 3a ($IC_{50}$=164 nM), 3,4-dichloro derivative 3h was 50 times less active compared 3a ($IC_{50}$=3900 nM) and the 2,6-dichloro derivative 3s and 2,4,6-trichloro derivative 3t were inactive compared to 3a. Furthermore, replacing the 2 chloro groups in 3a by 2 trifluoromethyl groups as in the 2,4-trifluoromethyl derivative 3j tended to reduce the activity (Table 1 and 8). A decrease in potency was observed when the compounds were substituted in the alpha position with alkyl groups (Table 2). For example the addition of the methyl or ethyl group to 3a results in a four and seven fold weaker inhibition respectively ($IC_{50}$ 3a 77 nM; 4a $IC_{50}$ 322 nM; $IC_{50}$ 4c 567 nM).

The highest inhibitory activity among the arymethylisothiouronium derivatives 5a-f was displayed by the 1-bromonaphthyl derivative 5a (80 nM). Substituting a bromo by a chloro and linking to the isothiourea at the 4 position as in 3c tended to reduce activity by 24-fold (Table 3 and 8) as shown by the analogue 5c ($IC_{50}$=1900 nM).

The isothiourea group tended to increase activity as replacing the isothiourea in 3a by guanidinium as in 6c tended to dramatically reduce the activity (Table 4 and 8). The activities of the benzylguanidinium derivatives 6a-f, were in some cases dependant on the counterion. Compound 6a, a benzylguanidinium hydrosulfate, tended to display the highest potency ($IC_{50}$ 539 nM; 100% inhibition at 20 µM), whereas the benzylguanidinium hydrochlorides 6b-d were less active (59-61% inhibition at 20 µM), and the benzylguanidinium trifluoroacetates 6e and 6f tended to be the least active of the series (respectively, 25 and 16% inhibition at 20 µM).

The aminothiazolium derivatives 7a-j generally displayed modest activity, as did most of the analogues 8a-e. The most active compounds was the difluoro derivative 7a, which inhibited the Rb:Raf-1 binding 53% at 20 M. Finally, amongst the thioheterocyclic analogues 9a-j the highest potencies were displayed by the triazoles 9a (97 nM) and 9b (131 nM), which both have the 2,4-dichloro aromatic substitution pattern. These derivatives differ by one amino group, which tended to have less effect on activity.

TABLE 1

Structures, yields of benzylisothiouronium salts 3a-t, and inhibition of Rb:Raf-1 binding.

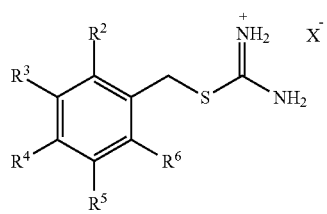

3a-t

| Compound | $R^2$ | $R^3$ | $R^4$ | $R^5$ | $R^6$ | X | Yield (%) | % Inhibition at 20 µM |
|---|---|---|---|---|---|---|---|---|
| 3a | Cl | H | Cl | H | H | Cl | 98 | 100 |
| 3b | Cl | H | H | H | H | Cl | 76 | 100 |
| 3c | H | F | Cl | H | H | Cl | 96 | 100 |
| 3d | Cl | Cl | H | H | H | Cl | 99 | 100 |
| 3e | H | Cl | H | H | H | Cl | 90 | 100 |
| 3f | H | $CF_3$ | Cl | H | H | Cl | 81 | 94 |
| 3g | H | H | Cl | H | H | Cl | 87 | 88 |
| 3h | H | Cl | Cl | H | H | Cl | 83 | 81 |
| 3i | Cl | H | H | Cl | H | Cl | 93 | 79 |
| 3j | $CF_3$ | H | $CF_3$ | H | H | Br | 86 | 53 |
| 3k | H | H | tBu | H | H | Cl | 81 | 52 |
| 3l | H | O—$CH_2$—O | H | H | Cl | 95 | 49 |
| 3m | H | H | $NO_2$ | H | H | Cl | 75 | 46 |
| 3n | H | H | $CF_3$ | H | H | Br | 77 | 46 |
| 3o | H | H | OMe | H | H | Cl | 98 | 45 |
| 3p | H | H | Me | H | H | Cl | 65 | 44 |
| 3q | H | OMe | OMe | OMe | H | Cl | 52 | 20 |
| 3r | H | H | H | H | H | Cl | 78 | 0 |
| 3s | Cl | H | H | H | Cl | Cl | 81 | 0 |
| 3t | Cl | H | Cl | H | Cl | Cl | 75 | 0 |

TABLE 2

Structures, yields of substituted benzylisothiouronium salts 4a-e, and inhibition of Rb:Raf-1

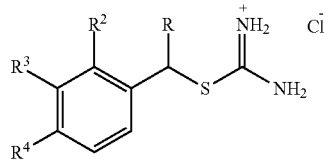

3a-t

| Compounds | R | $R^2$ | $R^3$ | $R^4$ | Yield (%) | % Inhibition at 20 µM |
|---|---|---|---|---|---|---|
| 4a | Me | Cl | H | Cl | 91 | 100 |
| 4b | Me | H | Cl | Cl | 89 | 99 |
| 4c | Et | Cl | H | Cl | 77 | 100 |
| 4d | Ph | H | H | H | 51 | 21 |
| 4e | $CH_2Ph$ | Cl | H | Cl | 18 | 32 |

TABLE 3

Structures, yields of aryl- and heteroaryl-methylisothiouronium salts 5a-f, and inhibition of Rb:Raf-1 binding.

| | Compounds | Yield (%) | % Inhibition at 20 μM |
|---|---|---|---|
| 5a | 1-bromonaphthalen-2-ylmethyl isothiouronium bromide | 82 | 100 |
| 5b | pyridin-4-ylmethyl isothiouronium chloride | 78 | 94 |
| 5c | 4-chloronaphthalen-1-ylmethyl isothiouronium chloride | 10 | 93 |
| 5d | quinolin-2-ylmethyl isothiouronium chloride | 98 | 76 |
| 5e | (9,10-dioxo-9,10-dihydroanthracen-2-yl)methyl isothiouronium bromide | 86 | 56 |
| 5f | anthracen-9-ylmethyl isothiouronium chloride | 97 | 22 |

TABLE 4

Structures, yields of benzylguanidinium salts 6a-f, and inhibition of Rb:Raf-1 binding.

6a-f

| Compound | R² | R⁴ | X | Yield (%) | % Inhibition at 20 μM |
|---|---|---|---|---|---|
| 6a | H | Cl | HSO₄ | 32 | 100 |
| 6b | H | Cl | Cl | 45 | 61 |
| 6c | Cl | Cl | Cl | 87 | 61 |
| 6d | Cl | H | Cl | 95 | 59 |
| 6e | Cl | H | CF₃CO₂ | 58 | 25 |
| 6f | H | Cl | CF₃CO₂ | 61 | 16 |

TABLE 5

Structures, yields of aminothiazolium type salts 7a-j, and inhibition of Rb:Raf-1 binding.

7a-j

| Compound | R | R² | R⁴ | Yield (%) | % Inhibition at 20 μM |
|---|---|---|---|---|---|
| 7a | Me | F | F | 89 | 53 |
| 7b | H | Cl | Cl | 99 | 45 |
| 7c | Me | H | F | 99 | 43 |
| 7d | Me | H | H | 87 | 39 |
| 7e | H | F | F | 96 | 39 |
| 7f | Me | H | Cl | 99 | 34 |
| 7g | Me | Cl | Cl | 95 | 33 |
| 7h | H | H | F | 99 | 32 |
| 7i | H | H | Cl | 89 | 29 |
| 7j | H | H | H | 80 | 22 |

TABLE 6

Structures, yields of aminothiazolium type salts 8a-e, and inhibition of Rb:Raf-1 binding.

8a-e

| Compound | R² | R³ | R⁴ | Yield (%) | % Inhibition at 20 μM |
|---|---|---|---|---|---|
| 8a | H | H | Cl | 84 | 37 |
| 8b | H | H | H | 96 | 22 |
| 8c | H | H | F | 79 | 19 |
| 8d | F | H | F | 89 | 5 |
| 8e | Cl | H | Cl | 75 | — |

TABLE 7

Structures, yields of benzylthioimidazole type analogues 9a-j, and inhibition of Rb:Raf-1 binding.

9a-j

| Compound | R | R² | Yield (%) | % Inhibition at 20 μM |
|---|---|---|---|---|
| 9a | triazole | Cl | 99 | 92 |
| 9b | amino-triazole | Cl | 94 | 91 |
| 9c | triazole | H | 90 | 81 |
| 9d | amino-triazole | H | 93 | 76 |
| 9e | imidazole | Cl | 21 | 68 |
| 9f | imidazole | H | 15 | 67 |
| 9g | imidazoline | H | 84 | 47 |
| 9h | benzimidazole | H | 87 | 46 |
| 9i | imidazoline | Cl | 91 | 45 |

TABLE 7-continued

Structures, yields of benzylthioimidazole type analogues 9a-j, and inhibition of Rb:Raf-1 binding.

9a-j

| Compound | R | R² | Yield (%) | % Inhibition at 20 μM |
|---|---|---|---|---|
| 9j | benzimidazole | Cl | 83 | 40 |

TABLE 8

Inhibition of the Rb:Raf-1 binding (IC$_{50}$) of the most active derivatives 3-9.

| Compound | IC$_{50}$ (nM)$^a$ |
|---|---|
| 3a | 77 ± 4 |
| 5a | 80 ± 6 |
| (1) | 81 ± 4 |
| 3c | 81 ± 10 |
| 9a | 97 ± 4 |
| 9b | 131 ± 22 |
| 3d | 164 ± 9 |
| 3e | 230 ± 25 |
| 3g | 274 ± 24 |
| (2) | 283 ± 46 |
| 3f | 312 ± 53 |
| 4a | 322 ± 87 |
| 4b | 510 ± 116 |
| 6a | 539 ± 13 |
| 4c | 567 ± 91 |
| 3b | 575 ± 115 |
| 5c | 1900 ± 40 |
| 3i | 2110 ± 180 |
| 5b | 2630 ± 330 |
| 3h | 3900 ± 2460 |

$^a$Drug concentration that inhibits the Rb:Raf-1 binding by 50% . . . . Each drug concentration was tested in triplicate, and the standard error of each value was less than 10%.

EXAMPLE 5

The Disclosed Compounds are Selective for Rb:Raf-1 Over Rb-E2F1

Figure 1B:
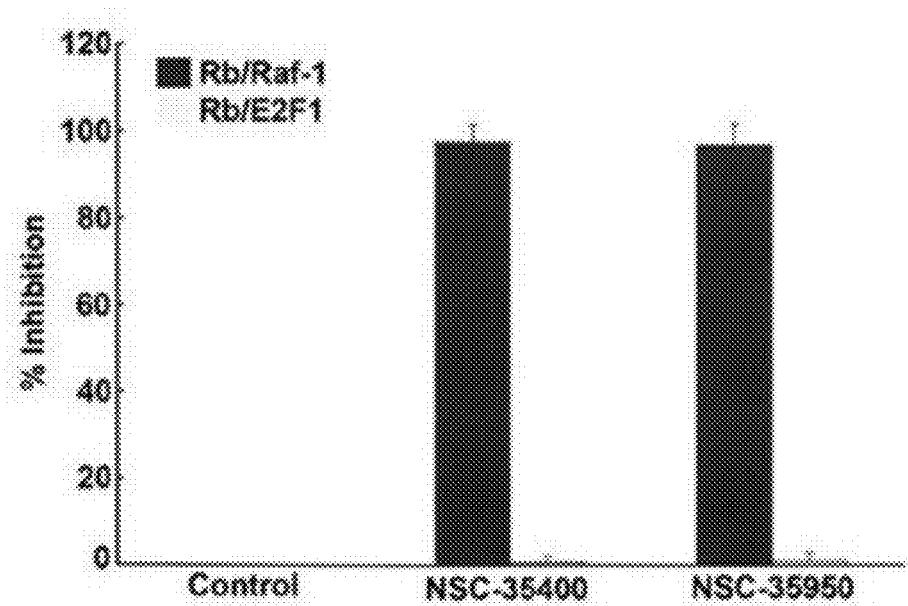
FIG. 1B: Identification of novel Rb:Raf-1 inhibitors. (1) and (2) are selective for inhibiting Rb:Raf-1 and not Rb-E2F1 binding.

The selectivity of (1) and (2) for inhibition of Rb:Raf-1 compared to Rb-E2F1 was tested in a GST ELISA assay. Both hits were at least 200 fold more selective for Rb:Raf-1 over Rb-E2F1 (FIG. 1b).

EXAMPLE 6

The Disclosed Compounds Disrupt Rb:Raf-1 In Vitro

Figure 1C:
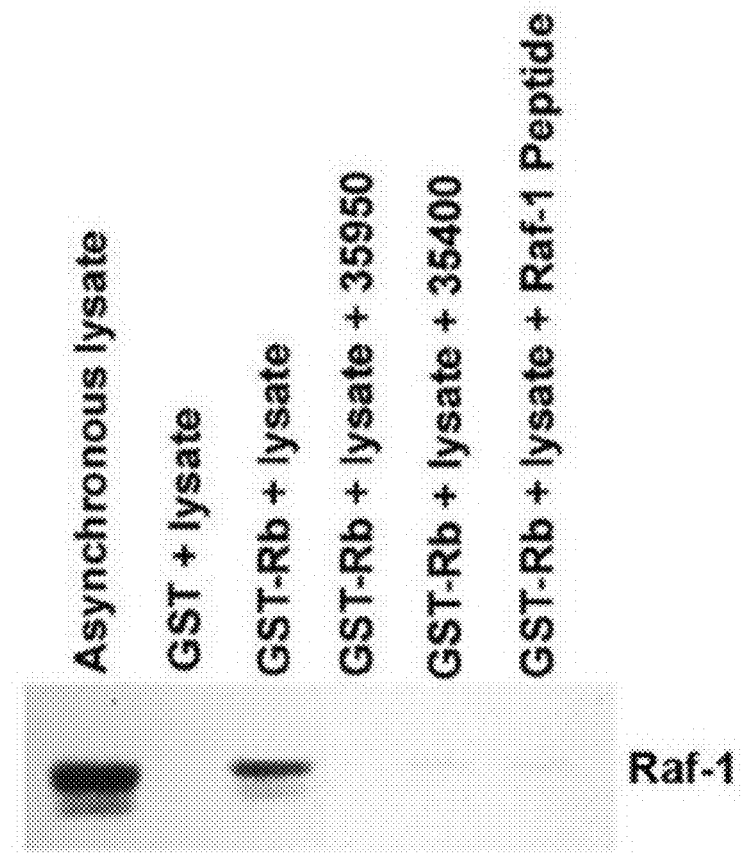
FIG. 1C: Identification of novel Rb:Raf-1 inhibitors. (1), (2), and the Raf-1 peptide inhibited the binding of GST Rb beads to endogenous Raf-1 in U937 cell lysates.

The ability of the small molecules to disrupt Rb:Raf-1 was confirmed by GST pull-down assays, as described in Methods. Asynchronous U937 lysates were incubated with GST-Rb beads in the presence or absence of the selected compounds or an 8 amino acid Raf-1 peptide and the binding of Raf-1 assessed by western blotting. It was found that presence of 20 μM of (1) (IC$_{50}$ of 81±4 nM), (2) (IC$_{50}$ of 283±46 nM) and the Raf-1 peptide inhibited the binding of Raf-1 to GST Rb beads (FIG. 1C).

EXAMPLE 7

The Disclosed Compounds Effectively Disrupt Rb:Raf-1 in Intact Cells

Figure 1D:
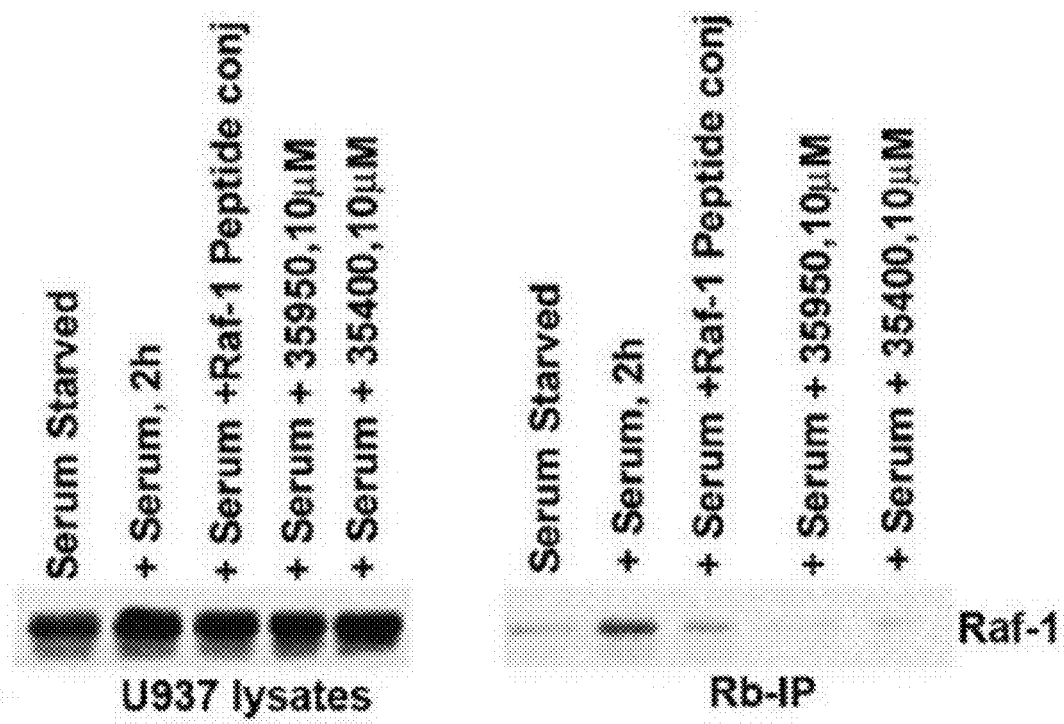
FIG. 1D: Identification of novel Rb:Raf-1 inhibitors. An immunoprecipitation-western blot analysis showing the disruption of the Rb:Raf-1 interaction by the Raf-1 peptide-penetratin conjugate as well as three compounds identified from the NSC library.

U937 cells were serum starved for 48 hours and subsequently serum stimulated for 2 hours in the presence or absence of 20 μM of the compounds. Both (1) and (2) inhibited the binding of Raf-1 to Rb significantly (IC$_{50}$ of 81±4 nM and 283±46 nM, respectively), as seen by immunoprecipitation-Western blot analysis (FIG. 1d); Raf-1 peptide conjugated to penetratin was used as a positive control. Thus it appears that these two compounds were capable of disrupting the Rb:Raf-1 interaction in vitro and in cultured cells.

EXAMPLE 8

Disclosed Compound 3a Selectively Inhibits Rb:Raf-1 Binding

Figure 2A:
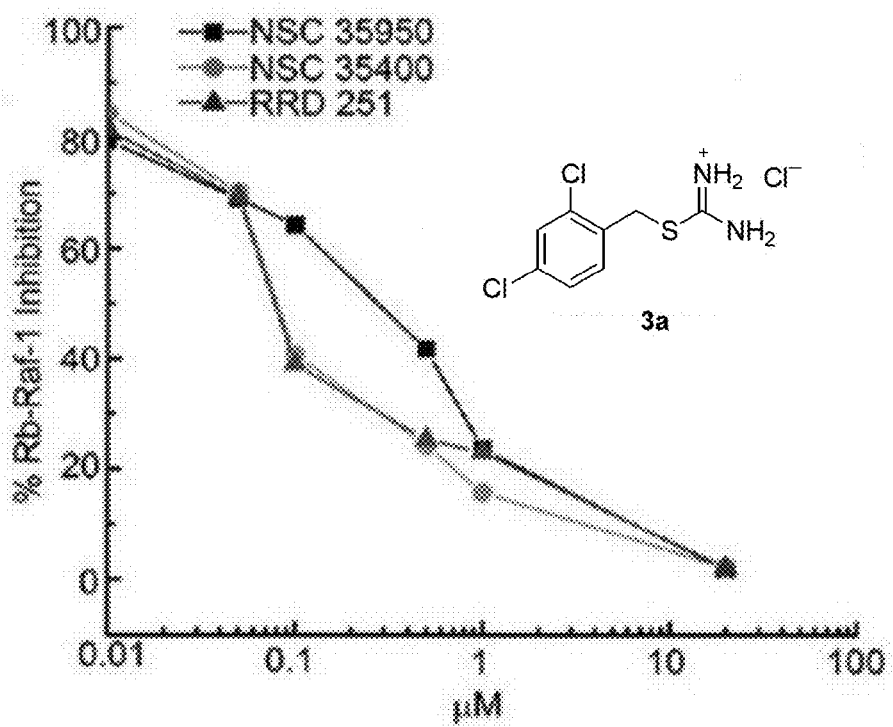
FIG. 2A: Compounds (1), (2), and 3a disrupted the Rb:Raf-1 interaction with high potency. $IC_{50}$ values were determined using ELISA.
Figure 2B:
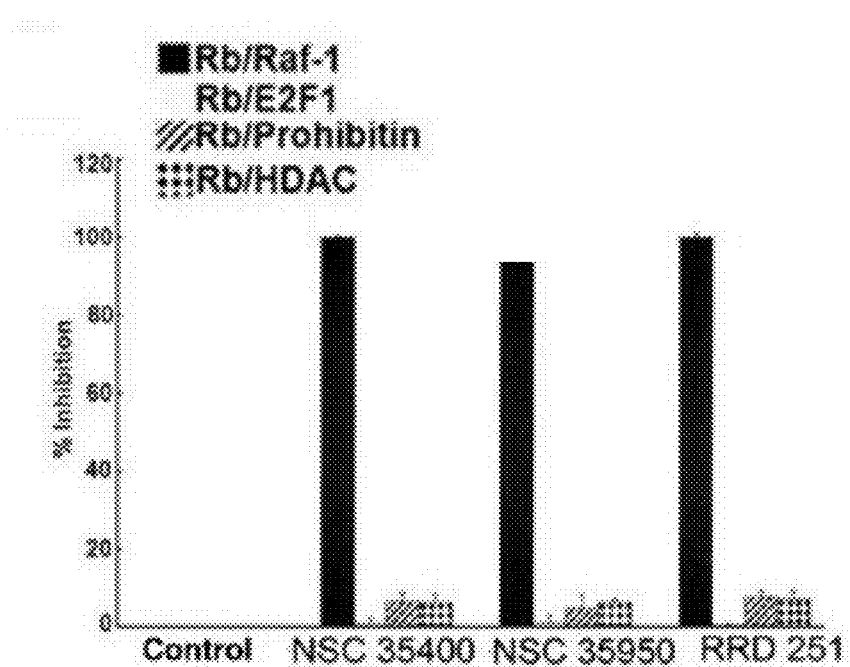
FIG. 2B: Inhibitors of Rb:Raf-1 interaction at 20 µM concentration do not inhibit other binding partners in ELISA.
Figure 2B:
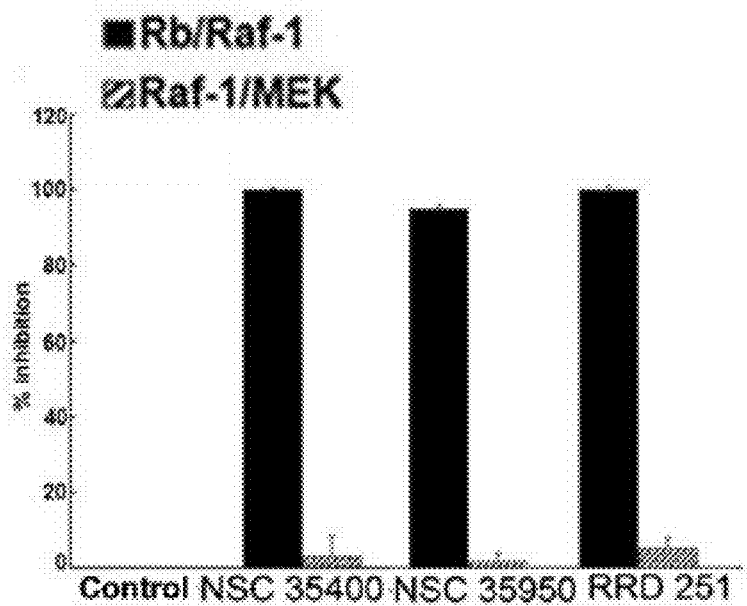
Figure 2C:
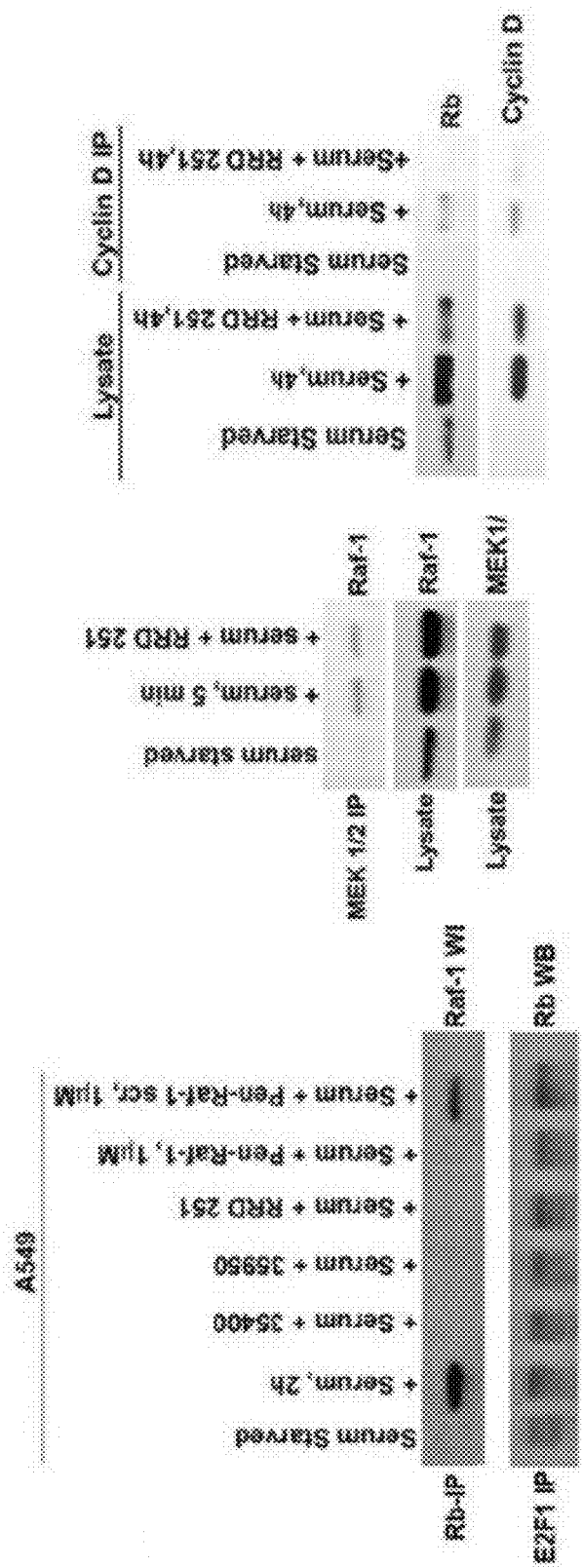
FIG. 2C: Serum-stimulated binding of Raf-1 to Rb were inhibited by Rb:Raf-1 disruptors as well as a Raf-1 peptide conjugated to penetratin. Specificity of the disruption was assessed by IP-western blots; the drugs do not inhibit the binding of E2F1 to Rb (left panel) or MEK to Raf-1 (middle panel). Compound 3a tended to reduce the levels of cyclin D as well as its association with Rb (right panel).
Figure 2D:
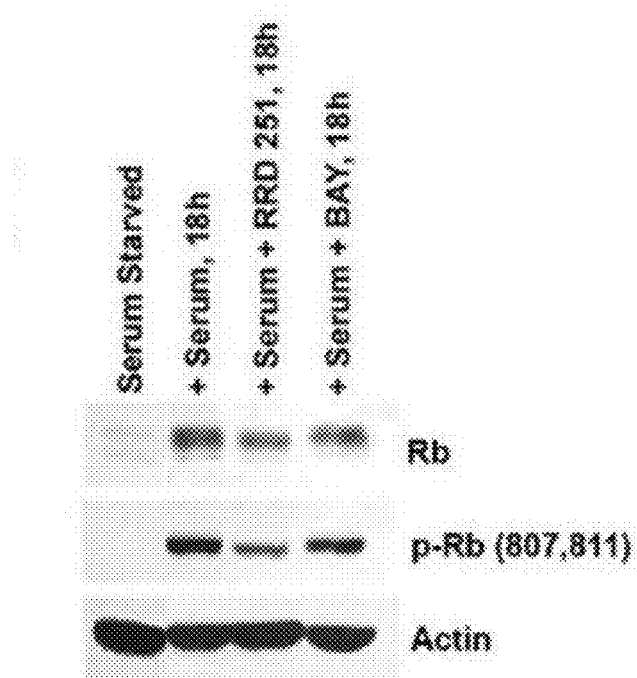
FIG. 2D: Treatment with compound 3a reduced Rb phosphorylation significantly. Quiescent A549 cells were serum stimulated in the presence or absence of 3a or BAY43-9002 and RB phosphorylation determined by western blotting.
Figure 2E:
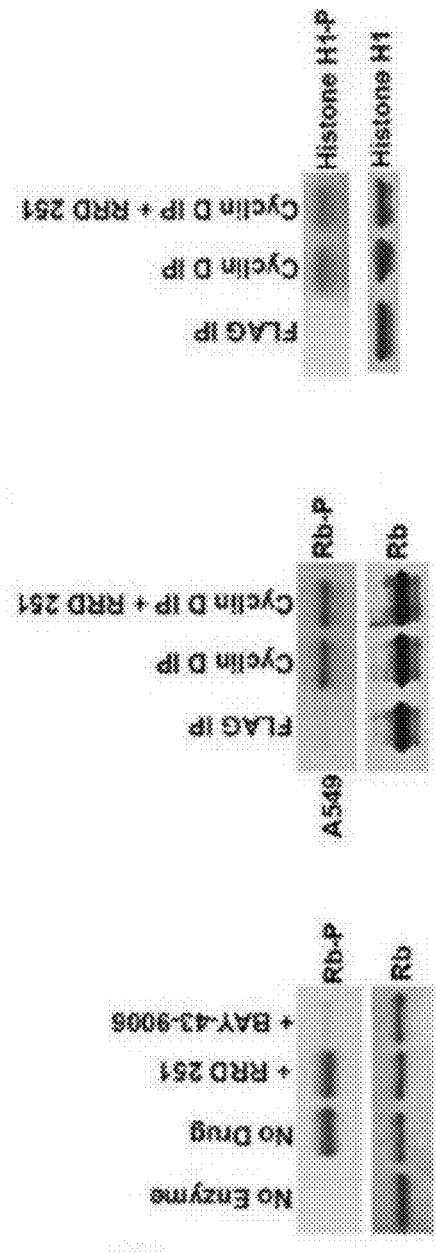
FIG. 2E: Compound 3a does not inhibit Raf-1, cyclin D or E kinase activities in vitro kinase assays.
Figure 2F:
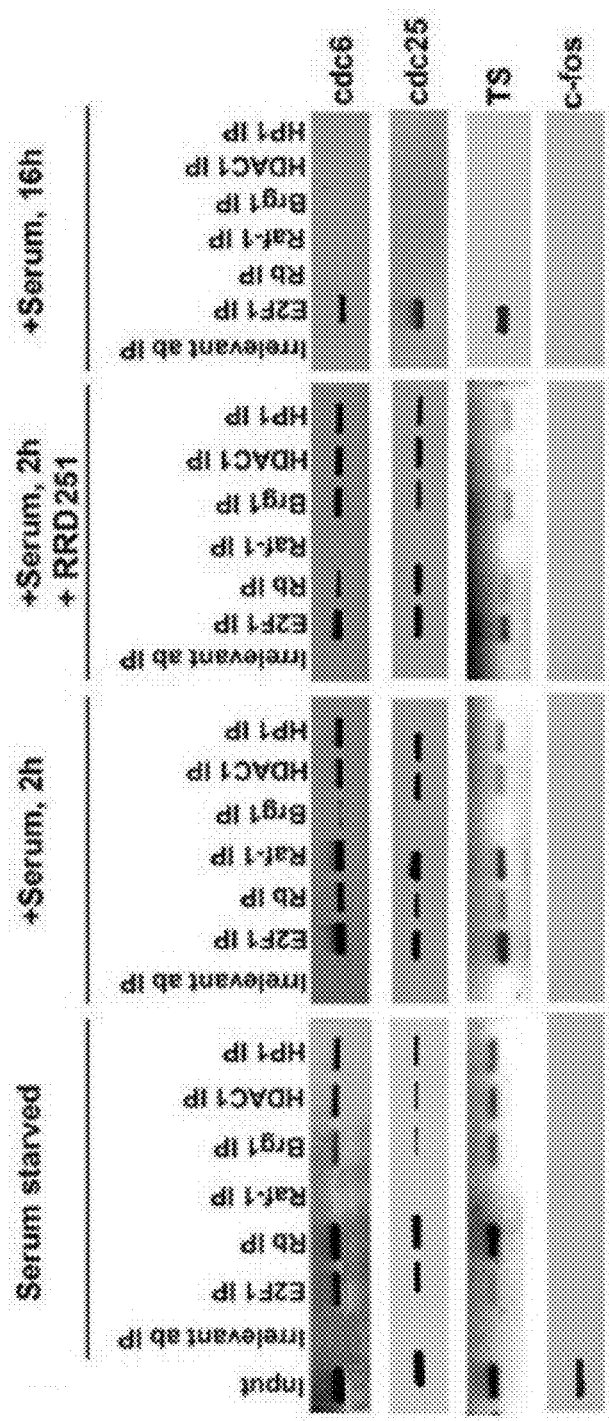
FIG. 2F: ChIP assays show that Brg1, not Raf-1 is present on quiescent A549 cdc6, cdc25A and TS promoters. Upon serum stimulation, Brg1 is dissociated from both promoters, correlating with Raf-1 binding. Serum stimulation in the presence of 3a causes the dissociation of Raf-1 and retention of Brg1 on E2F1 responsive promoters. Serum stimulation for 16 hours causes dissociation of Rb, Raf-1, HP1, Brg1, and HDAC1 from the promoters. An irrelevant antibody was used as a control for immunoprecipitations; c-fos promoter was used as a negative control.

As shown in FIG. 1a, (1) and (2) consist each of a benzyl-isothiourea derivative and a phenyl-based counter ion. To determine potency of the benzyl-isothiourea group versus the phenyl counter ions, these compounds were compared to 3a (RRD-251, FIG. 2a), which had chloride as the counter ion. (1) had an IC$_{50}$ of 81±4 nM and (2) had an IC$_{50}$ of 283±46 nM, while 3a showed a value of 77±3.6 nM (FIG. 2a). Next, the selectivity of the Rb:Raf-1 binding disruptors in vitro was determined to be selective for Rb:Raf-1 over Rb/E2F1, Rb/HDAC1, Rb/prohibitin and Raf-1/Mek association (FIG. 2b). FIG. 2a shows that 3a is as effective as (1) at inhibiting Rb:Raf-1 binding in an ELISA assay. In addition, serum stimulation of binding of Rb to Raf-1 in A-549 cells was inhibited by 3a and the Raf-1 peptide but not a scrambled peptide coupled to penetratin (FIG. 2c, left panel). In contrast, the Rb binding to E2F1 and serum-mediated binding of Raf-1 to Mek1/2 were not affected by 3a further confirming the selectivity of this small molecule for Rb:Raf-1 (FIG. 2c left and middle panels). It was found that the level of cyclin D as well as its association with Rb was reduced by 3a (FIG. 2C, right panel). Examination of lysates from cells treated with 3a for 18 hours showed a marked reduction in Rb phosphorylation, as seen by western blotting using an antibody to Rb or one that specifically recognizes Rb phosphorylated on serines 807 and 811; treatment of cells with BAY43-9006 (sorafenib) did not seem to have any effect on Rb phosphorylation (FIG. 2d). Further, in vitro assays showed that 3a did not affect the kinase activities associated with Raf-1, cyclin D or cyclin E (FIG. 2e). These results suggest that the reduction in Rb phosphorylation in cells treated with 3a is due to a disruption in the association of Raf-1 with Rb and not due to an inhibition of the kinase activity of Raf-1.

Since serum is known to stimulate the binding of Raf-1 to Rb and leads to the dissociation of the co-repressor Brg-1 from E2F-responsive proliferative promoters like cdc6, cdc25 and TS promoters, it was hypothesized that 3a may interfere with this process. Chromatin immunoprecipitation assays demonstrated that Raf-1 binding to the above promoters upon serum-stimulation is disrupted by pre-treatment of cells with 3a. Furthermore, the corresponding dissociation of the co-repressor Brg-1 from these promoters was also inhibited by 3a. This suggests that 3a can modulate the transcriptional regulatory functions of Rb in the nucleus by modulating its phosphorylation status and affecting its interaction with chromatin remodeling proteins like Brg-1. Binding of E2F1, HDAC1 and HP1 was not affected.

EXAMPLE 9

Compound 3a Inhibited Osteosarcoma Proliferation

Given the selectivity of 3a described in FIGS. 1 and 2 above for disrupting the Rb:Raf-1 interaction, it was examined if 3a can inhibit the proliferation of cells and whether such an inhibition required a functional Rb gene. Two osteosarcoma cell lines, U2-OS (which has wild type Rb) and Saos-2 (which is Rb null), were rendered quiescent by serum starvation and subsequently stimulated with serum in the presence or absence of 20 µM 3a for 18 hours and S-phase entry was assessed by measuring BrdU incorporation. 3a inhibited S-phase entry of U2-OS cells; but it had little effect on Saos-2 cells, suggesting that 3a inhibits cell proliferation in an Rb-dependent manner.

EXAMPLE 10

Compound 3a Inhibited Epithelial Lung Cancer Cell Proliferation

To further confirm that 3a requires a functional Rb to inhibit tumor cell proliferation, A549 cells (human epithelial lung carcinoma) were stably transfected with two different shRNA constructs (sh6 and sh8) to knock down Rb expression. As expected, A549 cells stably expressing the Rb shRNAs had significantly less Rb protein compared to parental A549 cells (FIG. 3*b*). 3a was very effective at inhibiting S-phase entry in parental A549 cells but had no effect on cells stably expressing sh6 and sh8, which lacked Rb (FIG. 3*c*). This result confirms that 3a arrests cell proliferation in a Rb dependent manner.

EXAMPLE 11

Compound 3a Inhibited Non-Small Cell Lung Carcinoma Proliferation

Because many cancers contain more than one mutation in tumor suppressor genes or oncogenes, we determined the ability of 3a to inhibit proliferation in cell lines containing alterations in key regulatory genes. Compound 3a was able to inhibit 90% of S-phase entry in the H1650 non-small cell lung cancer (NSCLC) cell line that carry mutations in the tyrosine kinase domain of EGFR (FIG. 3*d*).

EXAMPLE 12

Compound 3a Inhibited Proliferation of 3 Pancreatic Cancer Cell Lines

Figure 3A:
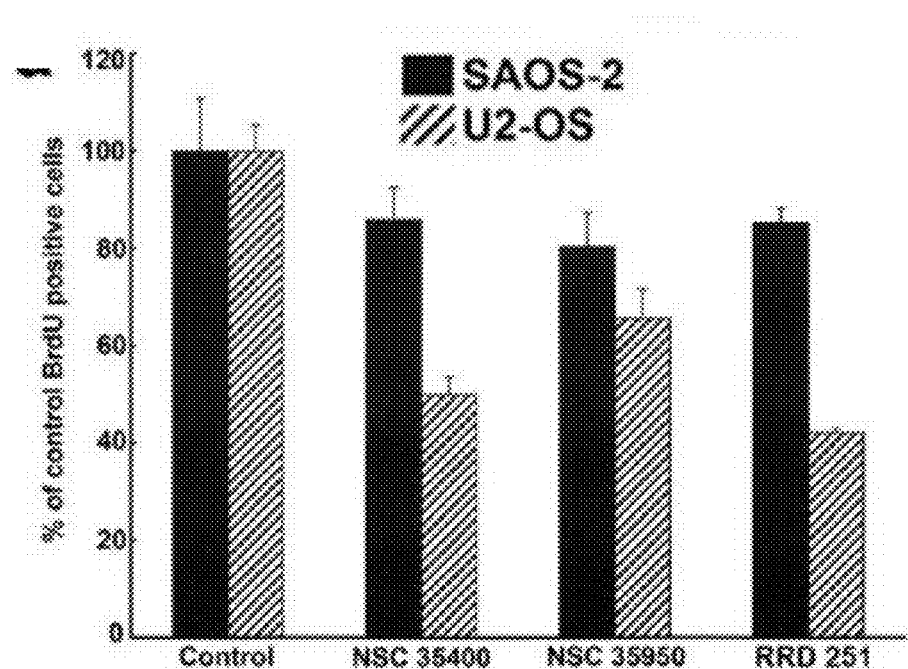
FIG. 3A: S-phase entry of serum stimulated U2-OS or Saos-2 cells in the presence or absence of Rb:Raf-1 inhibitors (20 µM) was assessed by BrdU incorporation. The Rb-Raf-1 disruptors selectively arrest Rb positive U2OS cells.
Figure 3B:
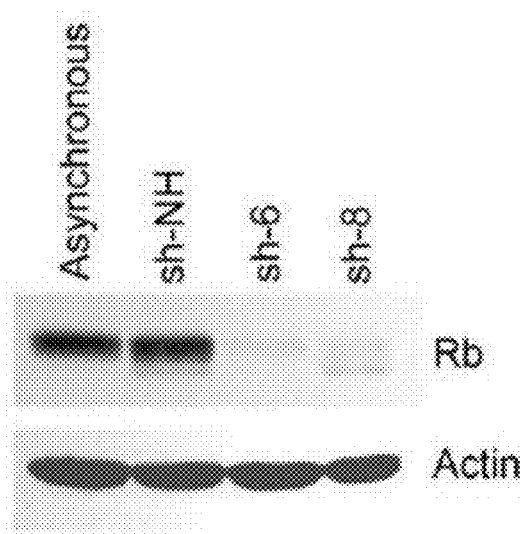
FIG. 3B: A549 cells stably transfected with a non-homologous shRNA construct as the control, or with two different 16 shRNA constructs that target Rb. Cells transfected with the Rb shRNAs show greatly reduced Rb levels.
Figure 3C:
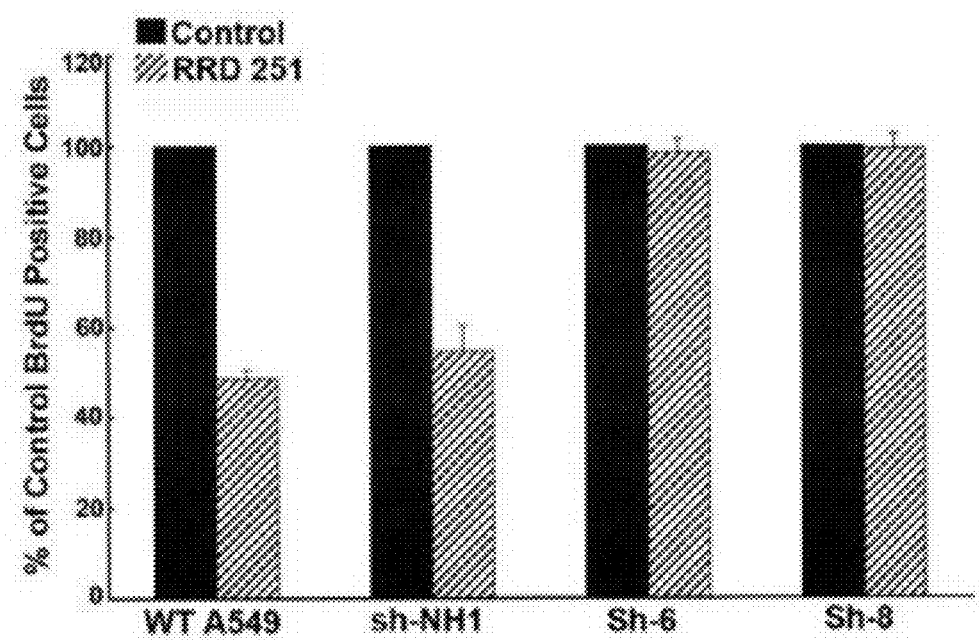
FIG. 3C: BrdU incorporation assay showing that 20 µm of 3a does not inhibit the proliferation of A549 cells overexpressing shRNA constructs to Rb, but arrests wild-type A549 cells as well as those harboring a non-homologous, control shRNA.

Using the methods of the preceding examples, it was found that compound 3a could inhibit S-phase entry by 50-65% in pancreatic cancer cells such as Aspc1, PANC1, and CAPAN2 that harbor a non-functional p16INK4a gene (FIG. 3*d*).

EXAMPLE 13

Compound 3a Inhibited Proliferation of Two Glioblastoma Cell Lines

Using the methods of the preceding examples, compound 3a also inhibited S-phase entry of two glioblastoma cell lines U87MG and U251MG, both of which are null for p16 and PTEN.

EXAMPLE 14

Compound 3a Inhibited Metastatic Breast Cancer Cell Proliferation

The metastatic human breast cancer cell line MDA-MB-231 harbors a K-Ras mutation and overexpresses EGFR. Using the methods of the preceding examples, compound 3a inhibited MDA-MB-231 proliferation by 56% (FIG. 3*d*).

EXAMPLE 15

Compound 3a Inhibited Melanoma Cell Proliferation

A V600E mutation in the B-Raf oncogene is associated with 66% of melanomas and leads to an over-activation of phospho-Erk signaling. The A375 melanoma cell line harbors the V600E B-Raf mutation. Using the methods of the preceding examples, 3a was inhibited 58% of S-phase entry in this cell line.

EXAMPLE 16

Compound 3a Inhibited Prostate Cancer Cell Proliferation

Prostate cell lines LNCaP and PC3 both contain mutations in K-Ras and PTEN genes. Using the methods of the preceding examples, compound 3a inhibited proliferation 86% and 35% respectively (FIG. 2*d*). These results indicate that disruption of Rb:Raf-1 interaction could inhibit the proliferation of cell lines harboring a wide array of gene mutations.

EXAMPLE 17

Figure 3E:
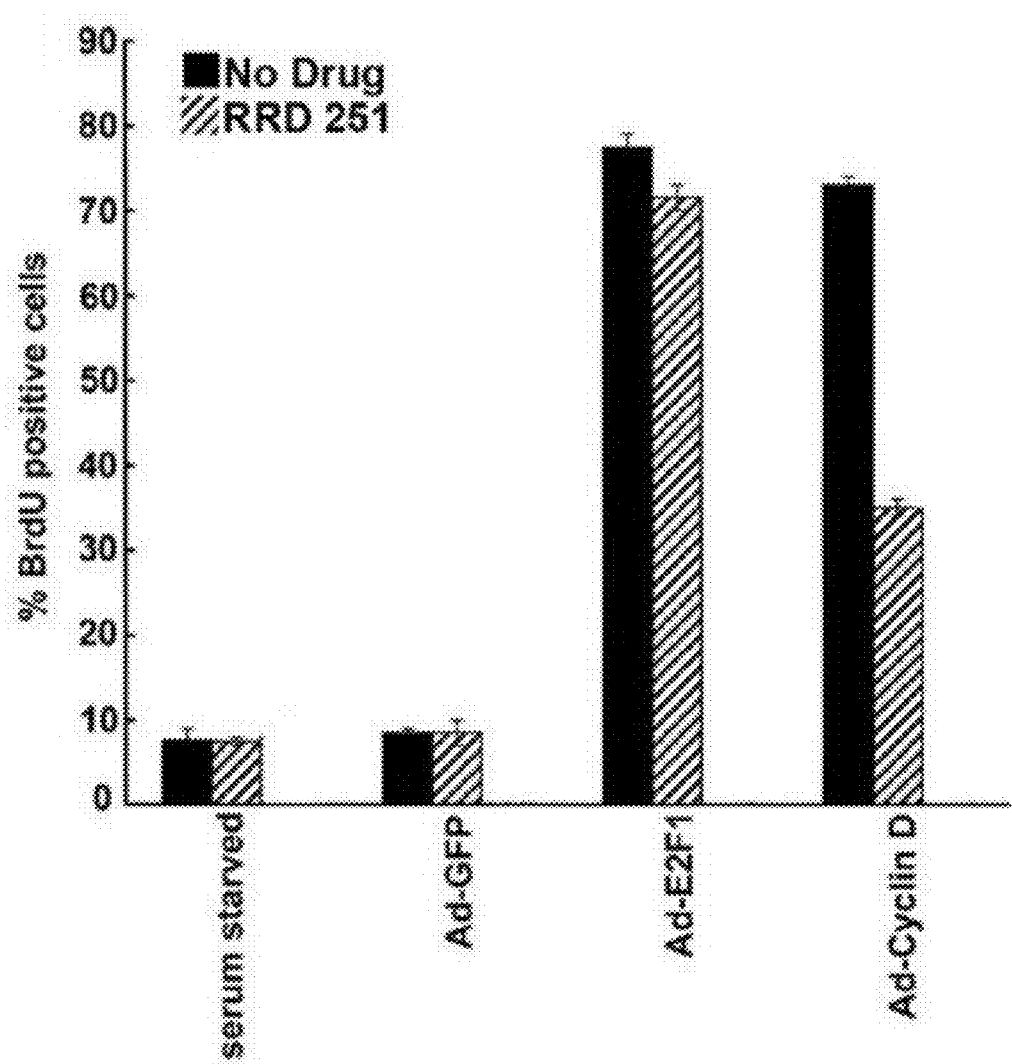
FIG. 3E: Over expression of E2F1 is sufficient to overcome cell cycle arrested media by 3a, while cyclin D over expression has only a partial effect.

Anticancer Activity of Disclosed Compounds is Via Disruption of Rb:Raf-1 Interaction It was hypothesized that if compound 3a selectively targets the Rb:Raf-1 interaction, the forced expression of a downstream target or Rb such as E2F1, but not of the upstream regulator Cyclin D, would rescue the anti-proliferative effects of compound 3a. To this end, A549 cells were infected with Ad-E2F1 or Ad-cyclin D, in the presence of 20 µM of 3a for 36 h. Ad-GFP infected cells were used as a control. BrdU incorporation assays showed that ectopic expression of E2F1 efficiently overcame the anti-proliferative activity of 3a, whereas over-expression of cyclin D had only a partial effect (FIG. 3*e*). Without wishing to be bound by theory, these results provide support for the hypothesis that the association of Raf-1 with Rb may be needed for the complete inactivation of Rb by the kinases associated with cyclins D and E, and thus that the activity of compound 3a in disrupting this association may lead to its anticancer effects.

EXAMPLE 18

Disclosed Compounds Disrupt Angiogenesis

Figure 3F:
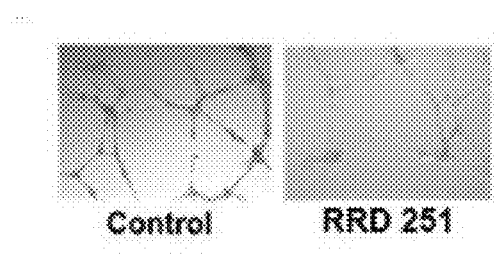
FIG. 3F: Compounds (1), (2) and 3a all inhibit angiogenic tubule formation in matrigel at 20 µM.
Figure 3G:
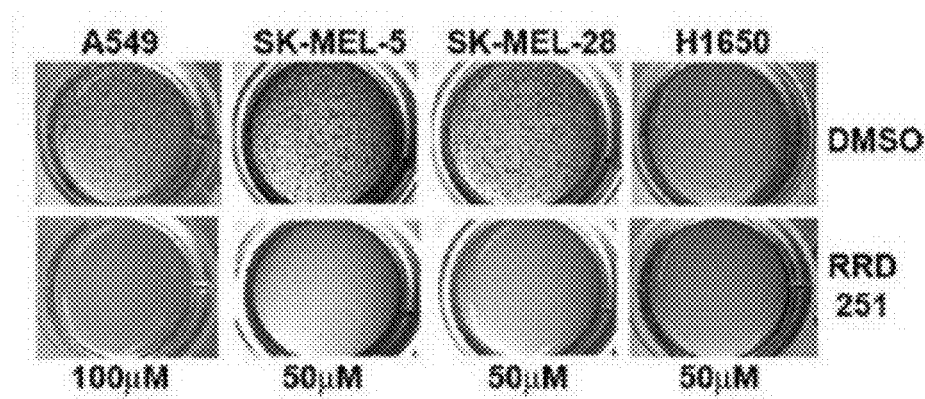
FIG. 3G: Compound 3a inhibits adherence independent growth of several cell lines in soft agar.

An experiment was performed to determine whether angiogenic tubule formation could be inhibited by the disclosed compounds. Human aortic endothelial cells (HAECs) were grown in matrigel in the presence or absence of 20 µM (1), (2), or 3a. It was found that while angiogenic tubules formed in control wells, the disclosed disruptors of the Rb:Raf-1 interaction significantly inhibited the angiogenic tubule formation (FIG. 3f).

EXAMPLE 19

Disclosed Compounds Inhibit Anchorage Independent Tumor Growth (Soft Agar)

Experiments were also carried out to examine the effect of 3a in inhibiting the adherence-independent growth of cancer cells in soft agar. It was found that compound 3a significantly inhibited the growth of A549 (human epithelial lung carcinoma), H1650 (NSCLC), SK-MEL-5, SK-MEL-28 (melanoma), and PANC1 (pancreatic) cells in soft agar. The ability of 3a to inhibit cell proliferation, adherence-independent growth and angiogenesis demonstrates that it has properties desirable in anti-cancer drugs.

EXAMPLE 20

Compounds 3a & 9a Significantly Inhibited Human Tumor Line In Vivo

Figure 4A:
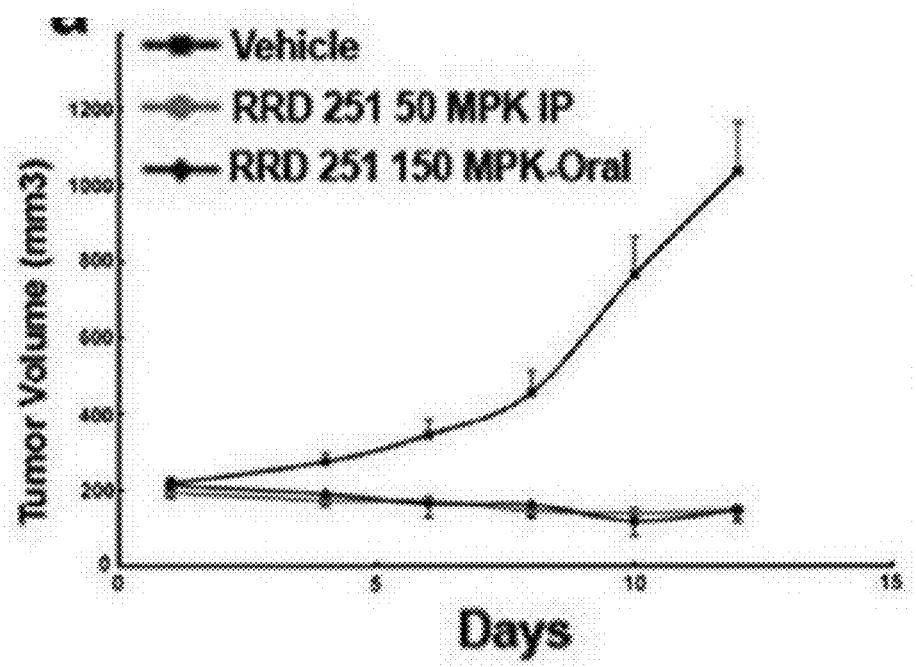
FIG. 4A: Compound 3a inhibits human tumor growth in nude mice. A549 cells xenotransplanted bilaterally into the flanks of athymic nude mice were allowed to grow for 14 days until tumor volume reached 200 $mm^3$; daily administration of 50 milligrams/kilogram (mpk) (i.p) and 150 mpk (oral) of 3a can completely inhibit tumor growth.
Figure 4B:
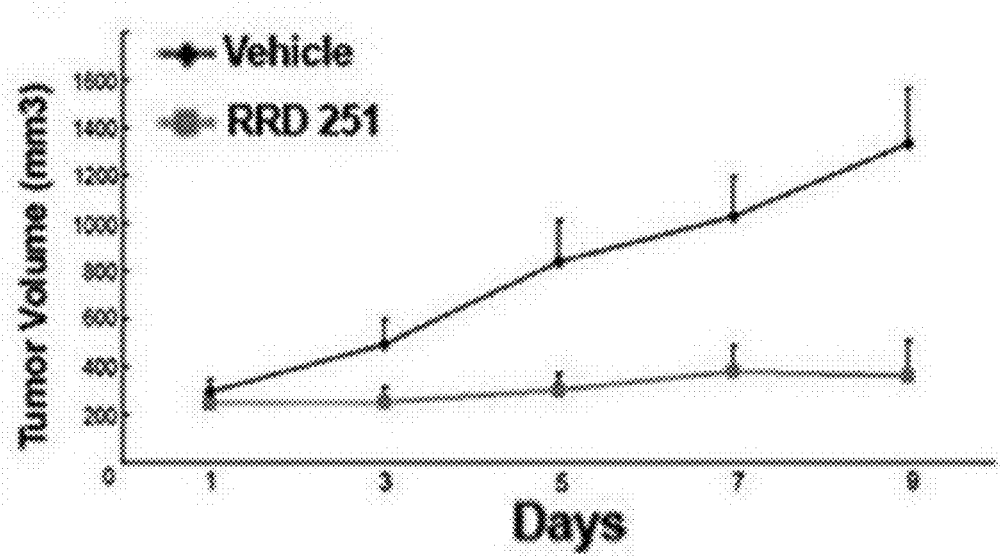
FIG. 4B: Compound 3a, 50 mpk administered by i.p. injection inhibited H1650 xenograft tumor growth in nude mice.
Figure 4C:
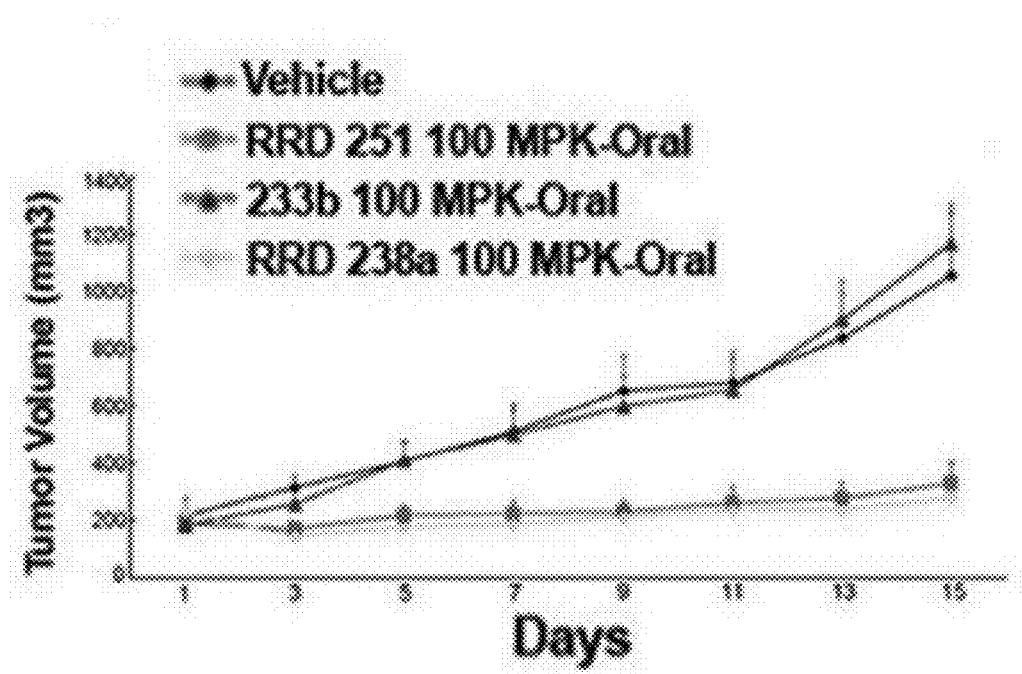
FIG. 4C: Compound RRD-238a, a compound similar to 3a, was also able to arrest tumor growth significantly in nude mice in a similar experiment using A549 cells. RRD238a and RRD251 were administered orally at 100 mpk.
Figure 4D:
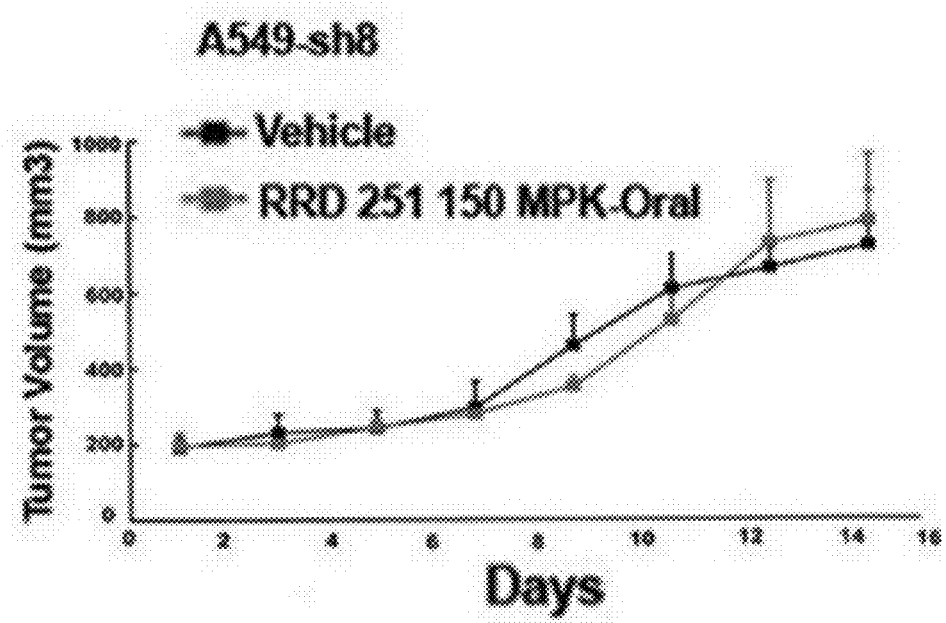
FIG. 4D, FIG. 4E: Inhibition of tumor growth was dependent on a functional Rb protein. A549-sh6 and A549-sh8 cells ($1 \times 10^7$) were implanted into the flanks of nude mice. The tumors were allowed to grow until they reached a volume of 200 mm3. Compound 3a was administered at 150 mpk orally and the control group received the vehicle. Compound 3a was unable to inhibit tumor growth in tumors lacking Rb protein.
Figure 4E:
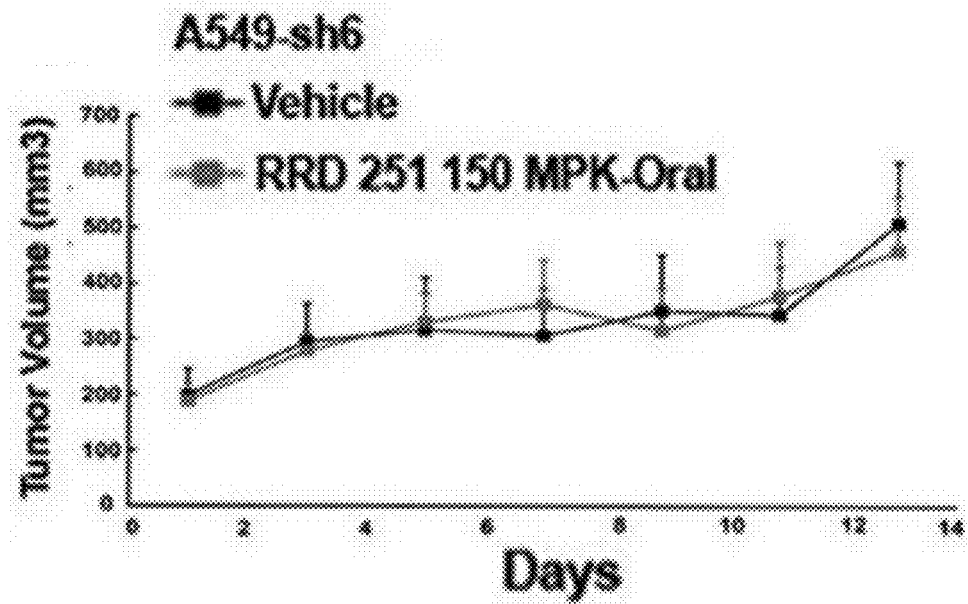

Experiments were performed to assess whether compounds 3a and 9a could inhibit human tumor growth in vivo using a nude mice xenograft model. Athymic nude mice were implanted with $1 \times 10^7$ A549 cells bilaterally and the tumors were allowed to reach 200 mm$^3$ in size before treatment began. FIG. 4A shows that tumors from vehicle treated mice grew to an average size of 1039±128 mm$^3$. In contrast, tumors treated with either 50 milligrams per kilogram (mpk)/day (i.p.) or 150 mpk/day (oral) of 3a did not grow (50 mpk: 144±20 mm$^3$; 150 mpk 148±32 mm$^3$). Similar results were observed with H1650 in that 3a (50 mpk/day) inhibited the growth of these tumors significantly (FIG. 4b; 2185±326 mm$^3$ in vehicle treated animals compared to 557±76 mm3 in 3a treated animals). Similarly, compound 9a (RRD-238a), an analogue of 3a, was equally effective in inhibiting the growth of A549 tumors in nude mice (FIG. 4c). Furthermore, to examine whether 3a could affect the growth of tumors lacking Rb in vivo, sh6 and sh8 (shRNA for Rb) cell lines were implanted into the flanks of nude mice. The mice were given 3a orally at 150 mpk and the control groups were administered the vehicle. Mice harboring SH6 and SH8 tumors and treated with 3a did not respond, they continued to grow at the rate of the wild type A549 tumors (FIG. 4d, e).

Figure 4F:
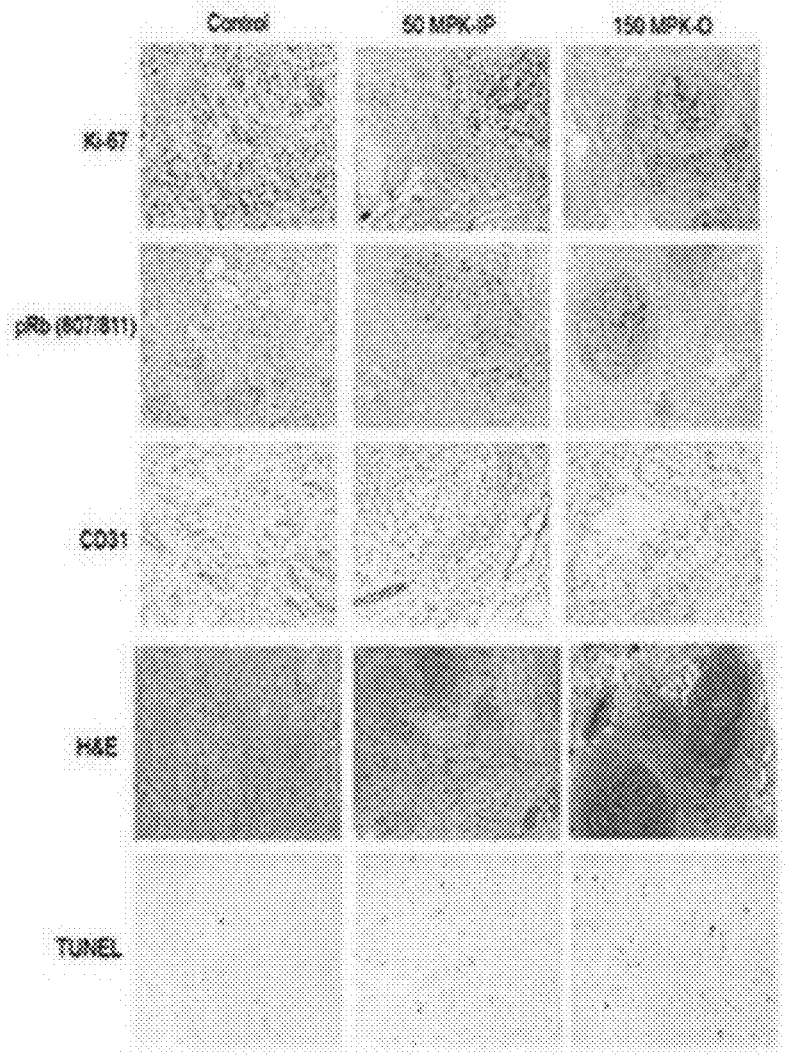
FIG. 4F: Immunohistochemical staining of tumors from mice treated with 3a. Tumors were stained with Ki-67 for proliferation, pRb for cell cycle, and CD31 for angiogenesis. A dose dependent increase in apoptosis is seen by TUNEL staining.
Figure 4G:
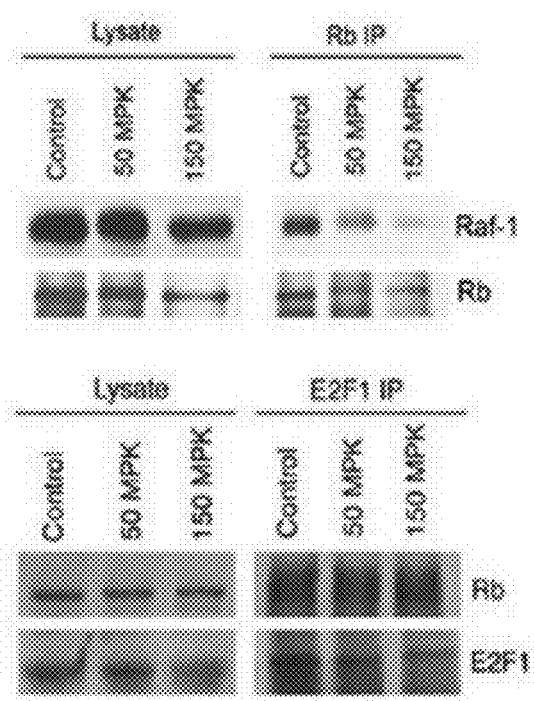
FIG. 4G: Both doses of compound 3a inhibit the Rb:Raf-1 interaction in tumor lysates without inhibiting Rb-E2F1 interaction, as seen by IP-Western blots.
Figure 4H:
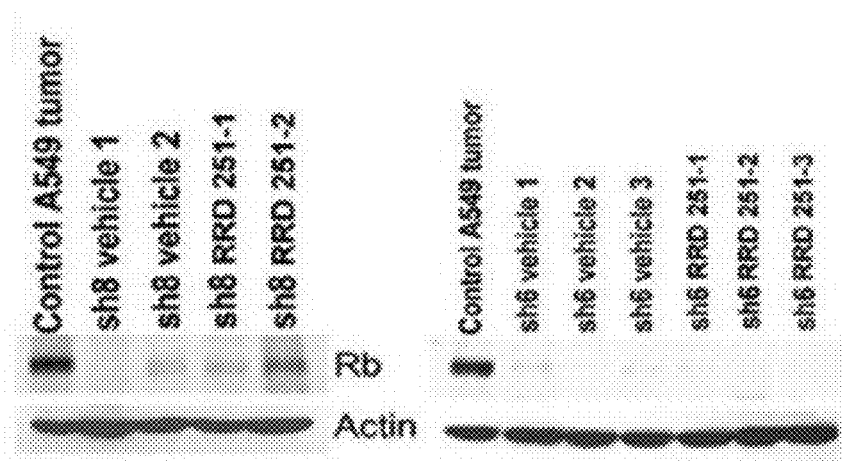
FIG. 4H: Tumors maintained downregulated Rb expression till the completion of the experiment.

At the end of the drug treatment, the A549 tumors were removed from the mice and fixed in formalin or snap frozen in liquid nitrogen for further histochemical analysis. The tumors were analyzed by immunohistochemistry staining with hematoxylin and eosin (H&E), TUNEL, Ki-67, phospho-Rb (807,811), and CD-31. Histopathological analysis revealed a significant inhibition of proliferation as seen by a reduction in Ki-67 staining (FIG. 4f). The tissues showed a reduction in phosphorylation of Rb as seen by staining with an antibody to phospho-Rb (FIG. 4f). The tumors also showed a reduction in microvasculature, as seen by CD31 staining (FIG. 4f). A dose dependent increase in apoptosis (TUNEL) was observed in tumors treated with 3a, probably as a result of inhibition of angiogenesis (FIG. 4f). Tumors were homogenized and lysates were prepared to assess the inhibition of Rb:Raf-1 interaction in vivo. 3a was found to inhibit Rb:Raf-1 but not Rb/E2F1 interaction in the tumor xenografts (FIG. 4g). To examine whether the sh6 and sh8 tumors maintained downregulation of Rb, lysates made from the sh6 and sh8 tumors at the end of the experiment and a western blot was done for Rb, It was found that these tumors lacked Rb, further confirming that compound 3a specifically targets the Rb:Raf-1 protein interaction to inhibit cell proliferation and tumor growth (FIG. 4h).

Discussion

The Ras/Raf/Mek/MAPK cascade is a proliferative pathway induced by a wide array of growth factors and is activated in many human tumors. It has been shown that signaling pathways through the MAP kinase cascade do not proceed in a linear fashion, but rather that they have been found to have substrates outside the cascade as well. Without wishing to be bound by theory, in this context, the Rb protein appears to be an important cellular target of the Raf-1 kinase outside the MAP kinase cascade. The binding of Raf-1 to Rb was found to occur only in proliferating cells and contributed to cell cycle progression. Further, it was found that the level of Rb:Raf-1 interaction was elevated in NSCLC tissue, suggesting that it may have contributed to the oncogenic process. These observations support the hypothesis that targeting the Rb:Raf-1 interaction with the disclosed compounds is a viable method to develop anticancer drugs.

The cell-permeable, orally available, and target specific small molecule compound 3a, can maintain the tumor suppressor functions of Rb. The in vitro results indicate that compound 3a selectively inhibits the Rb:Raf-1 interaction without targeting the binding partners of Rb and Raf-1, such as E2F1, prohibitin, HDAC1 and MEK1/2. Further, compound 3a functions by inhibiting the interaction of Raf-1 and Rb without inhibiting Raf-1 kinase activity or the kinase activity associated with cyclins D or E. Also, compound 3a inhibited cell cycle and decreased the levels of cyclin D while cdk activity was unaffected. Compound 3a demonstrated Rb dependence to inhibit cell cycle progression and tumor growth in cell lines. These results further confirm the specificity of 3a for targeting Rb:Raf-1. Mice harboring A549 tumors responded to treatment with 3a administered by i.p. or oral gavage. Tumor tissue displayed a decrease in proliferation, Rb phosphorylation, and angiogenesis and an increase in apoptosis. Importantly, A-549 tumors where Rb was knockdown are resistant to 3a, further suggesting that 3a inhibits tumor growth by targeting the Rb:Raf-1 interaction.

These results show that the mechanism of 3a mediated growth arrest is likely by targeting the Rb:Raf-1 interaction. Aberrant signaling mechanisms surrounding the Ras/MAPK and Rb/E2F1 pathways are commonly present in cancers. The disclosed compounds, such as compound 3a, could inhibit S-phase entry in potentially 35%-90% of all of the cell lines. Based on the substantial in vitro and in vivo results disclosed herein, it is believed that the disclosed compounds, in particular compound 3a, are excellent candidates for the treatment of cancer patients whose tumors harbor genetic aberrations that lead to inactivation of Rb by Raf-1.

REFERENCES

The entire teachings of each document cited herein, including the following, are incorporated by reference.

Alavi A, Hood J D, Frausto R, Stupack D G, Cheresh D A. Role of Raf in vascular protection from distinct apoptotic stimuli. *Science* 2003, 301(5629), 94-96.

Arkin M R, Wells J A. Small-molecule inhibitors of protein-protein interactions: progressing towards the dream. *Nature Reviews Drug Discovery* 2004, 3(4), 301-317.

Bagchi S, Weinmann R, Raychaudhuri P. The retinoblastoma protein copurifies with E2F-I, an E1A-regulated inhibitor of the transcription factor E2F. *Cell* 1991; 65(6): 1073-82.

Beijersbergen R L, Bernards R. Cell cycle regulation by the retinoblastoma family of growth inhibitory proteins. [Review]. *Biochim Biophys Acta* 1996; 1287(2-3):103-20.

Chau B N, Wang J Y. Coordinated regulation of life and death by RB. *Nat Rev Cancer* 2003; 3(2):130-8.

Chellappan S, Kraus V B, Kroger B, et al. Adenovirus E1A, simian virus 40 tumor antigen, and human papillomavirus E7 protein share the capacity to disrupt the interaction between transcription factor E2F and the retinoblastoma gene product. Proc Natl Acad Sci USA 1992; 89:4549-53.

Chellappan S P, Hiebert S, Mudryj M, Horowitz J M, Nevins J R. The E2F transcription factor is a cellular target for the RB protein. *Cell* 1991; 65(6):1053-61.

Chittenden T, M. L D, Jr K W G. RB associates with an E2F-like, sequence-specific DNA-binding protein. *Cold Spring Harb Symp Quant Biol* 1991; 56:187-95.

Classon M, Dyson N. p107 and p130: versatile proteins with interesting pockets. *Exp Cell Res* 2001; 264(1):135-47.

Classon M, Salama S, Gorka C, Mulloy R, Braun P, Harlow E. Combinatorial roles for pRB, p107, and p130 in E2F-mediated cell cycle control. *Proc Natl Acad Sci USA* 2000; 97(20):10820-5.

Cobrinik D. Pocket proteins and cell cycle control. *Oncogene* 2005, 24(17), 2796-2809.

Dasgupta P, Betts V, Rastogi S, et al. Direct binding of apoptosis signal regulating kinase 1 to retinoblastoma protein: novel links between apoptotic signaling and cell cycle machinery. *Journal of Biological Chemistry* 2004, 279(37), 38762-38769.

Dasgupta P, Betts V, Rastogi S, et al. Direct binding of apoptosis signal-regulating kinase 1 to retinoblastoma protein: novel links between apoptotic signaling and cell cycle machinery. *J Biol Chem* 2004; 279(37):38762-9.

Dasgupta P, Chellappan S, Nicotine-mediated cell proliferation and angiogenesis: New twists to an old story. *Cell Cycle* 2006, in press.

Dasgupta, P, Rastogi, S, Pillai, S, Ordonez-Ercan, D, Morris, M. et al. Nicotine induces cell proliferation by beta-arrestin-mediated activation of Src and Rb:Raf-1 pathways. *Journal of Clinical Investigation* 2006, 116, 2208-2217.

Dasgupta, P, Sun, J Z, Wang, S, Fusaro, G, Betts, V. et al. Disruption of the Rb:Raf-1 interaction inhibits tumor growth and angiogenesis. *Molecular and Cellular Biology* 2004, 24, 9527-9541.

de Bruin A, Maiti B, Jakoi L, Timmers C, Buerki R, Leone G. Identification and characterization of E2F7, a novel mammalian E2F family member capable of blocking cellular proliferation. *J Biol Chem* 2003; 278(43):42041-9.

DeGregori J, Leone G, Miron A, Jakoi L, Nevins J R. Distinct roles for E2F proteins in cell growth control and apoptosis. *Proc Natl Acad Sci US A* 1997; 94(14):7245-50.

DeGregori J, Leone G, Ohtani K, Miron A, Nevins J R. E2F-1 accumulation bypasses a G1 arrest resulting from the inhibition of G1 cyclin-dependent kinase activity. *Genes Dev* 1995; 9(23):2873-87.

Derossi D, Chassaing G, Prochiantz A. Trojan peptides: the penetratin system for intracellular delivery. *Trends Cell Biol* 1998; 8(2):84-7.

Derossi, D, Joliot, A H, Chassaing, G, Prochiantz, A. The 3rd Helix of the Antennapedia Homeodomain Translocates through Biological-Membranes. *Journal of Biological Chemistry* 1994, 269, 10444-10450.

Di Stefano L, Jensen M R, Helin K. E2F7, a novel E2F featuring DP-independent repression of a subset of E2F-regulated genes. *Embo J* 2003; 22(23):6289-98.

Dyson N, Guida P, McCall C, E. H. Adenovirus E1A makes two distinct contacts with the retinoblastoma protein. *J Virol* 1992; 66(7):4606-11.

Dyson N, Howley P M, Munger K, Harlow E. The human papilloma virus-16 E7 oncoprotein is able to bind to the retinoblastoma gene product. *Science* 1989; 243(4893):934-7.

Guisado, O, Martinez, S, Pastor, J. A novel, facile methodology for the synthesis of N,N'-bis(tert-butoxycarbonyl)-protected guanidines using polymer-supported carbodiimide. *Tetrahedron Letters* 2002, 43, 7105-7109.

Hakem R, Mak T W. Animal models of tumor-suppressor genes. *Annu Rev Genet.* 2001; 35:209-41.

Harbour J W, Luo R X, Dei Santi A, Postigo A A, Dean D C. Cdk phosphorylation triggers sequential intramolecular interactions that progressively block Rb functions as cells move through G1. *Cell* 1999, 98(6), 859-869.

Harbour, J W, Dean, D C. Rb function in cell-cycle regulation and apoptosis. *Nature Cell Biology* 2000, 2, E65-E67.

Harbour, J W, Dean, D C. The Rb/E2F pathway: expanding roles and emerging paradigms. *Genes & Development* 2000, 14, 2393-2409.

Hood J D, Cheresh D A. Targeted delivery of mutant Raf kinase to neovessels causes tumor regression. *Cold Spring Harbor Symposium on Quantitative Biology* 2002, 67, 285-291.

Ishida S, Huang E, Zuzan H, et al. Role for E2F in control of both DNA replication and mitotic functions as revealed from DNA microarray analysis. *Mol Cell Biol* 2001; 21(14): 4684-99.

Johnson D G, Schneider-Broussard R. Role of E2F in cell cycle control and cancer. *Front Biosci* 1998; 3:d447-8.

Johnson D G, Schwarz, J. K., Cress, W. D. and Nevins, J. R. Expression of transcription factor E2F1 induces quiescent cells to enter S phase. *Nature* 1993; 365:349-52.

Kasid, U. Raf-1 protein kinase, signal transduction, and targeted intervention of radiation response. *Experimental Biology and Medicine* 2001, 226, 624-625.

Kato J, Matsushime H, Hiebert S W, Ewen M E, Sherr C J. Direct binding of cyclin D to the retinoblastoma gene product (pRb) and pRb phosphorylation by the cyclin D-dependent kinase CDK4. *Genes Dev* 1993; 7:331-42.

Knudsen E S, Wang J Y. Differential regulation of retinoblastoma protein function by specific Cdk phosphorylation sites. *Journal of Biological Chemistry* 1996, 271(14), 8313-8320.

Knudsen E S, Wang J Y. Dual mechanisms for the inhibition of E2F binding to RB by cyclin-dependent kinase-mediated RB phosphorylation. *Molecular and Cellular Biology* 1997, 17(10), 5771-5783.

Lam E W, La T N. DP and E2F proteins: coordinating transcription with cell cycle progression. [Review]. *Curr Opin Cell Biol* 1994; 6(6):859-66.

Lee J O, Russo A A, Pavletich N P. Structure of the retinoblastoma tumour-suppressor pocket domain bound to a peptide from HPV E7. *Nature* 1998; 391(6670):859-65.

Macleod K. Tumor suppressor genes. Curr Opin Genet Dev 2000; 10(1):81-93.

Miel, H, Rault, S. Total deprotection of N,N'-bis(tert-butoxycarbonyl)guanidines using SnCl4. Tetrahedron Letters 1997, 38, 7865-7866.

Morris E J, Dyson N J. Retinoblastoma protein partners. Adv Cancer Res 2001; 82:1-54.

Muller H, Bracken A P, Vernell R, et al. E2Fs regulate the expression of genes involved in differentiation, development, proliferation, and apoptosis. Genes Dev 2001; 15(3): 267-85.

Muller H, Helin K. The E2F transcription factors: key regulators of cell proliferation. Biochim Biophys Acta 2000; 1470(1):M1-M12.

Nevins J R. Cell cycle targets of the DNA tumor viruses. Current Opinion in Genetics & Development 1994, 4(1), 130-134.

Nevins J R. Disruption of cell-cycle control by viral oncoproteins. [Review]. Biochemical Society Transactions 1993; 21(4):935-8.

Nevins J R. E2F: a link between the Rb tumor suppressor protein and viral oncoproteins. Science 1992, 258(5081), 424-429.

Nevins, J R. The Rb/E2F pathway and cancer. Human Molecular Genetics 2001, 10, 699-703.

Norbury C, Nurse P. Animal cell cycles and their control. Ann Rev Biochem 1992; 61:441-70.

Paggi, M G, Baldi, A, Bonetto, F, Giordano, A. Retinoblastoma protein family in cell cycle and cancer: A review. Journal of Cellular Biochemistry 1996, 62, 418-430.

Prives C, Hall P A. The p53 pathway. J Pathol 1999; 187(1):112-26.

Reddy G P. Cell cycle: regulatory events in G1->S transition of mammalian cells. Journal of Cellular Biochemistry 1994, 54(4), 379-386.

Reed S I. Control of the G1/S transition. Cancer Surveys 1997, 29, 7-23.

Ren B, Cam H, Takahashi Y, et al. E2F integrates cell cycle progression with DNA repair, replication, and G(2)/M checkpoints. Genes Dev 2002; 16(2):245-56.

Rini, B I. Sorafenib. Expert Opinion on Pharmacotherapy 2006, 7, 453-461.

Rudin, C M, HolmLund, J, Fleming, G F, Mani, S, Stadler, W M. et al. Phase I trial of ISIS 5132, an antisense oligonucleotide inhibitor of c-raf-1, administered by 24-hour weekly infusion to patients with advanced cancer. Clinical Cancer Research 2001, 7, 1214-1220.

Sager R. Tumor suppressor genes in the cell cycle. Curr Opin Cell Biol 1992; 4155-160.

Sager R. Tumor suppressor genes: The puzzle and the promise. Science 1989; 246:1406-12.

Sherr C J, McCormick F. The RB and p53 pathways in cancer. Cancer Cell 2002; 2(2):103-12.

Sherr C J, Roberts J M. Inhibitors of mammalian G1 cyclin-dependent kinases. [Review]. Genes & Development 1995; 9(10):1149-63.

Sherr C J. Cell cycle control and cancer. Harvey Lect 2000; 96:73-92.

Sherr C J. Mammalian G1 cyclins and cell cycle progression. Proc Assoc Am Physicians 1995; 107(2):181-6.

Sherr C J. The ins and outs of RB: Coupling gene expression to the cell cycle clock. Trends in Cell Biology 1994, 4, 15-18.

Sherr C J. The ins and outs of RB: Coupling gene expression to the cell cycle clock. Trends Cell Biol 1994; 4:15-8.

Slansky J E, Farnham P J. Introduction to the E2F family: protein structure and gene regulation. [Review]. Curr Top Microbiol Immunol 1996; 208(1):1-30.

Stiegler P, Kasten M, Giordano A. The RB family of cell cycle regulatory factors. J Cell Biochem Suppl 1998; 31:30-6.

Takahashi Y, Rayman J B, Dynlacht B D. Analysis of promoter binding by the E2F and pRb families in vivo: distinct E2F proteins mediate activation and repression. Genes Dev 2000; 14:804-16.

Taya Y, Yasuda H, Kamijo M, et al. In vitro phosphorylation of the tumor suppressor gene RBprotein by mitosis-specific histone H1 kinase. Biochem Biophys Res Commun 1989; 164(1):580-6.

Taya Y. RB kinases and RB-binding proteins: new points of view. [Review][50 refs]. Trends Biochem Sci 1997; 22(1): 14-7.

Taylor W R, Stark G R. Regulation of the G2/M transition by p53. Oncogene 2001; 20(15):1803-15.

Tonini T, Hillson C, Claudio P P. Interview with the retinoblastoma family members: do they help each other? J Cell Physiol 2002; 192(2):138-50.

Trimarchi J M, Lees J A. Transcription: Sibling rivalry in the E2F family. Nat Rev Mol Cell Biol 2002; 3(1):11-20.

Wang S, Ghosh R, Chellappan S. Raf-1 physically interacts with Rb and regulates its function: A link between mitogenic signaling and cell cycle regulation. Mol Cell Biol 1998; 18(12):7487-98.

Wang S, Nath N, Minden A, Chellappan S. Regulation of Rb and E2F by signal transduction cascades: divergent effects of JNK1 and p38 kinases. Embo J 1999; 18(6):1559-70.

Wang, S, Ghosh, R N, Chellappan, S P. Raf-1 physically interacts with Rb and regulates its function: a link between mitogenic signaling and cell cycle regulation. Molecular and Cellular Biology 1998, 18, 7487-7498.

Weinberg R A. E2F and cell proliferation: a world turned upside down. [Review]. Cell 1996; 85(4):457-9.

Weinberg, R A. The Retinoblastoma Protein and Cell-Cycle Control. Cell 1995, 81, 323-330.

Welch P J, Wang J Y. Disruption of retinoblastoma protein function by coexpression of its C pocket fragment. Genes & Development 1995; 9(1):31-46.

Welch P J, Wang J Y J. A C-terminal protein-binding domain in the retinoblastoma protein regulates nuclear c-Abl tyrosine in the cell cycle. Cell 1993; 75:779-90.

Wilhelm S, Carter C, Lynch M, et al. Discovery and development of sorafenib: a multikinase inhibitor for treating cancer. Nature Reviews Drug Discovery 2006, 5(10), 8358-8344.

Wilhelm, S M, Carter, C, Tang, L Y, Wilkie, D, McNabola, A. et al. BAY 43-9006 exhibits broad spectrum oral antitumor activity and targets the RAF/MEK/ERK pathway and receptor tyrosine kinases involved in tumor progression and angiogenesis. Cancer Research 2004, 64, 7099-7109.

Yin H, Hamilton A D. Strategies for targeting protein-protein interactions with synthetic agents. Angewandte Chemie International Ed. in English 2005, 44(27), 4130-4163.

Yong, Y F, Kowalski, J A, Lipton, M A. Facile and efficient guanylation of amines using thioureas and Mukaiyama's reagent. Journal of Organic Chemistry 1997, 62, 1540-1542.

What is claimed is:

1. A compound selected from the group consisting of the following compounds and pharmaceutically acceptable salts thereof:

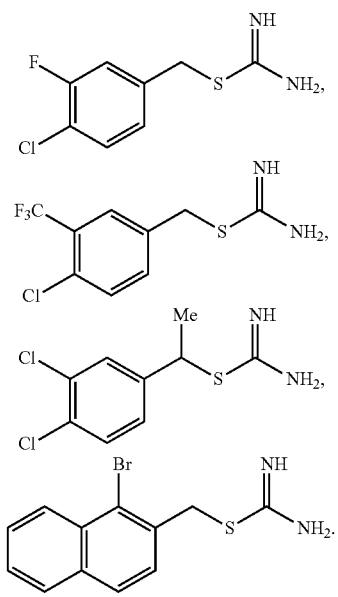

2. A pharmaceutical composition comprising the compound or pharmaceutically acceptable salt thereof of claim 1.

3. A pharmaceutical composition comprising the compound or pharmaceutically acceptable salt thereof of claim 1, wherein the compound is the following compound:

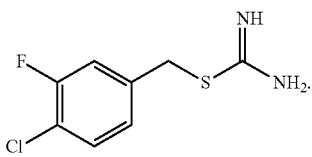 [SMILES: N=C(N)SCc1ccc(Cl)c(F)c1]

4. A method of treating or ameliorating a cell proliferation disorder, comprising administering to a subject in need of such treatment an effective amount of a compound or pharmaceutically acceptable salt thereof according to claim 1.

5. The method of claim 4, wherein the treatment comprises contacting the proliferating cells of the cell proliferation disorder with the compound or pharmaceutically acceptable salt thereof.

6. The method of claim 4, wherein the regulation of proliferation of cells in the cell proliferation disorder is mediated by at least one protein selected from the group consisting of retinoblastoma tumor suppressor protein and serine threonine kinase Raf 1.

7. The method of claim 4, wherein the cell proliferation disorder is a cancer.

8. The method of claim 4, wherein the cell proliferation disorder is a non-cancerous cell proliferation disorder.

9. The method of claim 4, wherein the cell proliferation disorder is a cancer selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, acute lymphocytic leukemia, lymphocytic leukemia, large granular lymphocytic leukemia, acute myelocytic leukemia, chronic leukemia, polycythemia vera, Hodgkin's lymphoma, non-Hodgkin's lymphoma, multiple myeloma, Waldenstrobm's macroglobulinemia, heavy chain disease, lymphoblastic leukemia, T-cell leukemia, T-lymphocytic leukemia, T-lymphoblastic leukemia, B cell leukemia, B-lymphocytic leukemia, mixed cell leukemias, myeloid leukemias, myelocytic leukemia, myelogenous leukemia, neutrophilic leukemia, eosinophilic leukemia, monocytic leukemia, myelomonocytic leukemia, Naegeli-type myeloid leukemia, nonlymphocytic leukemia, osteosarcoma, promyelocytic leukemia, non-small cell lung cancer, epithelial lung carcinoma, pancreatic carcinoma, pancreatic ductal adenocarcinoma, glioblastoma, metastatic breast cancer, melanoma, and prostate cancer.

10. The method of claim 4, wherein the cell proliferation disorder is a cancer selected from the group consisting of osteosarcoma, promyelocytic leukemia, non-small cell lung cancer, epithelial lung carcinoma, pancreatic carcinoma, pancreatic ductal adenocarcinoma, glioblastoma, metastatic breast cancer, melanoma, and prostate cancer.

11. A method of inhibiting angiogenesis, comprising administering to a subject in need of such treatment an effective amount of a compound or pharmaceutically acceptable salt thereof according to claim 1.

12. The compound or pharmaceutically acceptable salt thereof of claim 1, wherein the compound is the following compound:

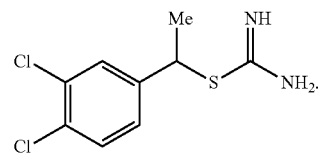 [SMILES: CC(SC(=N)N)c1ccc(Cl)c(Cl)c1]

13. The compound or pharmaceutically acceptable salt thereof of claim 1, wherein the compound is the following compound:

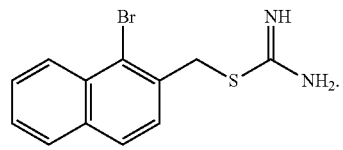 [SMILES: N=C(N)SCc1ccc2ccccc2c1Br]

14. The compound or pharmaceutically acceptable salt thereof of claim 1, wherein the compound is the following compound:

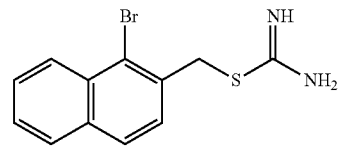 [SMILES: N=C(N)SCc1ccc2ccccc2c1Br]

15. The compound or pharmaceutically acceptable salt thereof of claim 1, wherein the compound is the following compound:

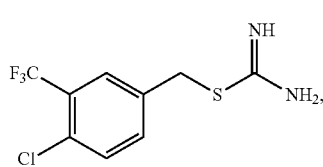

16. The compound or pharmaceutically acceptable salt thereof of claim 1, wherein the pharmaceutically acceptable salts of the compounds of the following formula:

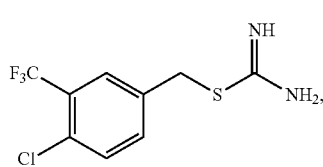

are selected from the group consisting of sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, and mandelate salts.

17. A pharmaceutical composition according to claim 2 comprising a pharmaceutically acceptable carrier.

18. The compound or pharmaceutically acceptable salt thereof of claim 1, wherein the compound is selected from the group consisting of the following compounds:

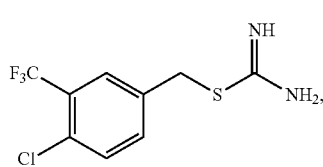

-continued

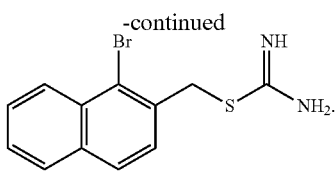

19. The compound or pharmaceutically acceptable salt thereof of claim 1, wherein the compound is selected from the group consisting of the following compounds:

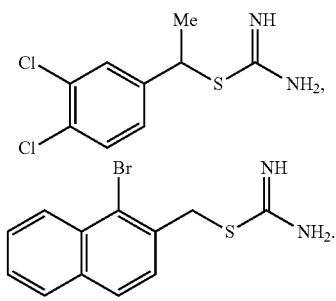

20. The method of claim 4, wherein the compound administered is the following compound:

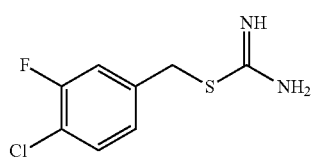 [SMILES: N=C(N)SCc1ccc(Cl)c(F)c1]

or a pharmaceutically acceptable salt thereof.

21. The method of claim 7, wherein the compound administered is the following compound:

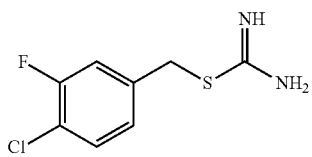 [SMILES: N=C(N)SCc1ccc(Cl)c(F)c1]

or a pharmaceutically acceptable salt thereof.

22. The method of claim 9, wherein the compound administered is the following compound:

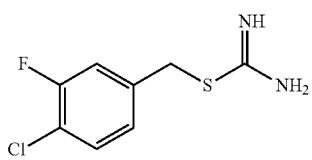 [SMILES: N=C(N)SCc1ccc(Cl)c(F)c1]

or a pharmaceutically acceptable salt thereof.

23. The method of claim 10, wherein the compound administered is the following compound:

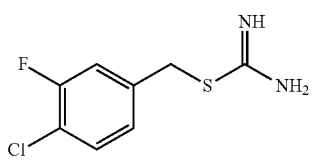 [SMILES: N=C(N)SCc1ccc(Cl)c(F)c1]

or a pharmaceutically acceptable salt thereof.

* * * * *

UNITED STATES PATENT AND TRADEMARK OFFICE
CERTIFICATE OF CORRECTION

PATENT NO. : 9,656,953 B2
APPLICATION NO. : 14/171273
DATED : May 23, 2017
INVENTOR(S) : Said M. Sebti et al.

It is certified that error appears in the above-identified patent and that said Letters Patent is hereby corrected as shown below:

In the Specification

Column 1, Line 12 through Line 16 should read:
GOVERNMENT SUPPORT
This invention was made with government support under grant numbers CA063136 and CA118210 awarded by the National Institutes of Health. The Government has certain rights in the invention.

Signed and Sealed this
Twenty-third Day of April, 2019

Andrei Iancu
*Director of the United States Patent and Trademark Office*